US008883980B2

(12) United States Patent
Umaña et al.

(10) Patent No.: US 8,883,980 B2
(45) Date of Patent: Nov. 11, 2014

(54) ANTIGEN BINDING MOLECULES WITH INCREASED FC RECEPTOR BINDING AFFINITY AND EFFECTOR FUNCTION

(75) Inventors: Pablo Umaña, Zurich (CH); Peter Brünker, Hittnau (CH); Claudia Ferrera Koller, Zug (CH); Tobias Suter, Windisch (CH); Ursula Püntener, Baden (CH); Ekkehard Mössner, Kreuzlingen (CH)

(73) Assignee: Roche Glycart AG, Schlieren (CH)

( * ) Notice: Subject to any disclaimer, the term of this patent is extended or adjusted under 35 U.S.C. 154(b) by 1795 days.

(21) Appl. No.: 11/889,975

(22) Filed: Aug. 17, 2007

(65) Prior Publication Data

US 2009/0010921 A1 Jan. 8, 2009

Related U.S. Application Data

(62) Division of application No. 10/981,738, filed on Nov. 5, 2004.

(60) Provisional application No. 60/517,096, filed on Nov. 5, 2003.

(51) Int. Cl.
*C07K 16/28* (2006.01)
*C07K 16/30* (2006.01)
*A61K 39/00* (2006.01)

(52) U.S. Cl.
CPC ......... *C07K 16/2887* (2013.01); *C07K 2317/92* (2013.01); *C07K 2317/24* (2013.01); *C07K 2317/41* (2013.01); *C07K 2317/72* (2013.01); *C07K 2317/56* (2013.01); *C07K 2317/734* (2013.01); *C07K 2317/53* (2013.01); *C07K 2317/567* (2013.01); *C07K 2317/52* (2013.01); *C07K 2317/732* (2013.01); *A61K 2039/505* (2013.01); *Y10S 530/808* (2013.01); *Y10S 530/866* (2013.01); *Y10S 530/867* (2013.01)
USPC .............. 530/387.3; 530/388.22; 530/388.73; 530/388.8; 530/388.85; 530/389.6; 530/389.7; 530/808; 530/866; 530/867

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. |
| 5,047,335 A | 9/1991 | Paulson et al. |
| 5,225,539 A | 7/1993 | Winter |
| 5,262,296 A | 11/1993 | Ogawa et al. |
| 5,500,362 A | 3/1996 | Robinson et al. |
| 5,595,721 A | 1/1997 | Kaminski et al. |
| 5,677,180 A | 10/1997 | Robinson et al. |
| 5,721,108 A | 2/1998 | Robinson et al. |
| 5,736,137 A | 4/1998 | Anderson et al. |
| 5,776,456 A | 7/1998 | Anderson et al. |
| 5,843,398 A | 12/1998 | Kaminski et al. |
| 5,843,439 A | 12/1998 | Anderson et al. |
| 6,015,542 A | 1/2000 | Kaminski et al. |
| 6,090,365 A | 7/2000 | Kaminski et al. |
| 6,120,767 A | 9/2000 | Robinson et al. |
| 6,127,526 A | 10/2000 | Blank |
| 6,171,586 B1 | 1/2001 | Lam et al. |
| 6,180,370 B1 | 1/2001 | Queen et al. |
| 6,287,537 B1 | 9/2001 | Kaminski et al. |
| 6,333,398 B1 | 12/2001 | Blank |
| 6,399,061 B1 | 6/2002 | Anderson et al. |
| 6,417,335 B1 | 7/2002 | Basey et al. |
| 6,451,284 B1 | 9/2002 | Raestetter et al. |
| 6,455,043 B1 | 9/2002 | Grillo-López |
| 6,489,447 B1 | 12/2002 | Basey et al. |
| 6,528,624 B1 | 3/2003 | Idusogie et al. |
| 6,602,684 B1 | 8/2003 | Umaña et al. |
| 6,632,927 B2 | 10/2003 | Adair et al. |
| 6,652,852 B1 | 11/2003 | Robinson et al. |
| 6,682,734 B1 | 1/2004 | Anderson et al. |
| 6,737,056 B1 | 5/2004 | Presta |
| 6,797,814 B2 | 9/2004 | Blank |
| 6,815,184 B2 | 11/2004 | Stomp et al. |
| 6,846,476 B2 | 1/2005 | White |
| 6,893,625 B1 | 5/2005 | Robinson et al. |
| 6,896,885 B2 | 5/2005 | Hanna |

(Continued)

FOREIGN PATENT DOCUMENTS

| | | |
|---|---|---|
| CN | 1169952 C | 6/2004 |
| EP | 0 173 494 A2 | 3/1986 |

(Continued)

OTHER PUBLICATIONS

Withoff et al., "Characterization of BIS20x3, a bi-specific antibody activating and retargeting T-cells to CD20-positive B-cells", British Journal of Cancer (2001) 84(8), 1115-1121.*
De Pascalis et al."Grafting of abbreviated complementarity determining regions containing specificity determining residues essential for ligand contact to engineer al ess immunogenic humanzied monoclonal antibody", Journal of Immunology, 2002. vol. 169, pp. 3076-3084.*
Rudikoff et al. "Single amino acid substitution altering antigen binding specificity", Proceedings of the National Academy of Sciences, 1982. vol. 79, pp. 1979-1983.*

(Continued)

*Primary Examiner* — Ron Schwadron
(74) *Attorney, Agent, or Firm* — Morrison & Foerster LLP

(57) ABSTRACT

The present invention relates to antigen binding molecules (ABMs). In particular embodiments, the present invention relates to recombinant monoclonal antibodies, including chimeric, primatized or humanized antibodies specific for human CD20. In addition, the present invention relates to nucleic acid molecules encoding such ABMs, and vectors and host cells comprising such nucleic acid molecules. The invention further relates to methods for producing the ABMs of the invention, and to methods of using these ABMs in treatment of disease. In addition, the present invention relates to ABMs with modified glycosylation having improved therapeutic properties, including antibodies with increased Fc receptor binding and increased effector function.

16 Claims, 26 Drawing Sheets

(56) References Cited

U.S. PATENT DOCUMENTS

| | | |
|---|---|---|
| 6,991,790 B1 | 1/2006 | Lam et al. |
| 7,074,406 B2 | 7/2006 | Black et al. |
| 7,151,164 B2 | 12/2006 | Hansen et al. |
| 7,192,586 B2 | 3/2007 | Bander |
| 7,262,277 B2 | 8/2007 | Lancaster |
| 7,355,008 B2 | 4/2008 | Stavenhagen et al. |
| 7,381,560 B2 | 6/2008 | Anderson et al. |
| 7,402,728 B2 | 7/2008 | Chan et al. |
| 7,422,739 B2 | 9/2008 | Anderson et al. |
| 7,501,121 B2 | 3/2009 | Tchistiakova et al. |
| 7,514,223 B2 | 4/2009 | Yang et al. |
| 7,517,670 B2 | 4/2009 | Umaña et al. |
| 7,531,645 B2 | 5/2009 | Basey et al. |
| 7,572,456 B2 | 8/2009 | Johnson et al. |
| 7,575,893 B2 | 8/2009 | Simmons |
| 7,601,335 B2 | 10/2009 | McCutcheon et al. |
| 7,682,612 B1 | 3/2010 | White et al. |
| 7,691,989 B2 | 4/2010 | Ernst et al. |
| 7,708,994 B2 | 5/2010 | Benyunes |
| 7,744,877 B2 | 6/2010 | Anderson et al. |
| 7,799,900 B2 | 9/2010 | Adams et al. |
| 7,820,161 B1 | 10/2010 | Curd et al. |
| 7,892,543 B2 | 2/2011 | Ono et al. |
| 7,906,329 B2 | 3/2011 | Umana et al. |
| 7,976,838 B2 | 7/2011 | Benyunes |
| 8,021,850 B2 | 9/2011 | Umaña et al. |
| 8,021,856 B2 | 9/2011 | Umaña et al. |
| 8,592,156 B2 | 11/2013 | Liu et al. |
| 2001/0018041 A1 | 8/2001 | Hanna et al. |
| 2002/0006404 A1 | 1/2002 | Hanna et al. |
| 2002/0009444 A1 | 1/2002 | Grillo-López |
| 2002/0028178 A1 | 3/2002 | Hanna et al. |
| 2002/0058029 A1 | 5/2002 | Hanna |
| 2002/0128448 A1 | 9/2002 | Reff |
| 2002/0147312 A1 | 10/2002 | O'Keefe et al. |
| 2002/0159996 A1 | 10/2002 | Hariharan et al. |
| 2002/0197255 A1 | 12/2002 | Anderson et al. |
| 2002/0197256 A1 | 12/2002 | Grewal |
| 2003/0003097 A1 | 1/2003 | Reff et al. |
| 2003/0021781 A1 | 1/2003 | Anderson et al. |
| 2003/0026804 A1 | 2/2003 | Grillo-Lopez |
| 2003/0039649 A1 | 2/2003 | Foote |
| 2003/0040606 A1 | 2/2003 | Leung |
| 2003/0103971 A1 | 6/2003 | Hariharan et al. |
| 2003/0118592 A1 | 6/2003 | Ledbetter et al. |
| 2003/0129185 A1 | 7/2003 | Ono et al. |
| 2003/0133930 A1 | 7/2003 | Goldenberg et al. |
| 2003/0157108 A1 | 8/2003 | Presta |
| 2003/0161832 A1 | 8/2003 | Bander |
| 2003/0175884 A1 | 9/2003 | Umaña et al. |
| 2003/0180290 A1 | 9/2003 | Hariharan et al. |
| 2003/0180292 A1 | 9/2003 | Hanna et al. |
| 2003/0190689 A1 | 10/2003 | Crosby et al. |
| 2003/0206903 A1 | 11/2003 | Grillo-Lopez |
| 2003/0211107 A1 | 11/2003 | Hariharan et al. |
| 2004/0044187 A1 | 3/2004 | Sato et al. |
| 2004/0072290 A1 | 4/2004 | Umaña et al. |
| 2004/0093621 A1 | 5/2004 | Shitara et al. |
| 2004/0132066 A1 | 7/2004 | Balint et al. |
| 2004/0132097 A1 | 7/2004 | Bacus et al. |
| 2004/0132101 A1 | 7/2004 | Lazar et al. |
| 2004/0185045 A1 | 9/2004 | Koenig et al. |
| 2004/0191256 A1 | 9/2004 | Raju |
| 2004/0202655 A1 | 10/2004 | Morton et al. |
| 2004/0202658 A1 | 10/2004 | Benyunes |
| 2004/0213784 A1 | 10/2004 | Grillo-Lopez et al. |
| 2004/0229310 A1 | 11/2004 | Simmons |
| 2004/0241817 A1 | 12/2004 | Umaña et al. |
| 2005/0032130 A1 | 2/2005 | Beresini et al. |
| 2005/0033028 A1 | 2/2005 | Leung |
| 2005/0042664 A1 | 2/2005 | Wu et al. |
| 2005/0053602 A1 | 3/2005 | Brunetta |
| 2005/0058649 A1 | 3/2005 | Landes et al. |
| 2005/0064514 A1 | 3/2005 | Stavenhagen et al. |
| 2005/0074843 A1 | 4/2005 | Umaña et al. |
| 2005/0079605 A1 | 4/2005 | Umaña et al. |
| 2005/0095243 A1 | 5/2005 | Chan et al. |
| 2005/0112060 A1 | 5/2005 | White |
| 2005/0123540 A1 | 6/2005 | Hanna et al. |
| 2005/0123546 A1 | 6/2005 | Umaña et al. |
| 2005/0158316 A1 | 7/2005 | Lam et al. |
| 2005/0163708 A1 | 7/2005 | Robinson et al. |
| 2005/0163775 A1 | 7/2005 | Chan et al. |
| 2005/0180975 A1 | 8/2005 | Hanna |
| 2005/0186206 A1 | 8/2005 | Brunetta |
| 2005/0191297 A1 | 9/2005 | Brunetta |
| 2005/0271658 A1 | 12/2005 | Brunetta |
| 2005/0272128 A1 | 12/2005 | Umaña et al. |
| 2005/0276803 A1 | 12/2005 | Chan et al. |
| 2006/0002930 A1 | 1/2006 | Brunetta et al. |
| 2006/0024295 A1 | 2/2006 | Brunetta |
| 2006/0024300 A1 | 2/2006 | Adams et al. |
| 2006/0051345 A1 | 3/2006 | Frohna |
| 2006/0057149 A1 | 3/2006 | Johnson et al. |
| 2006/0062787 A1 | 3/2006 | Hitraya |
| 2006/0067930 A1 | 3/2006 | Adams et al. |
| 2006/0073148 A1 | 4/2006 | Tchistiakova et al. |
| 2006/0099662 A1 | 5/2006 | Chuntharapi et al. |
| 2006/0110387 A1 | 5/2006 | Brunetta |
| 2006/0121028 A1 | 6/2006 | Reff |
| 2006/0134111 A1 | 6/2006 | Agarwal |
| 2006/0135430 A1 | 6/2006 | Chan et al. |
| 2006/0171950 A1 | 8/2006 | Hariharan et al. |
| 2006/0179501 A1 | 8/2006 | Chan et al. |
| 2006/0188495 A1 | 8/2006 | Barron et al. |
| 2006/0233797 A1 | 10/2006 | Gujrathi |
| 2006/0240007 A1 | 10/2006 | Sanders |
| 2006/0246004 A1 | 11/2006 | Adams et al. |
| 2006/0263355 A1 | 11/2006 | Quan et al. |
| 2006/0275284 A1 | 12/2006 | Hanna |
| 2006/0286100 A1 | 12/2006 | Harjharan et al. |
| 2006/0286101 A1 | 12/2006 | Hariharan et al. |
| 2007/0003544 A1 | 1/2007 | Hanna |
| 2007/0009518 A1 | 1/2007 | Novobrantseva et al. |
| 2007/0009519 A1 | 1/2007 | Hariharan et al. |
| 2007/0020260 A1 | 1/2007 | Presta |
| 2007/0025987 A1 | 2/2007 | Brunetta |
| 2007/0031331 A1 | 2/2007 | Brunetta et al. |
| 2007/0071745 A1 | 3/2007 | Umaña et al. |
| 2007/0212733 A1 | 9/2007 | Martin |
| 2007/0231324 A1 | 10/2007 | Ashkenazi |
| 2008/0038261 A1 | 2/2008 | Grillo-Lopez |
| 2008/0044421 A1 | 2/2008 | Ashkenazi |
| 2008/0075719 A1 | 3/2008 | Chan et al. |
| 2008/0095771 A1 | 4/2008 | Barron et al. |
| 2008/0176257 A9 | 7/2008 | Chuntharapai et al. |
| 2008/0280322 A9 | 11/2008 | Umaña et al. |
| 2009/0004189 A1 | 1/2009 | Behrens et al. |
| 2009/0010921 A1 | 1/2009 | Umaña et al. |
| 2009/0053786 A1 | 2/2009 | Kao et al. |
| 2009/0060913 A1 | 3/2009 | Friess et al. |
| 2009/0098118 A1 | 4/2009 | Friess et al. |
| 2009/0110688 A1 | 4/2009 | Fertig et al. |
| 2009/0148435 A1 | 6/2009 | Lebreton et al. |
| 2009/0155257 A1 | 6/2009 | Adams et al. |
| 2009/0162351 A1 | 6/2009 | Brown et al. |
| 2009/0162352 A1 | 6/2009 | Adler et al. |
| 2009/0169550 A1 | 7/2009 | Dummer |
| 2009/0175854 A1 | 7/2009 | Ashkenazi |
| 2009/0208500 A1 | 8/2009 | Joly et al. |
| 2009/0214561 A1 | 8/2009 | Close |
| 2009/0246197 A1 | 10/2009 | Dumontet et al. |
| 2009/0269339 A1 | 10/2009 | Kelman et al. |
| 2009/0304690 A1 | 12/2009 | Umaña et al. |
| 2009/0311255 A1 | 12/2009 | Brunetta et al. |
| 2009/0317384 A1 | 12/2009 | Ashkenazi |
| 2010/0158903 A1 | 6/2010 | Smith et al. |
| 2010/0247484 A1 | 9/2010 | Barchet et al. |
| 2010/0255013 A1 | 10/2010 | Presta |
| 2010/0310581 A1 | 12/2010 | Dumontet et al. |
| 2011/0008250 A1 | 1/2011 | Curd et al. |
| 2011/0008337 A1 | 1/2011 | Curd et al. |
| 2011/0008338 A1 | 1/2011 | Curd et al. |
| 2011/0052488 A1 | 3/2011 | Dennis, Jr. et al. |

(56) References Cited

U.S. PATENT DOCUMENTS

| | | |
|---|---|---|
| 2011/0076273 A1 | 3/2011 | Adler et al. |
| 2011/0086050 A1 | 4/2011 | Presta |
| 2011/0142825 A1 | 6/2011 | Umaña et al. |
| 2011/0165151 A1 | 7/2011 | Herting et al. |
| 2011/0165152 A1 | 7/2011 | Dreyling et al. |
| 2011/0177067 A1 | 7/2011 | Dumontet et al. |
| 2011/0243931 A1 | 10/2011 | Friess et al. |
| 2012/0122206 A1 | 5/2012 | Umana et al. |
| 2012/0251534 A1 | 10/2012 | Grillo-Lopez |

FOREIGN PATENT DOCUMENTS

| | | |
|---|---|---|
| EP | 0 274 394 A2 | 7/1988 |
| EP | 0 125 023 B1 | 6/1991 |
| EP | 0 669 836 B1 | 9/1995 |
| EP | 0 752 248 B1 | 1/1997 |
| EP | 0 999 853 B1 | 5/2000 |
| EP | 1 005 870 B1 | 6/2000 |
| EP | 1 131 096 B1 | 9/2001 |
| EP | 1 176 195 A1 | 1/2002 |
| EP | 2 000 149 B1 | 12/2008 |
| WO | WO 88/04936 A1 | 7/1988 |
| WO | WO-89/09402 A1 | 10/1989 |
| WO | WO 92/07466 A1 | 5/1992 |
| WO | WO-94/11026 A1 | 5/1994 |
| WO | WO 94/11026 A2 | 5/1994 |
| WO | WO 97/17446 A2 | 5/1997 |
| WO | WO 98/04281 A1 | 2/1998 |
| WO | WO-98/23645 A1 | 6/1998 |
| WO | WO-98/56418 A1 | 12/1998 |
| WO | WO 98/58964 A1 | 12/1998 |
| WO | WO 99/22764 A1 | 5/1999 |
| WO | WO 99/54342 A1 | 10/1999 |
| WO | WO-99/57134 A1 | 11/1999 |
| WO | WO 00/09160 A1 | 2/2000 |
| WO | WO 00/10007 A2 | 2/2000 |
| WO | WO 00/20864 A1 | 4/2000 |
| WO | WO 00/27428 A1 | 5/2000 |
| WO | WO 00/27433 A1 | 5/2000 |
| WO | WO 00/42072 A2 | 7/2000 |
| WO | WO 00/67795 | 11/2000 |
| WO | WO 00/67796 A1 | 11/2000 |
| WO | WO 01/03734 A1 | 1/2001 |
| WO | WO 01/10460 A1 | 2/2001 |
| WO | WO 01/10462 A1 | 2/2001 |
| WO | WO 01/34194 A1 | 5/2001 |
| WO | WO 01/71005 A2 | 9/2001 |
| WO | WO 01/74388 A1 | 10/2001 |
| WO | WO 01/80884 A1 | 11/2001 |
| WO | WO 01/97858 A2 | 12/2001 |
| WO | WO 02/04021 A1 | 1/2002 |
| WO | WO 02/22212 A2 | 3/2002 |
| WO | WO 02/34790 A1 | 5/2002 |
| WO | WO 02/061105 A2 | 8/2002 |
| WO | WO 02/078766 A2 | 10/2002 |
| WO | WO 02/079255 A1 | 10/2002 |
| WO | WO 03/002607 A1 | 1/2003 |
| WO | WO 03/011878 A2 | 2/2003 |
| WO | WO 03/024388 A2 | 3/2003 |
| WO | WO 03/035835 A2 | 5/2003 |
| WO | WO 03/056914 A1 | 7/2003 |
| WO | WO 03/061694 A1 | 7/2003 |
| WO | WO 03/068821 A2 | 8/2003 |
| WO | WO 03/078614 A2 | 9/2003 |
| WO | WO 03/079750 A2 | 10/2003 |
| WO | WO 2004/024927 A1 | 3/2004 |
| WO | WO 2004/035607 A2 | 4/2004 |
| WO | WO 2004/056312 A2 | 7/2004 |
| WO | WO 2004/057002 A2 | 7/2004 |
| WO | WO 2004/060052 A2 | 7/2004 |
| WO | WO 2004/060053 A2 | 7/2004 |
| WO | WO 2004/063351 A2 | 7/2004 |
| WO | WO 2004/065540 A2 | 8/2004 |
| WO | WO 2004/091657 A2 | 10/2004 |
| WO | WO 2004/099249 A2 | 11/2004 |
| WO | WO 2004/103404 A1 | 12/2004 |
| WO | WO 2005/000351 A2 | 1/2005 |
| WO | WO 2005/005462 A2 | 1/2005 |
| WO | WO 2005/017529 A1 | 2/2005 |
| WO | WO 2005/023302 A2 | 3/2005 |
| WO | WO 2005/044859 A2 | 5/2005 |
| WO | WO 2005/060999 A2 | 7/2005 |
| WO | WO 2005/061542 A2 | 7/2005 |
| WO | WO 2005/062955 A2 | 7/2005 |
| WO | WO 2005/079479 A2 | 9/2005 |
| WO | WO 2005/108989 A2 | 11/2005 |
| WO | WO 2005/113003 A2 | 12/2005 |
| WO | WO 2005/114218 A2 | 12/2005 |
| WO | WO 2005/115453 A2 | 12/2005 |
| WO | WO 2005/117972 A2 | 12/2005 |
| WO | WO 2005/117978 A2 | 12/2005 |
| WO | WO 2005/120437 A2 | 12/2005 |
| WO | WO 2006/012508 A2 | 2/2006 |
| WO | WO 2006/029224 A2 | 3/2006 |
| WO | WO 2006/029275 A2 | 3/2006 |
| WO | WO 2006/031370 A2 | 3/2006 |
| WO | WO 2006/041680 A2 | 4/2006 |
| WO | WO-2006/066086 A1 | 6/2006 |
| WO | WO 2006/066089 A1 | 6/2006 |
| WO | WO 2006/068867 A1 | 6/2006 |
| WO | WO-2006/069403 A2 | 6/2006 |
| WO | WO-2006/069403 A3 | 6/2006 |
| WO | WO-2006/076651 A2 | 7/2006 |
| WO | WO-2006/076651 A3 | 7/2006 |
| WO | WO-2006/084264 A2 | 8/2006 |
| WO | WO-2006/084264 A3 | 8/2006 |
| WO | WO-2006/093923 A2 | 9/2006 |
| WO | WO-2006/093923 A3 | 9/2006 |
| WO | WO-2006/093923 C1 | 9/2006 |
| WO | WO-2006/093923 C2 | 9/2006 |
| WO | WO-2006/113308 A1 | 10/2006 |
| WO | WO-2006/113308 C1 | 10/2006 |
| WO | WO-2006/116369 A2 | 11/2006 |
| WO | WO-2006/116369 A3 | 11/2006 |
| WO | WO-2006/125140 A2 | 11/2006 |
| WO | WO-2006/125140 A3 | 11/2006 |
| WO | WO-2006/125140 C1 | 11/2006 |
| WO | WO-2006/127517 A2 | 11/2006 |
| WO | WO-2006/127517 A3 | 11/2006 |
| WO | WO-2006/127517 C1 | 11/2006 |
| WO | WO-2006/133148 A2 | 12/2006 |
| WO | WO-2006/133148 A3 | 12/2006 |
| WO | WO-2007/031875 A2 | 3/2007 |
| WO | WO-2007/031875 A3 | 3/2007 |
| WO | WO-2007/059188 A1 | 5/2007 |
| WO | WO-2007/062090 A2 | 5/2007 |
| WO | WO-2007/062090 A3 | 5/2007 |
| WO | WO-2007/062090 C1 | 5/2007 |
| WO | WO-2007/064911 A1 | 6/2007 |
| WO | WO-2008/122007 A1 | 10/2008 |
| WO | WO-2008/157282 A1 | 12/2008 |
| WO | WO-2009/008607 A1 | 1/2009 |
| WO | WO-2009/009523 A2 | 1/2009 |
| WO | WO-2009/009523 A3 | 1/2009 |
| WO | WO-2009/030368 A1 | 3/2009 |
| WO | WO-2009/040268 A1 | 4/2009 |
| WO | WO-2009/049841 A1 | 4/2009 |
| WO | WO-2009/053038 A2 | 4/2009 |
| WO | WO-2009/053038 A3 | 4/2009 |
| WO | WO-2009/058812 A1 | 5/2009 |
| WO | WO-2009/080541 A1 | 7/2009 |
| WO | WO-2009/085765 A1 | 7/2009 |
| WO | WO-2009/086072 A2 | 7/2009 |
| WO | WO-2009/086072 A3 | 7/2009 |
| WO | WO-2009/118142 A1 | 10/2009 |
| WO | WO-2009/134738 A1 | 11/2009 |
| WO | WO-2010/033587 A2 | 3/2010 |
| WO | WO-2010/033587 A3 | 3/2010 |
| WO | WO-2010/057107 A1 | 5/2010 |
| WO | WO-2010/057109 A1 | 5/2010 |
| WO | WO-2010/115554 A1 | 10/2010 |
| WO | WO-2011/131749 A1 | 10/2011 |
| WO | WO-2012/018771 A1 | 2/2012 |

(56) References Cited

FOREIGN PATENT DOCUMENTS

| WO | WO-2012/022747 A1 | 2/2012 |
|---|---|---|
| WO | WO-2012/118750 A2 | 9/2012 |
| WO | WO-2012/118750 A3 | 9/2012 |
| WO | WO-2014/039855 A1 | 3/2014 |

OTHER PUBLICATIONS

MacCallum et al., "Antibody-antigen Interactions: Contact Analysis and Binding Site Topography", J. Mol. Biol. (1996) 262, 732-745.*
Anderson, et al., "Targeted anti-cancer therapy using rituximab, a chimeric anti-CD20 antibody (IDEC-C2B8) in the treatment of non-Hodgkin's B-cell lymphoma," *Biochemical Society Transactions*, 25(2):705-708, The Biochemical Society, United States (May 1997).
Ratanatharathorn, V., et al., "Anti-CD20 Chimeric Monoclonal Antibody Treatment of Refractory Immune-Mediated Thrombocytopenia in a Patient with Chronic Graft-versus-Host Disease" *Annals of Internal Medicine*, 133(4):275-279, American College of Physicians, United States (2000).
Zecca, M., et al., Anti-CD20 monoclonal antibody for the treatment of severe, immune-mediated, pure red cell aplasia and hemolytic anemia *Blood*, 97(12):3995-3997, The American Society of Hematology, United States (2001).
Ghetie, M.-A., et al., "Homodimerization of tumor-reactive monoclonal antibodies markedly increases their ability to induce growth arrest or apoptosis of tumor cells," *Proc. Natl. Acad. Sci. USA* 94:7509-7514, National Academy of Sciences (1997).
Ghettie, M.-A., et al., "Homodimers but not monomers of Rituxan (chimeric anti-CD20) induce apoptosis in human B-lymphoma cells and synergize with a chemotherapeutic agent and an immunotoxin," *Blood* 97:1392-1398, The American Society of Hematology (2001).
Lesk, A.M., and Chothia, C., "Elbow motion in the immunoglobulins involves a molecular ball-and-socket joint," *Nature* 335:188-190, Nature Publishing Group (1988).
Ludwig, D.L., et al., "Monoclonal antibody therapeutics and apoptosis," *Oncogene* 22:9097-9106, Nature Publishing Group (Dec. 2003).
Mimori, K. et al., "Costimulatory signals distinctively affect CD20- and B-cell-antigen-receptor-mediated apoptosis in Burkitt's lymphoma/leukemia cells," *Leukemia* 17:1164-1174, Nature Publishing Group (Jun. 2003).
Morea, V., et al., "Antibody Modeling: Implications for Engineering and Design," *Methods* 20:267-279, Academic Press (2000).
Anderson, D.C., and Krummen, L., "Recombinant protein expression for therapeutic applications," *Curr. Opin. Biotechnol.* 13:117-123, Elsevier Science Ltd. (Apr. 2002).
Appelbaum, F.R., "Radiolabeled Moncoclonal Antibodies in the Treatment of Non-Hodgkin's Lymphoma," *Hematol./Oncol. Clin. N. Amer.* 5:1013-1025, W.B. Saunders Company (1991).
Borth, N., et al., "Efficient Selection of High-Producing Subclones During Gene Amplification of Recombinant Chinese Hamster Ovary Cells by Flow Cytometry and Cell Sorting," *Biotechnol. Bioeng.* 71:266-273, John Wiley & Sons, Inc. (2001).
Bowie, J.U., et al., "Deciphering the Message in Protein Sequences: Tolerance to Amino Acid Substitutions," *Science* 247:1306-1310, American Association for the Advancement of Science (1990).
Carter, P., et al., "Humanization of an anti-p185$^{HER2}$ antibody for human cancer therapy," *Proc. Natl. Acad. Sci. USA* 89:4285-4289, The National Academy of Sciences (1992).
Cartron, G., et al., "Therapeutic activity of humanized anti-CD20 monoclonal antibody and polymorphism in IgG Fc receptor FcγRIIIa gene," *Blood* 99:754-758, The American Society of Hematology (Feb. 2002).
Chadd, H.E., and Chamow, S.M., "Therapeutic antibody expression technology," *Curr. Opin. Biotechnol.* 12:188-194, Elsevier Science Ltd. (2001).
Chan, H.T.C., et al., "CD20-induced Lymphoma Cell Death Is Independent of Both Caspases and Its Redistribution into Triton X-100 Insoluble Membrane Rafts," *Cancer Res.* 63:5480-5489, The American Association for Cancer Research (Sep. 2003).

Chothia, C., and Lesk, A.M., Canonical Structures for the Hypervariable Regions of Immunoglobulins, *J. Mol. Biol.* 196:901-917, Academic Press Ltd. (1987).
Chothia, C., et al., "Structural Repertoire of the Human $V_H$ Segments," *J. Mol. Biol.* 227:799-817, Academic Press Ltd. (1992).
Clynes, R.A., et al., "Inhibitory Fc receptors modulate in vivo cytotoxicity against tumor targets," *Nature Med.* 6:443-446, Nature America, Inc. (2000).
Cragg, M., et al., "Complement-mediated lysis by anti-CD20 mAb correlates with segregation into lipid rafts," *Blood* 101:1045-1052, The American Society of Hematology (Feb. 2003).
Cragg, M.S., and Glennie, M.J., "Antibody specificity controls in vivo effector mechanisms of anti-CD20 reagents," *Blood* 103:2738-2743, American Society of Hematology (Apr. 2004).
Cumming, D.A., "Glycosylation of recombinant protein therapeutics: control and functional implications," *Glycobiology* 1:115-130, Oxford University Press (1991).
Davies, J., et al., "Expression of GnTIII in a Recombinant Anti-CD20 CHO Production Cell Line: Expression of Antibodies with Altered Glycoforms Leads to an Increase in ADCC Through Higher Affinity for FcγRIII," *Biotechnol. Bioeng.* 74:288-294, John Wiley & Sons, Inc. (2001).
Deo, Y.M., et al., "Clinical significance of IgG Fc receptors and FcγR-directed immunotherapies," *Immunol. Today* 18:127-135, Elsevier Science Ltd. (1997).
Dillman, R.O., "Magic Bullets at Last! Finally—Approval of a Monoclonal Antibody for the Treatment of Cancer!!!," *Cancer Biother. Radiopharm.* 12:223-225, Mary Ann Liebert, Inc. (1997).
Eary, J.F., et al., "Imaging and Treatment of B-Cell Lymphoma," *J. Nucl. Med.* 31:1257-1268, The Society of Nuclear Medicine, Inc. (1990).
Fischer, D., et al., "Assigning amino acid sequences to 3-dimensional protein folds," *FASEB J.* 10:126-136, FASEB (1996).
Frost, J.D., et al., "A Phase I/IB Trial of Murine Monoclonal Anti-GD2 Antibody 14.G2a plus Interleukin-2 in Children with Refractory Neuroblastoma," *Cancer* 80:317-333, John Wiley & Sons, Inc. (1997).
Giddings, G., "Transgenic plants as protein factories," *Curr. Opin. Biotechnol.* 12:450-454, Elsevier Science Ltd. (2001).
Goldenberg, D.M., et al., "Targeting, Dosimetry, and Radioimmunotherapy of B-Cell Lymphomas With Iodine-131-Labeled LL2 Monoclonal Antibody," *J. Clin. Oncol.* 9:548-564, American Society of Clinical Oncology (1991).
Goldenberg, M.M., "Trastuzumab, a Recombinant DNA-Derived Humanized Monoclonal Antibody, a Novel Agent for the Treatment of Metastatic Breast Cancer," *Clin. Ther.* 21:309-318, Excerpta Medica, Inc. (1999).
Grillo-Lopez, A.-J., et al., "Overview of the Clinical Development of Rituximab: First Monoclonal Antibody Approved for the Treatment of Lymphoma," *Semin. Oncol.* 26(Suppl. 14):66-73, W.B. Saunders Company (1999).
Jefferis, R., et al., "IgG-Fc-mediated effector functions: molecular definition of interaction sites for effector ligands and the role of glycosylation," *Immunol. Rev.* 163:59-76, Munksgaard (1998).
Jenkins, N., et al., "Getting the glycosylation right: Implications for the biotechnology industry," *Nature Biotechnol.* 14:975-981, Nature Publishing Company (1996).
Jones, P.T., et al., "Replacing the complementarity-determining regions in a human antibody with those from a mouse," *Nature* 321:522-525, MacMillan Journals Ltd. (1986).
Kabat, E.A., et al., *Sequences of Proteins of Immunological Interest*, U.S. Department of Health and Human Services, Public Health Services, National Institutes of Health, pp. i-xx (1983).
Kalergis, A. and Ravetch, J.A., "Inducing Tumor Immunity through the Selective Engagement of Activating Fcγ Receptors on Dendritic Cells," *J. Exp. Med.* 195:1653-1659, The Rockefeller University Press (Jun. 2002).
Kaminski, M.S., et al., "Radioimmunotherapy of B-Cell Lymphoma with [$^{131}$I]Anti-B1 (Anti-CD20) Antibody," *New Engl. J. Med.* 329:459-465, Massachusetts Medical Society (1993).

(56) References Cited

OTHER PUBLICATIONS

Lifely, M.R., et al., "Glycosylation and biological activity of CAMPATH-1H expressed in different cell lines and grown under different culture conditions," *Glycobiology* 5:813-822, Oxford University Press (1995).

Liu, A.Y., et al, "Production of a Mouse-Human Chimeric Monoclonal Antibody to CD20 with Potent Fc-Dependent Biologic Activity," *J. Immunol.* 139:3521-3526, The American Association of Immunologists (1987).

Lund, J., et al., "Multiple Interactions of IgG with Its Core Oligosaccharide Can Modulate Recognition by Complement and Human Fcγ Receptor I and Influence the Synthesis of Its Oligosaccharide Chains," *J. Immunol.* 157:4963-4969, The American Association of Immunologists (1996).

Maloney, D.G., et al., "The Anti-Humor Effect of Monoclonal Anti-CD20 Antibody (mAb) Therapy Includes Direct Anti-Proliferative Activity and Induction of Apoptosis in CD20 in Positive Non-Hodgkin's Lymphoma (NHL) Cell Lines," *Blood* 88: 637a, American Society of Hematology, Abstract No. 2535 (1996).

Morrison, S., and Oi, V.T., "Genetically Engineered Antibody Molecules," *Adv. Immunol.* 44:65-92, Academic Press, Inc. (1989).

Morrison, S., et al., "Chimeric human antibody molecules: Mouse antigen-binding domains with human constant region domains," *Proc. Natl. Acad. Sci. USA* 81:6851-6855, The National Academy of Sciences (1984).

Padlan, E.A., "A Possible Procedure for Reducing the Immunogenicity of Antibody Variable Domains While Preserving Their Ligand-Binding Properties," *Mol. Immunol.* 28:489-498, Pergamon Press plc (1991).

Padlan, E.A., "Anatomy of the Antibody Molecule," *Mol. Immunol.* 31:169-217, Elsevier Science Ltd. (1994).

Padlan, E.A., et al., "Identification of specificity-determining residues in antibodies," *FASEB J.* 9:133-139, Federation of American Societies for Experimental Biology (1995).

Polyak, M.J., and Deans, J.P., "Alanine-170 and proline-172 are critical determinants for extracellular CD20 epitopes; heterogeneity in the fine specificity of CD20 monoclonal antibodies is defined by additional requirements imposed by both amino acid sequence and quaternary structure," *Blood* 99:3256-3262, The American Society of Hematology (May 2002).

Poppema, S. and Visser, L., Preparation and Application of Monoclonal Anitbodies: B Cell Panel and Paraffin Tissue Reactive Panel, *Biotest Bull.* 3:131-139 , Birmingham, West Midlands, England (1987).

Press, O.W., et al., "Monoclonal Antibody IF5 (Anti-CD20) Serotherapy of Human B Cell Lymphomas," *Blood* 69:584-591, Grune & Stratton, Inc. (1987).

Press, O.W., et al., "Radiolabeled-Antibody Therapy of B-Cell Lymhoma with Autologous Bone Marrow Support," *New Engl. J. Med.* 329:1219-1224, Massachusetts Medical Society (1993).

Press, O.W., et al., "Treatment of Refractory Non-Hodgkin's Lymphoma With Radiolabeled MB-1 (Anti-CD37) Antibody," *J. Clin. Oncol.* 7:1027-1038, W.B. Saunders Company (1989).

Presta, L.G., et al., "Humanization of an Antibody Directed Against IgE.," *J. Immunol.* 151:2623-2632, The American Association of Immunologists (1993).

Reff, M.E., et al., "Depletion of B Cells In Vivo by a Chimeric Mouse Human Monoclonal Antibody to CD20," *Blood* 83:435-445, The American Society of Hematology (1994).

Riechmann, L., et al., "Reshaping human antibodies for therapy," *Nature* 332:323-327, MacMillan Magazines Ltd. (1988).

Schachter, H., "Biosynthetic controls that determine the branching and microheterogeneity of protein-bound oligosaccharides," *Biochem. Cell Biol.* 64:163-181, The National Research Council of Canada (1986).

Sims, M., et al., "A Humanized CD18 Antibody Can Block Function without Cell Destruction," *J. Immunol.* 151:2296-2308, The American Association of Immunologists (1993).

Surfus, J.E., et al., "Anti-Renal-Cell Carcinoma Chimeric Antibody G250 Facilitates Antibody-Dependent Cellular Cytotoxicity with In Vitro and In Vivo Interleukin-2-Activated Effectors," *J. Immunother.* 19:184-191, Liipincott-Raven Publishers (1996).

Tamura, M., et al., "Structural Correlates of an Anticarcinoma Antibody: Identification of Specificity-Determining Residues (SDRs) and Development of a Minimally Immunogenic Antibody Variant by Retention of SDRs Only," *J. Immunol.* 164:1432-1441, The American Association of Immunologists (2000).

Teeling, J.L., et al., "Characterization of new human CD20 monoclonal antibodies with potent cytolytic activity against non-Hodgkin lymphomas," *Blood* 104:1793-1800, The American Society of Hematology (Sep. 2004).

Umaña, P., et al., "Engineered glycoforms of an antineuroblastoma IgG1 with optimized antibody dependent cellular cytotoxic activity," *Nature Biotechnol.* 17:176-180, Nature America, Inc. (1999).

Verhoeyen, M., et al., "Reshaping Human Antibodies: Grafting an Antilysozyme Activity," *Science* 239:1534-1536, American Association for the Advancement of Science (1988).

Vitetta, E.S., et al., "Redesigning Nature's Poisons to Create Anti-Tumor Reagents," *Science* 238:1098-1104, American Association for the Advancement of Science (1987).

Werner, R.G., et al., "Appropriate Mammalian Expression Systems for Biopharmaceuticals," *Arzneim.-Forsch./Drug Res.* 48:870-880, Aulendorf, Editio Cantor (1998).

Wormald, M.R., et al., "Variations in Oligosaccharide—Protein Interactions in Immunoglobulin G Determine the Site-Specific Glycosylation Profiles and Modulate the Dynamic Motion of the Fc Oligosaccharides," *Biochem.* 36:1370-1380, American Chemical Society (1997).

Wright, A. and Morrison, S.L., "Effect of glycosylation on antibody function: implications for genetic engineering," *Trends Biotechnol.* 15:26-32, Elsevier Trends Journals (1997).

Wu, H., et al., "Humanization of a Murine Monoclonal Antibody by Simultaneous Optimization of Framework and CDR Residues," *J. Mol. Biol.* 294:151-162, Academic Press (1999).

U.S. Appl. No. 12/395,547, filed Feb. 27, 2009, "Combination Therapy for Treatment of Autoimmune Diseases Using B cell Depleting/Immunoregulatory Antibody Combination," for inventor(s) Hanna et al.

International Search Report mailed on Dec. 12, 2007, for PCT Application No. PCT/IB2006/003294, Glycart Biotechnology Ag, inventor(s) Pablo Umaña, Ekkehard Mössner, "Modified Antigen Binding Molecules With Altered Cell Signaling Activity," internationally filed on Aug. 25, 2006, 7 pages.

International Search Report mailed on Jun. 13, 2005, for PCT Application No. PCT/IB2004/003896, Glycart Biotechnology Ag, inventor(s) Pablo Umaña, Peter Brünker, Claudia Ferrara, Tobias Suter, Ursual Pünterner, Ekkehard Mössner, , "CD20 Antibodies With Increased FC Receptor Binding, Affinity and Effector Function," internationally filed on Nov. 5, 2004, 7 pages.

V Base. (2007). "Sequence alignments," MRC Centre for Protein Engineering , located at <http://vbase.mrc-cpe.cam.ac.uk/alignments2.php>, last visited on Jul. 10, 2007, 38 pages.

Non-Final Office Action mailed on Oct. 4, 2007, for U.S. Appl. No. 10/981,738, "Antigen Binding Molecules With Increased FC Receptor Binding Affinity and Effector Function," Umaña et al., filed on Nov. 5, 2004, 8 pages.

Corti, A., et al., "Idiotope Determining Regions of a Mouse Monoclonal Antibody and Its Humanized Versions. Identification of Framework Residues that Affect Idiotype Expression," *J. Mol. Biol.* 235:53-60, Academic Press Ltd., United States (1994).

Hudson, P. and Souriau, C., "Engineered antibodies," *Nature Med.* 9(1):129-134, Nature Publishing Group, United States (2003).

Jazirehi, A. and Bonavida, B., "Cellular and molecular signal transduction pathways modulated by rituximab (rituxan, anti-CD20 mAb) in non-Hodgkin's lymphoma: implications in chemosensitization and therapeutic intervention," *Oncogene* 24:2121-2143, Nature Publishing Group, United Kingdom (Mar. 2005).

Mateo, V., et al., "Mechanisms of CD47-induced caspase-independent cell death in normal and leukemic cells: link between phosphatidylserine exposure and cytoskeleton organization," Blood 100(8):2882-2890, The American Society of Hematology, United States (2002).

(56) References Cited

OTHER PUBLICATIONS

Cerisano, V., et al., "Molecular mechanisms of CD99-induced caspase-independent cell death and cell-cell adhesion in Ewing's sarcoma cells: actin and zyxin as key intracellular mediators," *Oncogene* 23:5664-5674, Nature Publishing Group, England (Jul. 2004).

Fan, Z.-C., et al., "Comparison of the three-dimensional structures of a humanized and a chimeric Fab of an anti-γ-interferon antibody," *J. Mol. Recognit.* 12:19-32, John Wiley & Sons, Ltd., England (1999).

Hahn, M.-J., et al., "Differential activation of MAP kinase family members triggered by CD99 engagement," *FEBS Lett.* 470:350-354, Federation of European Biochemical Societies, Netherlands (2000).

Landolfi, N.F., et al., "The Integrity of the Ball-and-Socket Joint Between V and C Domains Is Essential for Complete Activity of a Humanized Antibody," *J. Immunol.* 166:1748-1754, The American Association of Immunologists, United States (2001).

Neshat, M.N., et al., "Mapping the B cell superantigen binding site for HIV-1 gp120 on a $V_H3$ Ig," *Intl. Immunol.* 12(3):305-312, The Japanese Society for Immunology, Japan (2000).

Pettersen, R.D., et al., "CD99 Signals Caspase-Independent T Cell Death," *J. Immunol.* 166:4931-4942, The American Association of Immunologists, United States (2001).

Potter, K.N., et al., "Evidence for Involvement of a Hydrophobic Patch in Framework Region 1 of Human V4-34-Encoded Igs in Recognition of the Red Blood Cell I Antigen," *J. Immunol.* 169:3777-3782, The American Association of Immunologists, Inc., United States (2002).

Ross, G.M. "Induction of cell death by radiotherapy," *Endocrine-Related Cancer* 6:41-44, Society for Endocrinology, England (1999).

V Base, "Sequence alignments," MRC Centre for Protein Engineering, 58 pages, published 1997 (accessed Jul. 10, 2007) accessed online at <http://vbase.mrc-cpe.cam.ac.uk/alignments2.php>.

International Search Report for International Patent Application No. PCT/IB2004/003896, inventors Umaña et al., "Antigen Binding Molecules with Increased Fc Receptor Binding Affinity and Effector Function," filed Nov. 5, 2004, from the European Patent Office, Netherlands, mailed on Jun. 13, 2005.

Office Action mailed Oct. 4, 2007, in U.S. Appl. No. 10/981,738, "Antigen Binding Molecules with Increased Fc Receptor Binding Affinity and Effector Function," inventors Umaña et al., filed Nov. 5, 2004.

Office Action mailed Jun. 28, 2012 in U.S. Appl. No. 11/509,842, "Modified Antigen Binding Molecules with Altered Cell Signaling Activity," inventors Umaña et al., filed Aug. 25, 2006 (now abandoned).

Co-pending U.S. Appl. No. 13/728,211, filed Dec. 27, 2012, "Modified Antigen Binding Molecules with Altered Cell Signaling Activity," inventors Umaña et al. (not yet published).

Casset et al. "A Peptide Mimetic of Anti-CD4 Monoclonal Antibody by Rational Design," *Biochem. Biophys. Res. Commun.* 307(1):198-205, (Jul. 18, 2003).

Chen et al. "Selection and Analysis of an Optimized Anti-VEGF Antibody; Crystal Structure of an Affinity-Matured Fab in Complex With Antigen," *J. Mol. Biol.* 293(4):865-881, (Nov. 5, 1999).

Foran et al. "European Phase II Study of Rituximab (Chimeric Anti-CD20 Monoclonal Antibody) for Patients with Newly Diagnosed Mantle-Cell Lymphoma and Previously Treated Mantle-Cell Lymphoma, Immunocytoma, and Small B-Cell Lymphocytic Lymphoma," *Journal of Clinical Oncology* 18(2):317-324, (Jan. 2000).

Gao-Uozumi et al. "A Novel Carbohydrate Binding Activity of Annexin V Toward a Bisecting N-Acetylglucosamine," *Glyocobiology* 10(11):1209-1216, (2000).

Holm et al. "Functional Mapping and Single Chain Construction of the Anti-Cytokeratin 8 Monoclonal Antibody TS1," *Mol. Immunol.* 44(6):1075-1084, (Feb. 2007, e-pub. Sep. 20, 2006).

Vajdos et al. "Comprehensive Functional Maps of the Antigen-Binding Site of an Anti-ErbB2 Antibody Obtained With Shotgun Scanning Mutagenesis," *J. Mol. Biol.* 320(2):415-428, (Jul. 5, 2002).

U.S. Appl. No. 14/020,761, filed Sep. 6, 2013, "Combination Therapy of a Type II Anti-CD-20 Antibody With a Selective BCL-2 Inhibitor," for inventor Sampath et al.

U.S. Appl. No. 14/028,207, filed Sep. 16, 2013, "Modified antigen binding molecules with altered cell signaling activity" for inventor Umana et al.

\* cited by examiner

Linker | Start of SEQ ID NO:1 (amino acid) and SEQ ID NO:2 (nucleotide)

```
  1 GAGGTCAAGC TGCAGCAGTC TGGACCTGAA CTGGTGAAGC CTGGGGCCTC AGTGAAGATT TCCTGCAAAG CTTCTGGCTA CGCATTCAGT TACTCTTGGA
    CTCCAGTTCG ACGTCGTCAG ACCTGGACTT GACCACTTCG GACCCCGGAG TCACTTCTAA AGGACGTTTC GAAGACCGAT GCGTAAGTCA ATGAGAACCT
     E  V  K  L  Q  Q  S  G  P  E  L  V  K  P  G  A  S  V  K  I  S  C  K  A  S  G  Y  A  F  S  Y  S  W
    >>.........................B-Ly1 vh..............................................................>

101 TGAACTGGGT GAAACTGAGG CCTGGACAGG GTCTTGAGTG GATTGGACGG ATTTTTCCTG GAGATGGGGA TACTGACTAC AATGGGAAAT TCAAGGGCAA
    ACTTGACCCA CTTTGACTCC GGACCTGTCC CAGAACTCAC CTAACCTGCC TAAAAGGAC CTCTACCCCT ATGACTGATG TTACCCTTTA AGTTCCCGTT
     M  N  W  V  K  L  R  P  G  Q  G  L  E  W  I  G  R  I  F  P  G  D  G  D  T  D  Y  N  G  K  F  K  G
    >.......................................B-Ly1 vh.................................................>

201 GGCCACACTG ACTGCTGACA AATCCTCCAA CACAGCCTAC ATGCAACTG CTCTGTGGAC CCAGCCTGAC CTCTGTGGAC TCTGCGGTCT ATTTATGTGC AAGAAATGTC
    CCGGTGTGAC TGACGACTGT TTAGGAGGTT GTGTCGGATG TACGTTGAC GAGACACCTG GGTCGGACTG GAGACACCTG AGACGCCAGA TAAATACACG TTCTTTACAG
     A  T  L  T  A  D  K  S  S  N  T  A  Y  M  Q  L  T  S  L  T  S  V  D  S  A  V  Y  L  C  A  R  N  V
    >.......................................B-Ly1 vh.................................................>

301 TTTGATGGTT ACTGGTTAGT TTACTGGGC CAAGGGACTC TGGTCACTGT CTCTGCA
    AAACTACCAA TGACCAATCA AATGACCCCG GTTCCCTGAG ACCAGTGACA GAGACGT
     F  D  G  Y  W  L  V  Y  W  G  Q  G  T  L  V  T  V  S  A
    >.......................B-Ly1 vh.................>>
```

FIG. 1

Linker | Start of SEQ ID NO:3 (amino acid) and SEQ ID NO:4 (nucleotide)

```
         HphI                                                                                    MsiI
1   GACATTGTGC TCACCCAAAC TACA|AATCCA GTCACTCTTG GAACATCAGC TTCCATCTCC TGCAGGTCTA GTAAGAGTCT CCTACATAGT AATGGCATCA
    CTGTAACACG AGTGGGTTTG ATGT TTAGGT CAGTGAGAAC CTTGTAGTCG AAGGTAGAGG ACGTCCAGAT CATTCTCAGA GGATGTATCA TTACCGTAGT
    D  I  V    L  T  Q    T     N  P    V  T  L    G  T  S    A  S  I  S    C  R  S    S  K  S     L  L  H  S    N  G  I
    >>.........B-Ly1 v.1..................................................................................>

BseRI                                     MmeI
101 CTTATTTGTA TTGGTATCTG CAGAAGCCAG GCCAGTCTCC TCAGCTCCTG ATTTATCAGA TGTCCAACCT TGTCTCAGGA GTCCCAGACA GGTTCAGTAG
    GAATAAACAT AACCATAGAC GTCTTCGGTC CGGTCAGAGG AGTCGAGGAC TAAATAGTCT ACAGGTTGGA ACAGAGTCCT CAGGGTCTGT CCAAGTCATC
    T  Y  L    Y  W  Y  L    Q  K  P    G  Q  S    P  Q  L  L    I  Y  Q     M  S  N  L    V  S  G    V  P  D    R  F  S
    >.........B-Ly1 v.1..................................................................................>

BtsI                                                                                      AflIII
201 CAGTGGGTCA GGAACTGATT TCACACTGAG AATCAGCAGA GTAGTGTCT TCAGTGGACTC AGGATGTGGG TGTTTATTAC ACAGGAGTTT TCCGTACACG
    GTCACCCAGT CCTTGACTAA AGTGTGACTC TTAGTCGTCT CATCACAGA AGTCACCTGAG TCCTACACCC ACAAATAATG TGTCCTCAAA AGGCATGTGC
    S  G  S    G  T  D    F  T  L    R  I  S  R   V  E  A    E  D  V  G    V  Y  Y    C  A  Q     N  L  E    L  P  Y  T
    >.........B-Ly1 v.1..................................................................................>

301 TTCGAGGGG GGACCAAGCT GGAAATAAAA CGG
    AAGCCTCCCC CCTGGTTCGA CCTTTATTTT GCC
    F  G  G    G  T  K    L  E  I  K    R
    >.........B-Ly1 v.1.........>>
```

FIG. 2

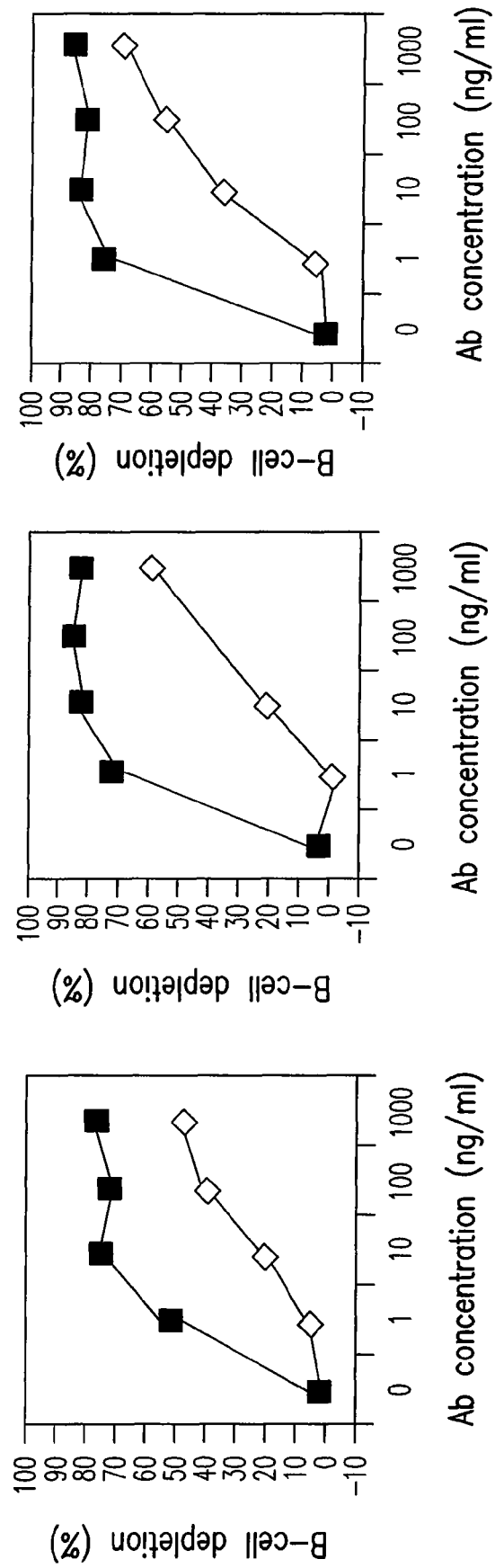

SEQ ID NO: 11 (nucleic acid) and SEQ ID NO: 13 (amino acid)

```
                SqpI                              MluI                                              PstI
  1   ATGGGTTGGA GCCTCATCTT GCTCTTCCTT GTGGCTGTTG CTACCCGTGT CCTGTCCGAG AGCAGTCTGG ACCTGAACTG GTCAAGCCTG
      TACCCAACCT CGGAGTAGAA CGAGAAGGAA CACCGACAAC GATGGCACAG GACAGGCTC TCGTCAGACC TGGACTTGAC CACTTCGGAC
      M  G  W   S  L  I  L   L  F  L    V  A  V    A  T  R  V   L  S  E    S  S  L  D   L  N  W   V  K  P   ........ >    B-Ly1 h.c.
                               HindIII                                                          StuI
 101  GGGCCTGAGT GAAGATTTCC TGCAAAGCTT CTGGCTACGC ATTCAGTTAC TCTTGGATGA ACTGGGTGAA GGACAGGGTC TTGAGTGGAT
      CCCGGACTCA CTTCTAAAGG ACGTTTCGAA GACCGATGCG TAAGTCAATG AGAACCTACT TGACCCACTT CCTGTCCCAG AACTCACCTA
      G  A  S    V  K  I  S   C  K  A    S  G  Y    A  F  S  Y   S  W  M    N  W  V  K   L  R  P   G  Q  G   L  E  W   ........ >    B-Ly1 h.c.
 201  TGGACGGATT TTTCCTGGAG ATGGGGATAC TGACTACAAT GGGAAATTCA AGGGCAAGGC CACACTGACT GCTGACAAAT CCTCCAACATG
      ACCTGCCTAA AAAGGACCTC TACCCCTATG ACTGATGTTA CCCTTTAAGT TCCCGTTCCG GTGTGACTGA CGACTGTTTA GGAGGTTGTG
      I  G  R  I   F  P  G   D  G  D    T  D  Y  N   G  K  F    K  G  K  A   T  L  T    A  D  K  S   S  N    AGCCTACATG  TCGGATGTAC   ........ >    B-Ly1 h.c.
                                                                                                      PshAI
 301  CAACTCACCA GCCTGACCTC TGTGGACTCT TGGGGTCTATT TATGTGCAAG AAATGTCTTT GATGGTTACT GGTTAGTTTA CTGGGGCCAA GGGACTCTGG
      GTTGAGTGGT CGGACTGGAG ACACCTGAGA CCCCAGATAA ATACACGTTC TTTACAGAAA CTACCAATGA CCAATCAAAT GACCCCGGTT CCCTGAGACC
      Q  L  T    S  L  T    S  V  D  S   A  V  Y    L  C  A  R   N  V  F    D  G  Y   W  L  V    Y  W  G  Q   G  T  L   ........ >    B-Ly1 h.c.
         PstI                              NheI
 401  TCACTGTCTC TGCAGCTAGC ACCAAGGGCC CATCGGTCTT CCCCCTGGCA CCCTCCTCCA AGAGCACCTC TGGGGGCACA GCGGCCCTGG GCTGCCTGGT
      AGTGACAGAG ACGTCGATCG TGGTTCCCGG GTAGCCAGAA GGGGGACCGT GGGAGGAGGT TCTCGTGGAG ACCCCCGTGT CGCCGGGACC CGACGGACCA
      V  T  V    S  A  A  S   T  K  G   P  S  V    F  P  L  A   P  S  S    K  S  T    S  G  G  T   A  A  L   G  C  L   ........ >    B-Ly1 h.c.
```

```
                                                        SEQ ID NO: 11
                                                        (nucleic acid)
                                                        and
                                                        SEQ ID NO: 13
                                                        (amino acid)

SmaI
         ---+---
1101  ACAGGTGTAC ACCCTGCCCC CATCCCGGGA TGAGCTGACC AAGAACCAGG TCAGCCTGAC CTGCCTGGTC AAAGGCTTCT ATCCCAGCGA CATCGCCCTG
      TGTCCACATG TGGGACGGGG GTAGGGCCCT ACTCGACTGG TTCTTGGTCC AGTCGGACTG GACGGACCAG TTTCCGAAGA TAGGGTCGCT GTAGCGGGAC
      P Q V Y   T L P   P S R   D E L T   K N Q   V S L T   C L V   K G F   Y P S   D I A V
      >.........B-Ly1 h.c............................................................................>

1201  GAGTGGGAGA GCAATGGGCA GCCGGAGAAC AACTACAAGA CCACGCCTCC CGTGCTGGAC TCCGACGGCT CCTTCTTCCT CTACAGCAAG CTCACCGTGG
      CTCACCCTCT CGTTACCCGT CGGCCTCTTG TTGATGTTCT GGTGCGGAGG GCACGACCTG AGGCTGCCGA GGAAGAAGGA GATGTCGTTC GAGTGGCACC
      E W E   S N G   Q P E N   N Y K   T T P   P V L D   S D G   S F F   L Y S K   L T V
      >.........B-Ly1 h.c............................................................................>

SapI
                                                                                 ---
1301  ACAAGAGCAG GTGGCAGCAG GGGAACGTCT TCTCATGCTC CGTGATGCAT GAGGCTCTGC ACAACCACTA CACGCAGAAG AGCCTCTCCC TGTCTCCGGG
      TGTTCTCGTC CACCGTCGTC CCCTTGCAGA AGAGTACGAG GCACTACGTA CTCCGAGACG TGTTGGTGAT GTGCGTCTTC TCGGAGAGGG ACAGAGGCCC
      D K S   R W Q Q   G N V   F S C   S V M H   E A L   H N H   Y T Q K   S L S   L S P
      >.........B-Ly1 h.c............................................................................>

1401  TAAATGA
      ATTTACT
      G K -
      >.....>> B-Ly1 h.c.
```

FIG.5C

SEQ ID NO: 12 (nucleic acid) and
SEQ ID NO: 14 (amino acid)

```
  1  ATGGATTTTC AGGTGCAGAT TATCAGCTTC CTGCTAATCA GTGCTTCAGT CATAATGTCC AGAGGAGACA TTGTGCTCAC CCAAACTACA AATCCAGTCA
     TACCTAAAAG TCCACGTCTA ATAGTCGAAG GACGATTAGT CACGAAGTCA GTATTACAGG TCTCCTCTGT AACACGAGTG GGTTTGATGT TTAGGTCAGT
        M  D  F  Q  V  Q  I  I  S  F  L  L  I  S  A  S  V  I  M  S  R  G  D  I  V  L  T  Q  T  T  N  P  V >>.......B-Ly1 l.c.
                                                                                         PstI

101  CTCTTGGAAC ATCAGCTTCC ATCTCCTGCA GGTCTAGTAA GAGTCTCCTA CATAGTAATG GCATCACTTA TTTGTATTGG AACATAACC AGCCAGGCCA
     GAGAACCTTG TAGTCGAAGG TAGAGGACGT CCAGATCATT CTCAGAGGAT GTATCATTAC CGTAGTGAAT AAACATAACC TTGTATTGG TCGGTCCGGT
        L  G  T  S  A  S  I  S  C  R  S  S  K  S  L  L  H  S  N  G  I  T  Y  L  Y  W  Y  L  Q  K  P  G >.......B-Ly1 l.c.
                       PstI                                                             XbaI

201  GTCTCCTCAG CTCCTGATTT ATCAGATGTC CAACCTTGTC TCAGGAGTCC CAGATAGGTT CAGTAGCAGT GGGTCAGGAA CTGATTTCAC ACTGAGAATC
     CAGAGGAGTC GAGGACTAAA TAGTCTACAG GTTGGAACAG AGTCCTCAGG GTCATCCAA GTCATCGTCA CCCAGTCCTT GACTAAAGTG TGACTCTTAG
        S  P  Q  L  L  I  Y  Q  M  S  N  L  V  S  G  V  P  D  R  F  S  S  S  G  S  G  T  D  F  T  L  R  I >.......B-Ly1 l.c.
                                                                                                                BsiWI

301  AGCAGAGTGG AGGCTGAGGA TGTGGGGTGT TATTACTGTG CACAATATTA CTGTCAAAAATCT AGAACTTCCG CTCAAAAATCT GAGTTTTTAGA TCTTTGCAT
     TCGTCTCACC TCCGACTCCT ACACCCCACA ATAATGACAC ATAATGAAAG ATCAAGCTT CCATAGATGA AAGGTCAACA CCTTCTGAAT GACAGGTTT GAAAAACGTA
        S  R  V  E  A  E  D  V  G  V  Y  Y  C  A  Q  N  L  E  L  P  Y  T  F  G  G  G  T  K  L  E  I  K  R >.......B-Ly1 l.c.
                                                                                                             XmnI

401  CGGTGGCTGC ACCATCTGTC TTCATCTTCC CGCCATCTGA TGAGCAGTTG AAATCTGGAA CTGCCTCTGT TGTGTGCCTG CTGAATAACT TCTATCCCAG
     GCCACCGACG TGGTAGACAG AAGTAGAAGG GCGGTAGACT ACTCGTCAAC TTTAGACCTT GACGGAGACA ACACACGGAC GACTTATTGA AGATAGGGTC
        T  V  A  A  P  S  V  F  I  F  P  P  S  D  E  Q  L  K  S  G  T  A  S  V  V  C  L  L  N  N  F  Y  P >.......B-Ly1 l.c.

501  AGAGGCCAAA GTACAGTGGA AGGTGGATAA CGCCCTCCAA TCGGGTAACT CCCAGGAGAG TGTCACAGAG CAGGACAGCA AGGACAGCAC CTACAGCCTC
     TCTCCGGTTT CATGTCACCT TCCACCTATT GCGGGAGGTT AGCCCATTGA GGGTCCTCTC ACAGTGTCTC GTCCTGTCGT TCCTGTCGTG GATGTCGGAG
        R  E  A  K  V  Q  W  K  V  D  N  A  L  Q  S  G  N  S  Q  E  S  V  T  E  Q  D  S  K  D  S  T  Y  S  L >.......B-Ly1 l.c.
```

FIG.6A

```
601 AGCAGCACCC TGAGCTGAGC CAAAGCAGAC TACGAGAAAC ACAAAGTCTA CGCCTGCGAA GTCACCCATC AGGGCCTGAG CTCGCCCGTC ACAAAGAGCT
    TCGTCGTGGG ACTGCGACTC GTTTCGTCTG ATGCTCTTTG TGTTTCAGAT GCGGACGCTT CAGTGGGTAG TCCCGGACTC GAGCGGGCAG TGTTTCTCGA
     S  S  T  L  T  L  S  K  A  D  Y  E  K  H  K  V  Y  A  C  E  V  T  H  Q  G  L  S  S  P  V  T  K  S
    >......................B-Ly1 l.c....................................................................>

701 TCAACAGGGG AGAGTGTTAG
    AGTTGTCCCC TCTCACAATC
     F  N  R  G  E  C  -
    >....B-Ly1 l.c.....>>
```

SacI
                                        ──┼──

SEQ ID NO: 12 (nucleic acid) and
SEQ ID NO: 14 (amino acid)

FIG.6B

CDR1(Kabat):
TACTCTTGGATGAAC                                              SEQ ID NO: 5
TyrSerTrpMetAsn                                              SEQ ID NO: 15
CDR1(Chothia):
GGCTACGCATTCAGTTAC                                           SEQ ID NO: 6
GlyTyrAlaPheSerTyr                                           SEQ ID NO: 16
CDR1(AbM):
GGCTACGCATTCAGTTACTCTTGGATGAAC                               SEQ ID NO: 7
GlyTyrAlaPheSerTyrSerTrpMetAsn                               SEQ ID NO: 17

CDR2(Kabat):
CGGATTTTTCCTGGAGATGGGGATACTGACTACAATGGGAAATTCAAGGGC          SEQ ID NO: 21
ArgIlePheProGlyAspGlyAspThrAspTyrAsnGlyLysPheLysGly          SEQ ID NO: 25
CDR2(Chothia):
TTTCCTGGAGATGGGGATACTGAC                                     SEQ ID NO: 22
PheProGlyAspGlyAspThrAsp                                     SEQ ID NO: 26
CDR2(AbM):
CGGATTTTTCCTGGAGATGGGGATACTGAC                               SEQ ID NO: 23
ArgIlePheProGlyAspGlyAspThrAsp                               SEQ ID NO: 27

CDR3(Kabat,Chothia,AbM):
AATGTCTTTGATGGTTACTGGTTAGTTTAC                               SEQ ID NO: 24
AsnValPheAspGlyTyrTrpLeuValTyr                               SEQ ID NO: 28

FIG.7A

CDR1(Kabat):
AGGTCTAGTAAGAGTCTCCTACATAGTAATGGCATCACTTATTTGTAT             SEQ ID NO: 8
ArgSerSerLysSerLeuLeuHisSerAsnGlyIleThrTyrLeuTyr              SEQ ID NO: 18
CDR2(Kabat):
CAGATGTCCAACCTTGTCTCA                                        SEQ ID NO: 9
GlnMetSerAsnLeuValSer                                        SEQ ID NO: 19
CDR3(Kabat):
GCTCAAAATCTAGAACTTCCGTACACG                                  SEQ ID NO: 10
AlaGlnAsnLeuGluLeuProTyrThr                                  SEQ ID NO: 20

FIG.7B

ANTIGEN BINDING MOLECULES WITH INCREASED FC RECEPTOR BINDING AFFINITY AND EFFECTOR FUNCTION

CROSS-REFERENCE TO RELATED APPLICATIONS

This application is a divisional of U.S. Non-Provisional application Ser. No. 10/981,738, filed on Nov. 5, 2004 which claims the benefit of U.S. Provisional Application No. 60/517,096, filed Nov. 5, 2003, the entire contents of which are hereby incorporated by reference.

REFERENCE TO SEQUENCE LISTING SUBMITTED ELECTRONICALLY

The content of the electronically submitted substitute sequence listing, file name: 1975.0290003_substitute_sequence_listing_ascii.txt; Size: 59,280 bytes; and Date of Creation: Mar. 2, 2011, filed herewith, is incorporated by reference in its entirety.

BACKGROUND OF THE INVENTION

1. Field of the Invention

The present invention relates to antigen binding molecules (ABMs). In particular embodiments, the present invention relates to recombinant monoclonal antibodies, including chimeric, primatized or humanized antibodies specific for human CD20. In addition, the present invention relates to nucleic acid molecules encoding such ABMs, and vectors and host cells comprising such nucleic acid molecules. The invention further relates to methods for producing the ABMs of the invention, and to methods of using these ABMs in treatment of disease. In addition, the present invention relates to ABMs with modified glycosylation having improved therapeutic properties, including antibodies with increased Fc receptor binding and increased effector function.

2. Background Art

The Immune System and Anti-CD20 Antibodies

The immune system of vertebrates, including humans, consists of a number of organs and cell types, which have evolved to accurately and specifically recognize, bind and destroy invading foreign microorganisms ("antigens"). Lymphocytes are critical for the proper function of the immune system. These cells are produced in the thymus, spleen and bone marrow (adult) and represent about 30% of the total white blood cells present in the circulatory system of adult humans. There are two major sub-populations of lymphocytes: T cells and B cells. T cells are responsible for cell mediated immunity, while B cells are responsible for antibody production (humoral immunity). However, in a typical immune response, T cells and B cells function interdependently: T cells are activated when the T cell receptor binds to fragments of an antigen that are bound to major histocompatability complex ("MHC") glycoproteins on the surface of an antigen presenting cell; such activation causes release of biological mediators ("interleukins"), which stimulate B cells to differentiate and produce antibodies ("immunoglobulins") against the antigen.

Each B cell within the host expresses an antibody of one particular type and specificity, and different B cells express antibodies specific for different antigens. B cell proliferation and antibody production spike as a reaction to a foreign antigen, and both typically cease (or substantially decrease) once the foreign antigen has been neutralized. Occasionally, however, proliferation of a particular B cell will continue unabated; such proliferation can result in a cancer referred to as "B cell lymphoma."

T cells and B cells both comprise cell surface proteins which can be utilized as "markers" for differentiation and identification. One such human B cell marker is the human B lymphocyte-restricted differentiation antigen Bp35, referred to as "CD20." CD20 is expressed during early pre-B cell development and remains until plasma cell differentiation. Specifically, the CD20 molecule may regulate a step in the activation process that is required for cell cycle initiation and differentiation and is usually expressed at very high levels on neoplastic ("tumor") B cells. Because CD20 is present at high levels on "malignant" B cells, i.e., those B cells whose unabated proliferation can lead to B cell lymphoma, the CD20 surface antigen has the potential of serving as a candidate for "targeting" of B cell lymphomas.

In essence, such targeting can be generalized as follows: antibodies specific to the CD20 surface antigen of B cells are introduced into a patient, by injection, for example. These anti-CD20 antibodies specifically bind to the CD20 cell surface antigen of (ostensibly) both normal and malignant B cells; the anti-CD20 antibody bound to the CD20 surface antigen may lead to the destruction and depletion of neoplastic B cells. Additionally, chemical agents or radioactive labels having the potential to destroy the tumor can be conjugated to the anti-CD20 antibody such that the agent is specifically "delivered" to e.g., the neoplastic B cells. Irrespective of the approach, a primary goal is to destroy the tumor: the specific approach can be determined by the particular anti-CD20 antibody which is utilized and, thus, the available approaches to targeting the CD20 antigen can vary considerably.

Unconjugated monoclonal antibodies (mAbs) can be useful medicines for the treatment of cancer, as demonstrated by the U.S. Food and Drug Administration's approval of Rituximab (Rituxan™; IDEC Pharmaceuticals, San Diego, Calif., and Genentech Inc., San Francisco, Calif.), for the treatment of CD20 positive B-cell, low-grade or follicular Non-Hodgkin's lymphoma, Trastuzumab (Herceptin™; Genentech Inc,) for the treatment of advanced breast cancer (Grillo-Lopez, A.-J., et al., *Semin. Oncol.* 26:66-73 (1999); Goldenberg, M. M., *Clin. Ther.* 21:309-18 (1999)), Gemtuzumab (Mylotarg™, Celltech/Wyeth-Ayerst) for the treatment of relapsed acute myeloid leukemia, and Alemtuzumab (CAMPATH™, Millenium Pharmaceuticals/Schering AG) for the treatment of B cell chronic lymphocytic leukemia. The success of these products relies not only on their efficacy but also on their outstanding safety profiles (Grillo-Lopez, A.-J., et al., *Semin. Oncol.* 26:66-73 (1999); Goldenberg, M. M., *Clin. Ther.* 21:309-18 (1999)). In spite of the achievements of these drugs, there is currently a large interest in obtaining higher specific antibody activity than what is typically afforded by unconjugated mAb therapy. The murine monoclonal antibody, B-Ly1, is another antibody known to be specific to human CD20. (Poppema, S. and Visser, L., *Biotest Bulletin* 3: 131-139 (1987)).

The results of a number of studies suggest that Fc-receptor-dependent mechanisms contribute substantially to the action of cytotoxic antibodies against tumors and indicate that an optimal antibody against tumors would bind preferentially to activation Fc receptors and minimally to the inhibitory partner FcγRIIB. (Clynes, R. A., et al., *Nature Medicine* 6(4):443-446 (2000); Kalergis, A. M., and Ravetch, J. V., *J. Exp. Med.* 195(12):1653-1659 (June 2002). For example, the results of at least one study suggest that the FcγRIIIa receptor in particular is strongly associated with the efficacy of antibody therapy. (Cartron, G., et al., *Blood* 99(3):754-757 (February 2002)). That study showed that patients homozygous for FcγRIIa have a better response to Rituximab than heterozygous patients. The authors concluded that the superior response was due to better in vivo binding of the antibody to FcγRIIIa, which resulted in better ADCC activity against lymphoma cells. (Cartron, G., et al., *Blood* 99(3):754-757 (February 2002)).

Various attempts to target the CD20 surface antigen have been reported. Murine (mouse) monoclonal antibody 1F5 (an anti-CD20 antibody) was reportedly administered by continuous intravenous infusion to B cell lymphoma patients. Extremely high levels (>2 grams) of 1F5 were reportedly required to deplete circulating tumor cells, and the results were described as being "transient." Press et al., "Monoclonal Antibody 1F5 (Anti-CD20) Serotherapy of Human B-Cell Lymphomas." *Blood* 69/2:584-591 (1987). A potential problem with this approach is that non-human monoclonal antibodies (e.g., murine monoclonal antibodies) typically lack human effector functionality, i.e., they are unable to, inter alia, mediate complement dependent lysis or lyse human target cells through antibody dependent cellular toxicity or Fc-receptor mediated phagocytosis. Furthermore, non-human monoclonal antibodies can be recognized by the human host as a foreign protein; therefore, repeated injections of such foreign antibodies can lead to the induction of immune responses leading to harmful hypersensitivity reactions. For murine-based monoclonal antibodies, this is often referred to as a Human Anti-Mouse Antibody response, or "HAMA" response. Additionally, these "foreign" antibodies can be attacked by the immune system of the host such that they are, in effect, neutralized before they reach their target site.

Another reported approach at improving the ability of murine monoclonal antibodies to be effective in the treatment of B-cell disorders has been to conjugate a radioactive label or toxin to the antibody such that the label or toxin is localized at the tumor site. For example, the above-referenced 1F5 antibody has been "labeled" with iodine-131 ("$^{131}$I") and was reportedly evaluated for biodistribution in two patients. See Eary, J. F. et al., "Imaging and Treatment of B-Cell Lymphoma" *J. Nuc. Med.* 31/8:1257-1268 (1990); see also, Press, O. W. et al., "Treatment of Refractory Non-Hodgkin's Lymphoma with Radiolabeled MB-1 (Anti-CD37) Antibody" *J. Clin. Onc.* 7/8:1027-1038 (1989) (indication that one patient treated with $^{131}$I-labeled IF-5 achieved a "partial response"); Goldenberg, D. M. et al., "Targeting, Dosimetry and Radioimmunotherapy of B-Cell Lymphomas with Iodine-131-Labeled LL2 Monoclonal Antibody" *J. Clin. Onc.* 9/4:548-564 (1991) (three of eight patients receiving multiple injections reported to have developed a HAMA response); Appelbaum, F. R. "Radiolabeled Monoclonal Antibodies in the Treatment of Non-Hodgkin's Lymphoma" *Hem./Onc. Clinics of N.A.* 5/5:1013-1025 (1991) (review article); Press, O. W. et al "Radiolabeled-Antibody Therapy of B-Cell Lymphoma with Autologous Bone Marrow Support." *New England J. Med.* 329/17: 1219-12223 (1993) (iodine-±31 labeled anti-CD20 antibody IF5 and B1); and Kaminski, M. G. et al "Radioimmunotherapy of B-Cell Lymphoma with $^{131}$I Anti-B1 (Anti-CD20) Antibody". *New England J. Med.* 329/7 (1993) (iodine-131 labeled anti-CD20 antibody B1; hereinafter "Kaminski"). Toxins (i.e., chemotherapeutic agents such as doxorubicin or mitomycin C) have also been conjugated to antibodies. See, for example, PCT published application WO 92/07466 (published May 14, 1992).

Chimeric antibodies comprising portions of antibodies from two or more different species (e.g., mouse and human) have been developed as an alternative to "conjugated" antibodies. For example, Liu, A. Y. et al, "Production of a Mouse-Human Chimeric Monoclonal Antibody to CD20 with Potent Fc-Dependent Biologic Activity" *J. Immun.* 139/10:3521-3526 (1987), describes a mouse/human chimeric antibody directed against the CD20 antigen. See also, PCT Publication No. WO 88/04936. For example, rituximab (RITUXAN®), a chimeric anti-CD20, antibody has been approved for the treatment of non-Hodgkins lymphoma.

Given the expression of CD20 by B cell lymphomas, this antigen can serve as a candidate for "targeting" of such lymphomas. In essence, such targeting can be generalized as follows: antibodies specific for CD20 surface antigen on B cells are administered to a patient. These anti-CD20 antibodies specifically bind to the CD20 antigen of (ostensibly) both normal and malignant B cells, and the antibody bound to the CD20 on the cell surface results in the destruction and depletion of tumorigenic B cells. Additionally, chemical agents, cytotoxins or radioactive agents may be directly or indirectly attached to the anti-CD20 antibody such that the agent is selectively "delivered" to the CD20 antigen expressing B cells. With both of these approaches, the primary goal is to destroy the tumor. The specific approach will depend upon the particular anti-CD20 antibody that is utilized. Thus, it is apparent that the various approaches for targeting the CD20 antigen can vary considerably.

The rituximab (RITUXAN®) antibody is a genetically engineered chimeric human gamma 1 murine constant domain containing monoclonal antibody directed against the human CD20 antigen. This chimeric antibody contains human gamma 1 constant domains and is identified by the name "C2B8" in U.S. Pat. No. 5,736,137 (Andersen et. al.) issued on Apr. 17, 1998, assigned to IDEC Pharmaceuticals Corporation. RITUXAN® is approved for the treatment of patients with relapsed or refracting low-grade or follicular, CD20 positive, B cell non-Hodgkin's lymphoma. In vitro mechanism of action studies have shown that RITUXAN® exhibits human complement—dependent cytotoxicity (CDC) (Reff et. al, *Blood* 83(2): 435-445 (1994)). Additionally, it exhibits significant activity in assays that measure antibody—dependent cellular cytotoxicity (ADCC). RITUXAN® has been shown to possess anti-proliferative activity in thymidine incorporation assays and a limited ability to induce apoptosis directly, whereas CD20 antibodies do not (Maloney et. al, *Blood* 88 (10): 637a (1996)).

Antibody Glycosylation

The oligosaccharide component can significantly affect properties relevant to the efficacy of a therapeutic glycoprotein, including physical stability, resistance to protease attack, interactions with the immune system, pharmacokinetics, and specific biological activity. Such properties may depend not only on the presence or absence, but also on the specific structures, of oligosaccharides. Some generalizations between oligosaccharide structure and glycoprotein function can be made. For example, certain oligosaccharide structures mediate rapid clearance of the glycoprotein from the bloodstream through interactions with specific carbohydrate binding proteins, while others can be bound by antibodies and trigger undesired immune reactions. (Jenkins et al., *Nature Biotechnol.* 14:975-81 (1996)).

Mammalian cells are the preferred hosts for production of therapeutic glycoproteins, due to their capability to glycosylate proteins in the most compatible form for human application. (Cumming et al., *Glycobiology* 1:115-30 (1991); Jenkins et al., *Nature Biotechnol.* 14:975-81 (1996)). Bacteria very rarely glycosylate proteins, and like other types of common hosts, such as yeasts, filamentous fungi, insect and plant cells, yield glycosylation patterns associated with rapid clearance from the blood stream, undesirable immune interactions, and in some specific cases, reduced biological activity. Among mammalian cells, Chinese hamster ovary (CHO) cells have been most commonly used during the last two decades. In addition to giving suitable glycosylation patterns, these cells allow consistent generation of genetically stable, highly productive clonal cell lines. They can be cultured to high densities in simple bioreactors using serum-free media, and permit the development of safe and reproducible bioprocesses. Other commonly used animal cells include baby hamster kidney (BHK) cells, NS0- and SP2/0-mouse myeloma cells. More recently, production from transgenic animals has also been tested. (Jenkins et al., *Nature Biotechnol.* 14:975-81 (1996)).

All antibodies contain carbohydrate structures at conserved positions in the heavy chain constant regions, with each isotype possessing a distinct array of N-linked carbohydrate structures, which variably affect protein assembly, secretion or functional activity. (Wright, A., and Morrison, S. L., *Trends Biotech.* 15:26-32 (1997)). The structure of the attached N-linked carbohydrate varies considerably, depending on the degree of processing, and can include high-mannose, multiply-branched as well as biantennary complex oligosaccharides. (Wright, A., and Morrison, S. L., *Trends Biotech.* 15:26-32 (1997)). Typically, there is heterogeneous processing of the core oligosaccharide structures attached at a particular glycosylation site such that even monoclonal antibodies exist as multiple glycoforms. Likewise, it has been shown that major differences in antibody glycosylation occur between cell lines, and even minor differences are seen for a given cell line grown under different culture conditions. (Lifely, M. R. et al., *Glycobiology* 5(8):813-22 (1995)).

One way to obtain large increases in potency, while maintaining a simple production process and potentially avoiding significant, undesirable side effects, is to enhance the natural, cell-mediated effector functions of monoclonal antibodies by engineering their oligosaccharide component as described in Umaña, P. et al., *Nature Biotechnol.* 17:176-180 (1999) and U.S. Pat. No. 6,602,684, the entire contents of which are hereby incorporated by reference in their entirety. IgG1 type antibodies, the most commonly used antibodies in cancer immunotherapy, are glycoproteins that have a conserved N-linked glycosylation site at Asn297 in each CH2 domain. The two complex biantennary oligosaccharides attached to Asn297 are buried between the CH2 domains, forming extensive contacts with the polypeptide backbone, and their presence is essential for the antibody to mediate effector functions such as antibody dependent cellular cytotoxicity (ADCC) (Lifely, M. R., et al., *Glycobiology* 5:813-822 (1995); Jefferis, R., et al., *Immunol Rev.* 163:59-76 (1998); Wright, A. and Morrison, S. L., *Trends Biotechnol.* 15:26-32 (1997)).

The present inventors showed previously that overexpression in Chinese hamster ovary (CHO) cells of β(1,4)-N-acetylglucosaminyltransferase III ("GnTIII"), a glycosyltransferase catalyzing the formation of bisected oligosaccharides, significantly increases the in vitro ADCC activity of an anti-neuroblastoma chimeric monoclonal antibody (chCE7) produced by the engineered CHO cells. (See Umaña, P. et al., *Nature Biotechnol.* 17:176-180 (1999); and International Publication No. WO 99/54342, the entire contents of which are hereby incorporated by reference). The antibody chCE7 belongs to a large class of unconjugated mAbs which have high tumor affinity and specificity, but have too little potency to be clinically useful when produced in standard industrial cell lines lacking the GnTIII enzyme (Umana, P., et al., *Nature Biotechnol.* 17:176-180 (1999)). That study was the first to show that large increases of ADCC activity could be obtained by engineering the antibody-producing cells to express GnTIII, which also led to an increase in the proportion of constant region (Fc)-associated, bisected oligosaccharides, including bisected, nonfucosylated oligosaccharides, above the levels found in naturally-occurring antibodies.

There remains a need for enhanced therapeutic approaches targeting the CD20 antigen for the treatment of B cell lymphomas in primates, including, but not limited to, humans.

BRIEF SUMMARY OF THE INVENTION

Recognizing the tremendous therapeutic potential of antigen binding molecules (ABMs) that have the binding specificity of the murine B-Ly1 antibody and that have been glycoengineered to enhance Fc receptor binding affinity and effector function, the present inventors developed a method for producing such ABMs. Inter alia, this method involves producing recombinant, chimeric antibodies or chimeric fragments thereof. The efficacy of these ABMs is further enhanced by engineering the glycosylation profile of the antibody Fc region.

Accordingly, in one aspect, the invention is directed to an isolated polynucleotide comprising: (a) a sequence selected from a group consisting of: SEQ ID NO.:5, SEQ ID NO.: 6 and SEQ ID NO.:7. (CDRs $V_{H-1}$); (b) a sequence selected from a group consisting of: SEQ ID NO.:21, SEQ ID NO.:22 and SEQ ID NO.:23. (CDRs $V_{H-2}$); and SEQ ID NO:24. In another aspect, the invention is directed to an isolated polynucleotide comprising SEQ ID NO.:8, SEQ ID NO.: 9 and SEQ ID NO.:10. (CDRs $V_L$). In one embodiment, any of these polynucleotides encodes a fusion polypeptide.

In a further aspect, the invention is directed to an isolated polynucleotide comprising SEQ ID No.:3 In another aspect, the invention is directed to an isolated polynucleotide comprising SEQ ID No.:4. In a further aspect, the invention is directed to an isolated polynucleotide comprising a sequence selected from the group consisting of SEQ ID No:29; SEQ ID No:31; SEQ ID No:33; SEQ ID No:35; SEQ ID No:37; SEQ ID No:39; SEQ ID No:41; SEQ ID No:43; SEQ ID No:45; SEQ ID No:47; SEQ ID No:49; SEQ ID No:51; SEQ ID No:53; SEQ ID No:55; SEQ ID No:57; SEQ ID No:59; SEQ ID No:61; SEQ ID No:63; SEQ ID No:65; SEQ ID No:67; SEQ ID No:69; and SEQ ID No:71. In another aspect, the invention is directed to an isolated polynucleotide comprising SEQ ID No.:75. In one embodiment, such polynucleotides encode fusion polypeptides.

The invention is further directed to an isolated polynucleotide comprising a sequence having at least 80% identity to SEQ ID NO:3, wherein said isolated polynucleotide encodes a fusion polypeptide. In an additional aspect, the invention is directed to an isolated polynucleotide comprising a sequence having at least 80% identity to SEQ ID NO:4, wherein said isolated polynucleotide encodes a fusion polypeptide. The invention is further directed to an isolated polynucleotide comprising a sequence having at least 80% identity to a sequence selected from the group consisting of SEQ ID No:29; SEQ ID No:31; SEQ ID No:33; SEQ ID No:35; SEQ ID No:37; SEQ ID No:39; SEQ ID No:41; SEQ ID No:43; SEQ ID No:45; SEQ ID No:47; SEQ ID No:49; SEQ ID No: 51; SEQ ID No:53; SEQ ID No:55; SEQ ID No:57; SEQ ID No:59; SEQ ID No:61; SEQ ID No:63; SEQ ID No:65; SEQ ID No:67; SEQ ID No:69; and SEQ ID No:71, wherein said isolated polynucleotide encodes a fusion polypeptide. In an additional aspect, the invention is directed to an isolated polynucleotide comprising a sequence having at least 80% identity to SEQ ID NO:75, wherein said isolated polynucleotide encodes a fusion polypeptide.

The invention is further directed to a polynucleotide comprising SEQ ID NO:11 (whole heavy chain), or to polynucleotides having 80%, 85%, 90%, 95% or 99% identity to SEQ ID NO:11. The invention is also directed to a polynucleotide comprising SEQ ID NO:12 (whole light chain), or to polynucleotides having 80%, 85%, 90%, 95% or 99% identity to SEQ ID NO:12.

The invention is also directed to an isolated polynucleotide encoding a chimeric polypeptide having the sequence of SEQ ID No.:1. In one embodiment, the polynucleotide comprises a sequence encoding a polypeptide having the sequence of SEQ ID No.:1; and a sequence encoding a polypeptide having the sequence of an antibody Fc region, or a fragment thereof, from a species other than mouse. The invention is also directed to an isolated polynucleotide encoding a chimeric polypeptide having a sequence selected from the group consisting of SEQ ID No:30; SEQ ID No:32; SEQ ID No:34; SEQ ID No:36; SEQ ID No:38; SEQ ID No:40; SEQ ID No:42; SEQ ID No:44; SEQ ID No:46; SEQ ID No:48; SEQ ID No:50; SEQ ID No:52; SEQ ID No:54; SEQ ID No:56; SEQ ID No:58; SEQ ID No:60; SEQ ID No:62; SEQ ID No:64; SEQ ID No:66; SEQ ID No:68; SEQ ID No:70; and SEQ ID No:72. In one embodiment, the polynucleotide comprises a sequence encoding a polypeptide having a sequence selected from the group consisting of SEQ ID No:30; SEQ ID No:32; SEQ ID No:34; SEQ ID No:36; SEQ ID No:38; SEQ ID No:40; SEQ ID No:42; SEQ ID No:44; SEQ DI) No:46; SEQ ID No:48; SEQ ID No:50; SEQ ID No:52; SEQ ID No:54; SEQ ID No:56; SEQ ID No:58; SEQ ID No:60; SEQ ID No:62; SEQ ID No:64; SEQ ID No:66; SEQ ID No:68; SEQ ID No:70; and SEQ ID No:72; and a sequence encoding a polypeptide having the sequence of an antibody Fc region, or a fragment thereof, from a species other than mouse.

In yet another aspect, the invention is directed to an isolated polynucleotide encoding a chimeric polypeptide having the sequence of SEQ ID No.:2. In one embodiment, the polynucleotide comprises a sequence encoding a polypeptide having the sequence of SEQ ID No.:2; and a sequence encoding a polypeptide having the sequence of an antibody Fc region, or a fragment thereof, from a species other than mouse. In yet another aspect, the invention is directed to an isolated polynucleotide encoding a chimeric polypeptide having the sequence of SEQ ID No.:76. In one embodiment, the polynucleotide comprises a sequence encoding a polypeptide having the sequence of SEQ ID No.:76; and a sequence encoding a polypeptide having the sequence of an antibody Fc region, or a fragment thereof, from a species other than mouse.

The invention is also directed to an isolated polynucleotide comprising a sequence encoding a polypeptide having the $V_H$ region of the murine B-Ly1 antibody, or functional variants thereof, and a sequence encoding a polypeptide having the sequence of an antibody Fc region, or a fragment thereof, from a species other than mouse. In another aspect, the invention is directed to an isolated polynucleotide comprising a sequence encoding a polypeptide having the $V_L$ region of the murine B-Ly1 antibody, or functional variants thereof, and a sequence encoding a polypeptide having the sequence of an antibody Fc region, or a fragment thereof, from a species other than mouse.

The invention is further directed to an expression vector comprising any of the isolated polynucleotides described above, and to a host cell that comprises such an expression vector. In a further aspect, the invention is directed to a host cell comprising any of the isolated polynucleotides described above.

In one aspect, the invention is directed to an isolated polypeptide comprising: (a) a sequence selected from a group consisting of: SEQ ID NO.: 15, SEQ ID NO.: 16 and SEQ ID NO.:17. (CDRs $V_{H-1}$); (b) a sequence selected from a group consisting of: SEQ ID NO.:25, SEQ ID NO.:26 and SEQ ID NO.:27 (CDRs $V_{H-2}$); and SEQ ID NO:28, wherein said polypeptide is a fusion polypeptide. In another aspect, the invention is directed to an isolated polypeptide comprising SEQ ID NO.:18, SEQ ID NO.: 19 and SEQ ID NO.:20. (CDRs $V_L$), wherein said polypeptide is a fusion polypeptide.

The invention is also directed to a chimeric polypeptide comprising the sequence of SEQ ID NO.:1 or a variant thereof. The invention is further directed to a chimeric polypeptide comprising the sequence of SEQ ID NO.:2 or a variant thereof. In one embodiment, any one of these polypeptides further comprises a human Fc region. The invention is also directed to a chimeric polypeptide comprising a sequence selected from the group consisting of SEQ ID No:30; SEQ ID No:32; SEQ ID No:34; SEQ ID No:36; SEQ ID No:38; SEQ ID No:40; SEQ ID No:42; SEQ ID No:44; SEQ ID No:46; SEQ ID No:48; SEQ ID No:50; SEQ ID No:52; SEQ ID No:54; SEQ ID No:56; SEQ ID No:58; SEQ ID No:60; SEQ ID No:62; SEQ ID No:64; SEQ ID No:66; SEQ ID No:68; SEQ ID No:70; and SEQ ID No:72, or a variant thereof. The invention is further directed to a chimeric polypeptide comprising the sequence of SEQ ID NO.:76 or a variant thereof. In one embodiment, any one of these polypeptides further comprises a human Fc region.

In another aspect the invention is directed to a polypeptide comprising a sequence derived from the murine B-Ly1 antibody and a sequence derived from a heterologous polypeptide and to an antigen-binding molecule comprising such a polypeptide. In one embodiment the antigen-binding molecule is an antibody. In a preferred embodiment, the antibody is chimeric. In another preferred embodiment, the antibody is humanized or primatized.

In an additional aspect, the invention is directed to an isolated polypeptide comprising SEQ ID NO: 13 or a variant thereof. In another aspect, the invention is directed to an isolated polypeptide comprising SEQ ID NO: 14.

In another aspect, the invention is directed to an ABM, which is capable of competing with the murine B-Ly1 antibody for binding to CD20 and which is chimeric. In one embodiment, the ABM is an antibody or a fragment thereof. In a further embodiment, the ABM is a recombinant antibody comprising a $V_H$ region having an amino acid sequence selected from the group consisting of SEQ ID NO.: 1; SEQ ID No:30; SEQ ID No:32; SEQ ID No:34; SEQ ID No:36; SEQ ID No:38; SEQ ID No:40; SEQ ID No:42; SEQ ID No:44; SEQ ID No:46; SEQ ID No:48; SEQ ID No:50; SEQ ID No:52; SEQ ID No:54; SEQ ID No:56; SEQ ID No:58; SEQ ID No:60; SEQ ID No:62; SEQ ID No:64; SEQ ID No:66; SEQ ID No:68; SEQ ID No:70; and SEQ ID No:72. In another embodiment, the ABM is a recombinant antibody comprising a $V_L$ region having an amino acid sequence selected from the group consisting of SEQ ID NO.: 2 and SEQ ID NO:76. In a further embodiment the ABM is a recombinant antibody that is primatized. In yet a further embodiment the ABM is a recombinant antibody that is humanized. In another embodiment, the ABM is a recombinant antibody comprising a human Fc region. In a further embodiment, any of the ABMs discussed above may be conjugated to a moiety such as a toxin or a radiolabel.

The invention is further related to an ABM of the present invention, said ABM having modified oligosaccharides. In one embodiment the modified oligosaccharides have reduced fucosylation as compared to non-modified oligosaccharides. In other embodiments, the modified oligosaccharides are hybrid or complex. In a further embodiment, the ABM has an increased proportion of nonfucosylated oligosaccharides or bisected, nonfucosylated oligosaccharides in the Fc region of said molecule. In one embodiment, the bisected, nonfucosylated oligosaccharides are hybrid. In a further embodiment, the bisected, nonfucosylated oligosaccharides are complex. In a one embodiment, at least 20% of the oligosacchardies in the Fc region of said polypeptide are nonfucosylated or bisected, nonfucosylated. In more preferred embodiments, at least 30%, 35%, 40%, 45%, 50%, 55%, 60%, 65%, 70% or 75% or more of the oligosaccharides are nonfucosylated or bisected, nonfucosylated.

The invention is further related to a polynucleotide encoding any of the ABMs discussed above, and to expression vectors and cells comprising such a polynucleotide.

The invention is further related to a method of producing an ABM, which is capable of competing with the murine B-Ly1 antibody for binding to CD20 and wherein said ABM is chimeric; said method comprising: (a) culturing a host cell comprising a polynucleotide that encodes an ABM of the present invention in a medium under conditions allowing the expression of said polynucleotide encoding said ABM; and (b) recovering said ABM from the resultant culture.

In another aspect, the invention is related to a pharmaceutical composition comprising the ABM of the invention. It is contemplated that the pharmaceutical composition may further comprise a pharmaceutically acceptable carrier, an adjuvant or a combination thereof.

In a further aspect, the invention is related to a method of treating a disease treatable by B-cell depletion. The method comprises administering a therapeutically effective amount of the ABM of the present invention to a human subject in need thereof. In a preferred embodiment, the disease is treated by administering an ABM that is a chimeric antibody, or a chimeric fragment of an antibody.

In yet another aspect, the invention is related to a host cell engineered to express at least one nucleic acid encoding a polypeptide having GnTIII activity in an amount sufficient to modify the oligosaccharides in the Fc region of produced by the host cell, wherein the ABM is capable of competing with the murine B-Ly1 antibody for binding to CD20 and wherein the ABM is chimeric. In one embodiment, the polypeptide having GnTIII activity is a fusion polypeptide. In another embodiment, the ABM produced by the host cell is an antibody or an antibody fragment. In a further embodiment, the ABM comprises a region equivalent to the Fc region of a human IgG.

The invention is also directed to an isolated polynucleotide comprising at least one complementarity determining region of the murine B-Ly1 antibody, or a variant or truncated form thereof containing at least the specificity-determining residues for said complementarity determining region, wherein said isolated polynucleotide encodes a fusion polypeptide. Preferably, such isolated polynucleotides encode a fusion polypeptide that is an antigen binding molecule. In one embodiment, the polynucleotide comprises three complementarity determining regions of the murine B-Ly1 antibody, or variants or truncated forms thereof containing at least the specificity-determining residues for each of said three complementarity determining regions. In another embodiment, the polynucleotide encodes the entire variable region of the light or heavy chain of a chimeric (e.g., humanized) antibody. The invention is further directed to the polypeptides encoded by such polynucleotides.

In another embodiment, the invention is directed to an antigen combining molecule comprising at least one complementarity determining region of the murine B-Ly1 antibody, or a variant or truncated form thereof containing at lest the specificity-determining residues for said complementarity determining region, and comprising a sequence derived from a heterologous polypeptide. In one embodiment, the antigen binding molecule comprises three complementarity determining regions of the murine B-Ly1 antibody, or variants or truncated forms thereof containing at least the specificity-determining residues for each of said three complementarity determining regions. In another aspect, the antigen binding molecule comprises the variable region of an antibody light or heavy chain. In one particularly useful embodiment, the antigen binding molecule is a chimeric, e.g., humanized, antibody. The invention is also directed to methods of making such antigen binding molecules, and the use of same in the treatment of disease, including B cell lymphomas.

The present invention is the first known instance in which a Type II anti-CD20 antibody has been engineered to have increases effector functions such as ADCC, while still retaining potent apoptosis ability. Accordingly, the present invention is directed to an engineered Type II anti-CD20 antibody having increased ADCC as a result of said engineering and without loss of substantial ability to induces apoptosis. In one embodiment, the Type II anti-CD20 antibodies have been engineered to have an altered pattern of glycosylation in the Fc region. In a particular embodiment, the altered glycosylation comprises an increased level of bisected complex residues in the Fc region. In another particular embodiment, the altered glycosylation comprises and reduced level of fucose residues in the Fc region. In another embodiment, the Type II anti-CD20 antibodies have undergone polypeptide engineering. The invention is further directed to methods of making such engineered Type II antibodies and to methods of using such antibodies in the treatment of various B cell disorders, including B cell lymphomas.

The host cell of the present invention may be selected from the group that includes, but is not limited to, a CHO cell, a BHK cell, a NSO cell, a SP2/0 cell, a YO myeloma cell, a P3X63 mouse myeloma cell, a PER cell, a PER.C6 cell or a hybridoma cell. In one embodiment, the host cell of the invention further comprises a transfected polynucleotide comprising a polynucleotide encoding the $V_L$ region of the murine B-Ly1 antibody or variants thereof and a sequence encoding a region equivalent to the Fc region of a human immunoglobulin. In another embodiment, the host cell of the invention further comprises a transfected polynucleotide comprising a polynucleotide encoding the $V_H$ region of the murine B-Ly1 antibody or variants thereof and a sequence encoding a region equivalent to the Fc region of a human immunoglobulin.

In a further aspect, the invention is directed to a host cell that produces an ABM that exhibits increased Fc receptor binding affinity and/or increased effector function as a result of the modification of its oligosaccharides. In one embodiment, the increased binding affinity is to an Fc receptor, particularly, the FcγRIIIA receptor. The effector function contemplated herein may be selected from the group that includes, but is not limited to, increased Fc-mediated cellular cytotoxicity; increased binding to NK cells; increased binding to macrophages; increased binding to polymorphonuclear cells; increased binding to monocytes; increased direct signaling inducing apoptosis; increased dendritic cell maturation; and increased T cell priming.

In a further embodiment, the host cell of the present invention comprises at least one nucleic acid encoding a polypeptide having GnTIII activity that is operably linked to a constitutive promoter element.

In another aspect, the invention is directed to a method for producing an ABM in a host cell, comprising: (a) culturing a host cell engineered to express at least one polynucleotide encoding a fusion polypeptide having GnTIII activity under conditions which permit the production of said ABM and which permit the modification of the oligosaccharides present on the Fc region of said ABM; and (b) isolating said ABM; wherein said ABM is capable of competing with the murine B-Ly1 antibody for binding to CD20 and wherein said ABM is chimeric. In one embodiment, the polypeptide having GnTIII activity is a fusion polypeptide, preferably comprising the catalytic domain of GnTIII and the Golgi localization domain of a heterologous Golgi resident polypeptide selected from the group consisting of the localization domain of mannosidase II, the localization domain of β(1,2)-N-acetylglucosaminyltransferase I ("GnTI"), the localization domain of mannosidase I, the localization domain of β(1,2)-N-acetylglucosaminyltransferase II ("GnTII"), and the localization domain of α1-6 core fucosyltransferase. Preferably, the Golgi localization domain is from mannosidase II or GnTI.

In a further aspect, the invention is directed to a method for modifying the glycosylation profile of an anti-CD20 ABM produced by a host cell comprising introducing into the host cell at least one nucleic acid or expression vector of the invention. In one embodiment, the ABM is an antibody or a fragment thereof; preferably comprising the Fc region of an IgG. Alternatively, the polypeptide is a fusion protein that includes a region equivalent to the Fc region of a human IgG.

In one aspect, the invention is related to a recombinant, chimeric antibody, or a fragment thereof, capable of competing with the murine B-Ly1 antibody for binding to CD20 and having reduced fucosylation.

In another aspect, the present invention is directed to a method of modifying the glycosylation of the recombinant antibody or a fragment thereof of the invention by using a fusion polypeptide having GnTIII activity and comprising the Golgi localization domain of a heterologous Golgi resident polypeptide. In one embodiment, the fusion polypeptides of the invention comprise the catalytic domain of GnTIII. In another embodiment, the Golgi localization domain is selected from the group consisting of: the localization domain of mannosidase II, the localization domain of GnTI, the localization domain of mannosidase I, the localization domain of GnTII and the localization domain of α1-6 core fucosyltransferase. Preferably, the Golgi localization domain is from mannosidase II or GnTI.

In one embodiment, the method of the invention is directed towards producing a recombinant, chimeric antibody or a fragment thereof, with modified oligosaccharides wherein said modified oligosaccharides have reduced fucosylation as compared to non-modified oligosaccharides. According to the present invention, these modified oligosaccharides may be hybrid or complex. In another embodiment, the method of the invention is directed towards producing a recombinant, chimeric antibody or a fragment thereof having an increased proportion of bisected, nonfucosylated oligosaccharides in the Fc region of said polypeptide. In one embodiment, the bisected, nonfucosylated oligosaccharides are hybrid. In another embodiment, the bisected, nonfucosylated oligosaccharides are complex. In a further embodiment, the method of the invention is directed towards producing a recombinant, chimeric antibody or a fragment thereof having at least 20% of the oligosaccharides in the Fc region of said polypeptide that are bisected, nonfucosylated. In a preferred embodiment, at least 30% of the oligosaccharides in the Fc region of said polypeptide are bisected, nonfucosylated. In another preferred embodiment, wherein at least 35% of the oligosaccharides in the Fc region of said polypeptide are bisected, nonfucosylated.

In a further aspect, the invention is directed to a recombinant, chimeric antibody or a fragment thereof, that exhibits increased Fc receptor binding affinity and/or increased effector function as a result of the modification of its oligosaccharides. In one embodiment, the increased binding affinity is to an Fc activating receptor. In a further embodiment, the Fc receptor is Fcγ activating receptor, particularly, the FcγRIIIA receptor. The effector function contemplated herein may be selected from the group that includes, but is not limited to, increased Fc-mediated cellular cytotoxicity; increased binding to NK cells; increased binding to macrophages; increased binding to polymorphonuclear cells; increased binding to monocytes; increased direct signaling inducing apoptosis; increased dendritic cell maturation; and increased T cell priming.

In another aspect, the invention is directed to a recombinant, chimeric antibody fragment, having the binding specificity of the murine B-Ly1 antibody and containing the Fc region, that is engineered to have increased effector function produced by any of the methods of the present invention.

In another aspect, the present invention is directed to a fusion protein that includes a polypeptide having the sequence of SEQ ID NO:1 and a region equivalent to the Fc region of an immunoglobulin and engineered to have increased effector function produced by any of the methods of the present invention.

In another aspect, the present invention is directed to a fusion protein that includes a polypeptide having the sequence of SEQ ID NO:2 and a region equivalent to the Fc region of an immunoglobulin and engineered to have increased effector function produced by any of the methods of the present invention.

In one aspect, the present invention is directed to a pharmaceutical composition comprising a recombinant, chimeric antibody, produced by any of the methods of the present invention, and a pharmaceutically acceptable carrier. In another aspect, the present invention is directed to a pharmaceutical composition comprising a recombinant, chimeric antibody fragment produced by any of the methods of the present invention, and a pharmaceutically acceptable carrier. In another aspect, the present invention is directed to a pharmaceutical composition comprising a fusion protein produced by any of the methods of the present invention, and a pharmaceutically acceptable carrier.

The invention is further directed to a method of treating a disease treatable by B-cell depletion comprising administering a therapeutically effective amount of the recombinant, chimeric, antibody or fragment thereof, produced by any of the methods of the present invention, to a human subject in need thereof.

BRIEF DESCRIPTION OF THE FIGURES

FIG. 1. Nucleotide (SEQ ID NO: 2, complementary nucleotide (SEQ ID NO:85) and amino acid sequence (SEQ ID NO:1) of the $V_H$ region of the murine B-Ly1. Also shown are the nucleotide sequence of the murine B-Ly1 $V_H$ region linker (SEQ ID NO:79), the complementary nucleotide sequence (SEQ ID NO:80), and the amino acid sequence (SEQ ID NO: 81).

FIG. 2 Nucleotide (SEQ ID NO:4), complementary nucleotide (SEQ ID NO:86) and amino acid sequence (SEQ ID NO: 3) of the $V_L$ region of the murine B-Ly1. Also shown are the nucleotide sequence of the murine B-Ly1 $V_L$ region linker (SEQ ID NO:82), the complementary nucleotide sequence (SEQ ID NO:83), and the amino acid sequence (SEQ ID NO:84).

FIG. 4. B-Cell depletion by Rituximab® (O) and ch-B_Ly1 (Δ) in whole blood of the three different classes of FcγRIIIa-158V/F genotype: (A) whole blood from a F/F donor, homozygous for the lower affinity receptor; (B) whole blood from a F/V donor, heterozygous for the affinity receptor; and (C) whole blood from a V/V donor, homozygous for the higher affinity receptor.

FIG. 5. Nucleotide (SEQ ID NO:11) and amino acid sequence (SEQ ID NO:13) of the heavy chain of a chimeric, anti-CD20 antibody.

FIG. 6. Nucleotide (SEQ ID NO:12) and amino acid sequence (SEQ ID NO:14) of the light chain of a chimeric, anti-CD20 antibody.

FIG. 7. Nucleotide and amino acid sequences of the murine B-Ly1 antibody CDRs. (A) Predicted CDRs for the $V_H$ region. (B) Predicted CDRs for the $V_L$ region.

DETAILED DESCRIPTION OF THE INVENTION

Figure 3:
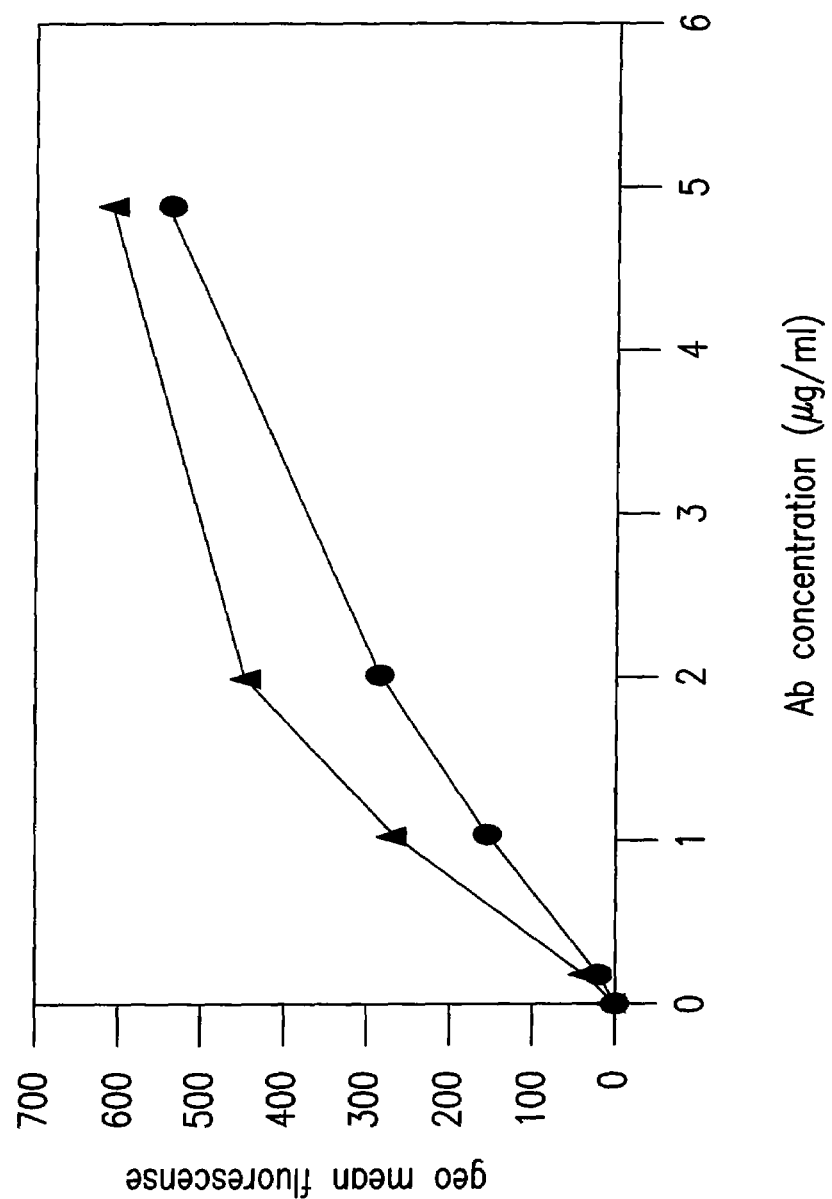
FIG. 3. Binding of Rituximab® (O) and ch-B_Ly1 (Δ) to CD20 on Raji B-lymphoma cells.
Figure 8A:
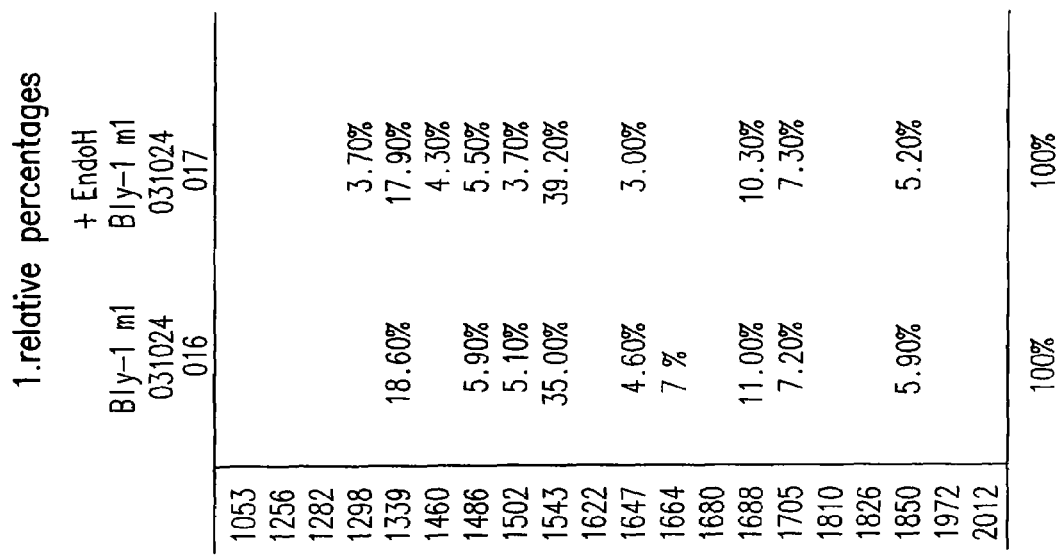
FIG. 8. MALDI-TOF profile of a glycoengineered, chimeric B-Ly1 antibody. (A) Table detailing the percentages of specific peaks; (B) Spectrum for glycoengineered chimeric B-Ly1; (C) Spectrum for glycoengineered chimeric B-Ly1 treated with Endo-H.
Figure 8B:
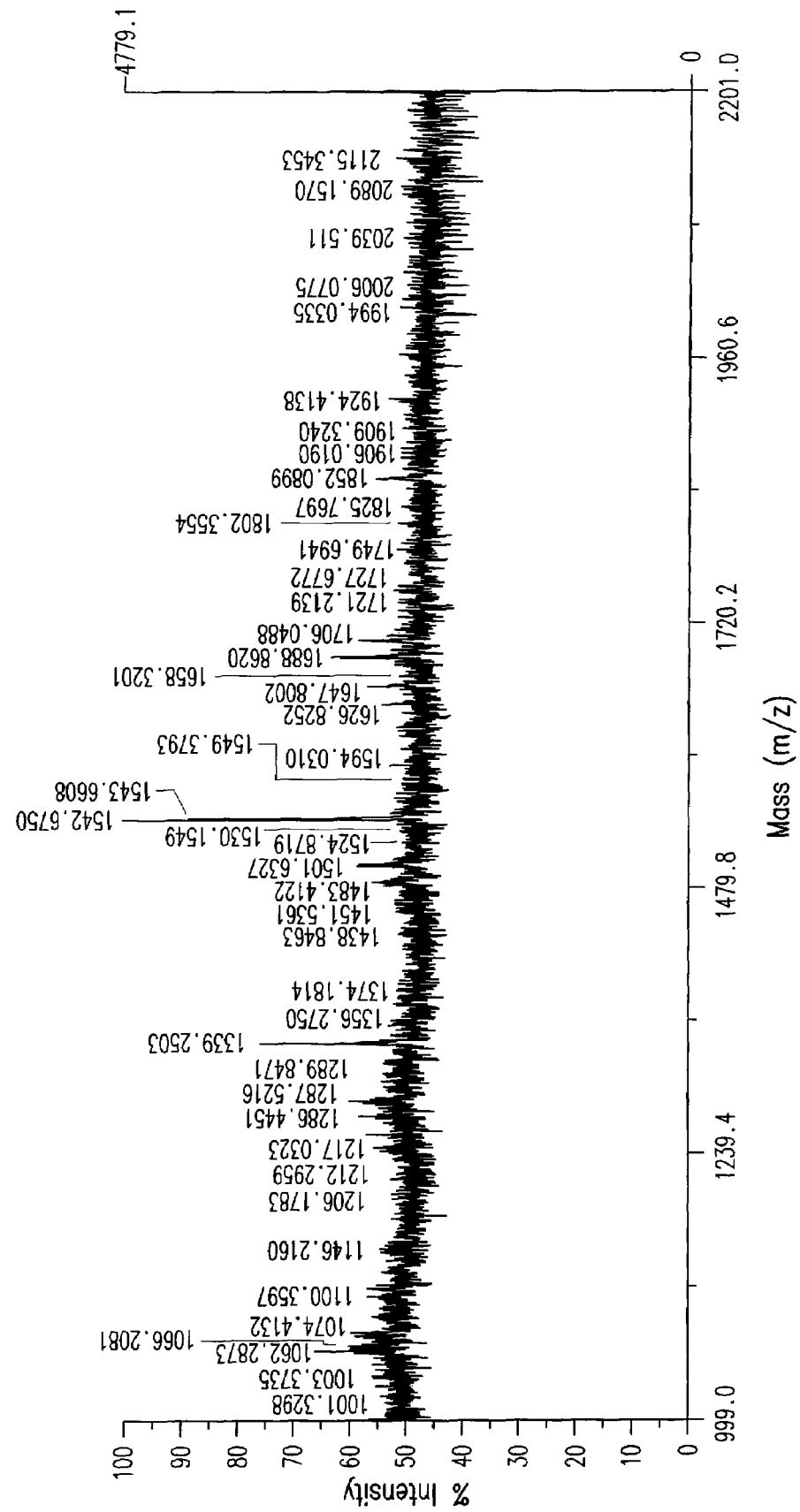
Figure 8C:
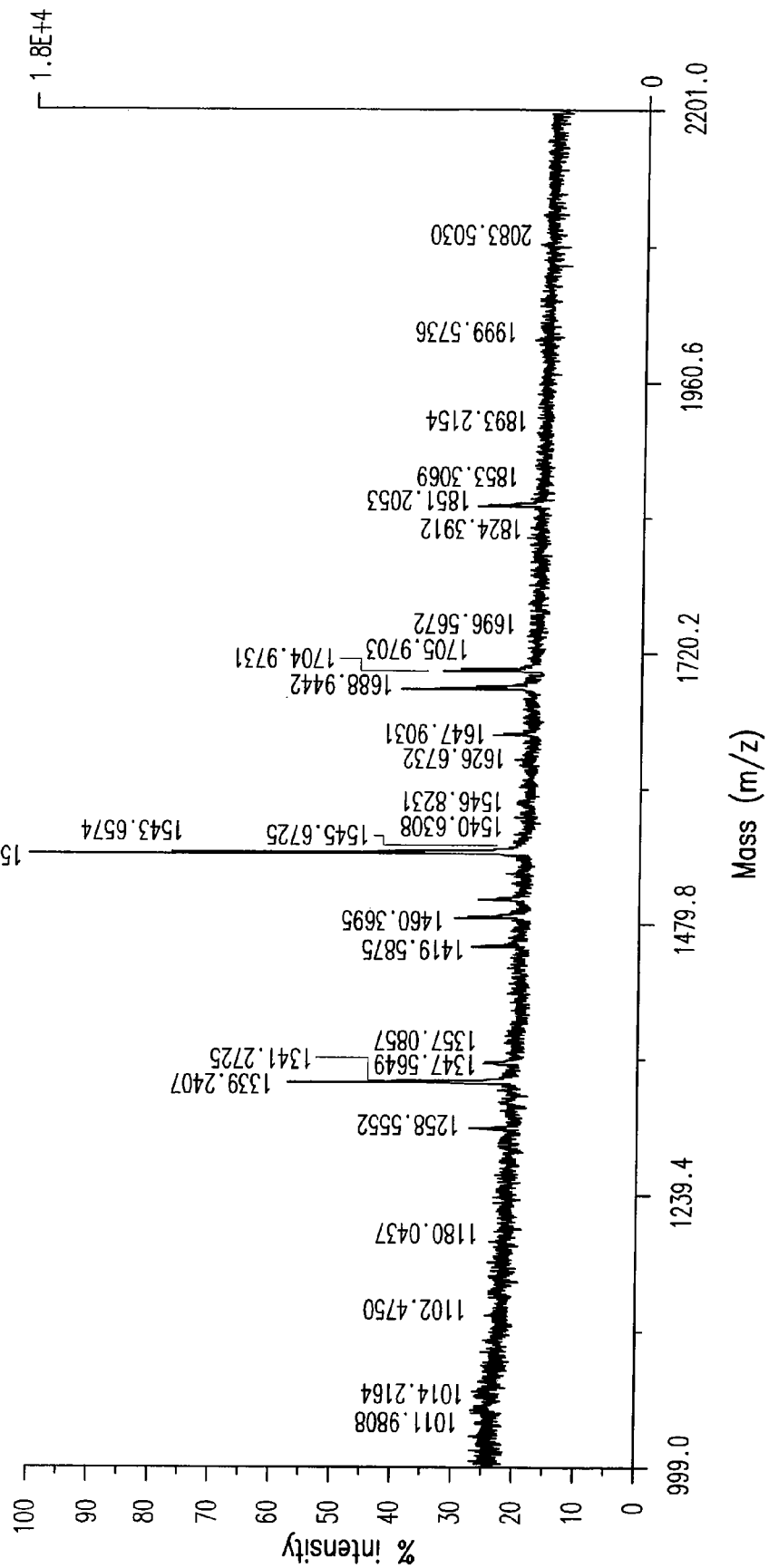
Figure 9:
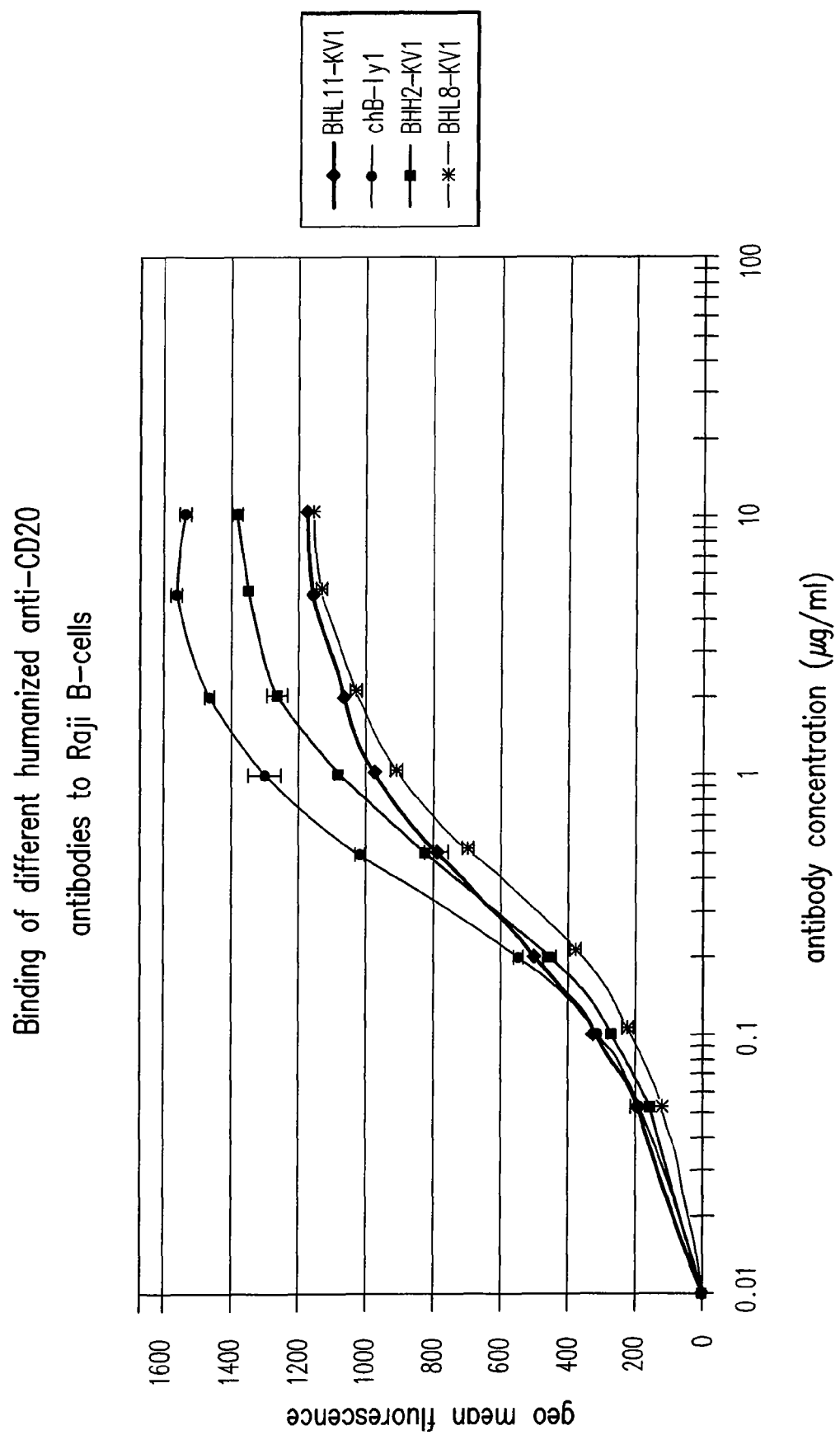
FIG. 9. Binding of different humanized anti-CD20 antibodies to Raji B-cells. The differences between the B-HH2 construct and the B-HL8 and B-HL11 constructs are located in the framework 1 and 2 regions with all three CDRs being identical. B-HL8 and B-HL11 have their FR1 and FR2 sequences derived from the human VH3 class, whereas the complete B-HH2 framework is human VH1 derived. B-HL11 is a derivative of B-HL8 with the single mutation Glu1Gln, with Gln being the amino acid residue in the B-HH2 construct. This means that the Glu1Gln exchange does not alter binding affinity or intensity. The other differences between B-HH2 and B-HL8 are 14 FR residues, from which one or more will influence the antigen binding behavior of this antibody.
Figure 10:
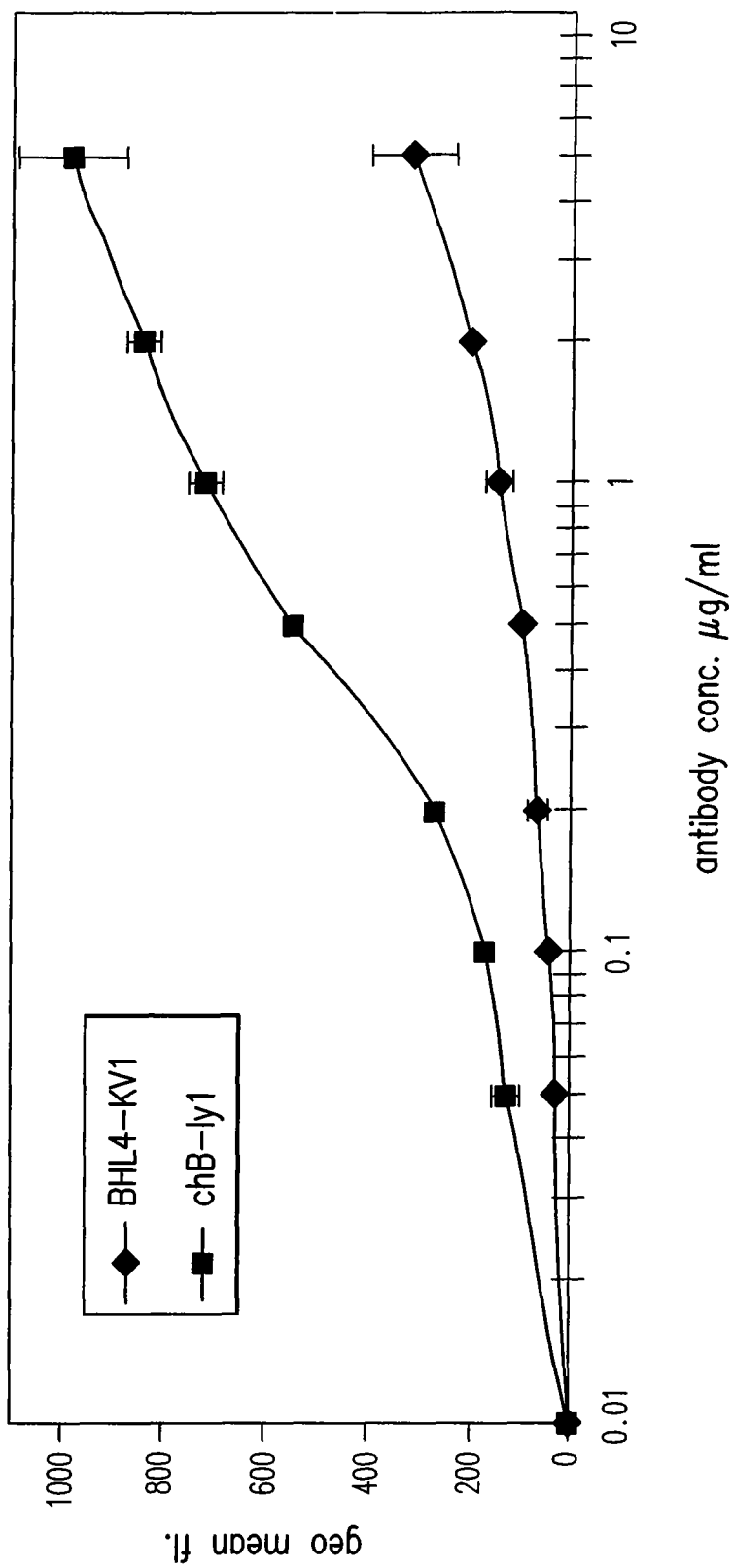
FIG. 10. Binding of the humanized anti-CD20 antibody BHL4-KV1 on Raji target cells. The B-HL4 construct is derived from the B-HH2 antibody by replacing the FR1 of the B-HH2 with that of the human germ line sequence VH1_45. This construct shows greatly diminished antigen binding capacity, despite of having different amino acids at only three positions within FR1. These residues are located at positions 2, 14, and 30 according to Kabat numbering. Of these, position 30 seems to be the most influential position, since it is part of the Chothia definition of CDR1.

Terms are used herein as generally used in the art, unless otherwise defined as follows.

As used herein, the term antibody is intended to include whole antibody molecules, including monoclonal, polyclonal and multispecific (e.g., bispecific) antibodies, as well as antibody fragments having the Fc region and retaining binding specificity, and fusion proteins that include a region equivalent to the Fc region of an immunoglobulin and that retain binding specificity. Also encompassed are humanized, primatized and chimeric antibodies.

As used herein, the term Fc region is intended to refer to a C-terminal region of an IgG heavy chain. Although the boundaries of the Fc region of an IgG heavy chain might vary slightly, the human IgG heavy chain Fc region is usually defined to stretch from the amino acid residue at position Cys226 to the carboxyl-terminus.

As used herein, the term region equivalent to the Fc region of an immunoglobulin is intended to include naturally occurring allelic variants of the Fc region of an immunoglobulin as well as variants having alterations which produce substitutions, additions, or deletions but which do not decrease substantially the ability of the immunoglobulin to mediate effector functions (such as antibody dependent cellular cytotoxicity). For example, one or more amino acids can be deleted from the N-terminus or C-terminus of the Fc region of an immunoglobulin without substantial loss of biological function. Such variants can be selected according to general rules known in the art so as to have minimal effect on activity. (See, e.g., Bowie, J. U. et al., *Science* 247:1306-10 (1990).

As used herein, the term antigen binding molecule refers in its broadest sense to a molecule that specifically binds an antigenic determinant. More specifically, an antigen binding molecule that binds CD20 is a molecule which specifically binds to a cell surface non-glycosylated phosphoprotein of 35,000 Daltons, typically designated as the human B lymphocyte restricted differentiation antigen Bp35, commonly referred to as CD20. By "specifically binds" is meant that the binding is selective for the antigen and can be discriminated from unwanted or nonspecific interactions.

As used herein, the terms fusion and chimeric, when used in reference to polypeptides such as ABMs refer to polypeptides comprising amino acid sequences derived from two or more heterologous polypeptides, such as portions of antibodies from different species. For chimeric ABMs, for example, the non-antigen binding components may be derived from a wide variety of species, including primates such as chimpanzees and humans. The constant region of the chimeric ABM is most preferably substantially identical to the constant region of a natural human antibody; the variable region of the chimeric antibody is most preferably substantially identical to that of a recombinant antiCD-20 antibody having the amino acid sequence of the murine B-Ly1 variable region. Humanized antibodies are a particularly preferred form of fusion or chimeric antibody.

As used herein, a polypeptide having "GnTIII activity" refers to polypeptides that are able to catalyze the addition of a N-acetylglucosamine (GlcNAc) residue in β-1-4 linkage to the β-linked mannoside of the trimannosyl core of N-linked oligosaccharides. This includes fusion polypeptides exhibiting enzymatic activity similar to, but not necessarily identical to, an activity of β(1,4)-N-acetylglucosaminyltransferase III, also known as β-1,4-mannosyl-glycoprotein 4-beta-N-acetylglucosaminyl-transferase (EC 2.4.1.144), according to the Nomenclature Committee of the International Union of Biochemistry and Molecular Biology (NC-IUBMB), as measured in a particular biological assay, with or without dose dependency. In the case where dose dependency does exist, it need not be identical to that of GnTIII, but rather substantially similar to the dose-dependence in a given activity as compared to the GnTIII (i.e., the candidate polypeptide will exhibit greater activity or not more than about 25-fold less and, preferably, not more than about tenfold less activity, and most preferably, not more than about three-fold less activity relative to the GnTIII.)

As used herein, the term variant (or analog) refers to a polypeptide differing from a specifically recited polypeptide of the invention by amino acid insertions, deletions, and substitutions, created using, e.g., recombinant DNA techniques. Variants of the ABMs of the present invention include chimeric, primatized or humanized antigen binding molecules wherein one or several of the amino acid residues are modified by substitution, addition and/or deletion in such manner that does not substantially affect antigen (e.g., CD20) binding affinity. Guidance in determining which amino acid residues may be replaced, added or deleted without abolishing activities of interest, may be found by comparing the sequence of the particular polypeptide with that of homologous peptides and minimizing the number of amino acid sequence changes made in regions of high homology (conserved regions) or by replacing amino acids with consensus sequence.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations in the polynucleotide sequence may be reflected in the polypeptide or domains of other peptides added to the polypeptide to modify the properties of any part of the polypeptide, to change characteristics such as ligand-binding affinities, interchain affinities, or degradation/turnover rate.

Preferably, amino acid "substitutions" are the result of replacing one amino acid with another amino acid having similar structural and/or chemical properties, i.e., conservative amino acid replacements. "Conservative" amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Insertions" or "deletions" are preferably in the range of about 1 to 20 amino acids, more preferably 1 to 10 amino acids. The variation allowed may be experimentally determined by systematically making insertions, deletions, or substitutions of amino acids in a polypeptide molecule using recombinant DNA techniques and assaying the resulting recombinant variants for activity.

As used herein, the term humanized is used to refer to an antigen-binding molecule derived from a non-human antigen-binding molecule, for example, a murine antibody, that retains or substantially retains the antigen-binding properties of the parent molecule but which is less immunogenic in humans. This may be achieved by various methods including (a) grafting the entire non-human variable domains onto human constant regions to generate chimeric antibodies, (b) grafting only the non-human CDRs onto human framework and constant regions with or without retention of critical framework residues (e.g., those that are important for retaining good antigen binding affinity or antibody functions), or (c) transplanting the entire non-human variable domains, but "cloaking" them with a human-like section by replacement of surface residues. Such methods are disclosed in Jones et al., Morrison et al., Proc. Natl. Acad. Sci., 81:6851-6855 (1984); Morrison and Oi, Adv. Immunol., 44:65-92 (1988); Verhoeyen et al., Science, 239:1534-1536 (1988); Padlan, Molec. Immun., 28:489-498 (1991); Padlan, Molec. Immun., 31(3): 169-217 (1994), all of which are incorporated by reference in their entirety herein. There are generally 3 complementarity determining regions, or CDRs, (CDR1, CDR2 and CDR3) in each of the heavy and light chain variable domains of an antibody, which are flanked by four framework subregions (i.e., FR1, FR2, FR3, and FR4) in each of the heavy and light chain variable domains of an antibody: FR1-CDR1-FR2-CDR2-FR3-CDR3-FR4. A discussion of humanized antibodies can be found, inter alia, in U.S. Pat. No. 6,632,927, and in published U.S. Application No. 2003/0175269, both of which are incorporated herein by reference in their entirety.

Similarly, as used herein, the term primatized is used to refer to an antigen-binding molecule derived from a non-primate antigen-binding molecule, for example, a murine antibody, that retains or substantially retains the antigen-binding properties of the parent molecule but which is less immunogenic in primates.

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., J. Mol. Biol. 196:901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table I as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE 1

CDR Definitions[1]

|  | Kabat | Chothia | AbM |
|---|---|---|---|
| $V_H$ CDR1 | 31-35 | 26-32 | 26-35 |
| $V_H$ CDR2 | 50-65 | 52-58 | 50-58 |
| $V_H$ CDR3 | 95-102 | 95-102 | 95-102 |
| $V_L$ CDR1 | 24-34 | 26-32 |  |
| $V_L$ CDR2 | 50-56 | 50-52 |  |
| $V_L$ CDR3 | 89-97 | 91-96 |  |

[1]Numbering of all CDR definitions in Table 1 is according to the numbering conventions set forth by Kabat et al. (see below).

Kabat et al. also defined a numbering system for variable domain sequences that is applicable to any antibody. One of ordinary skill in the art can unambigously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an ABM are according to the Kabat numbering system. The sequences of the sequence listing (i.e., SEQ ID NO:1 to SEQ ID NO:78) are not numbered according to the Kabat numbering system.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be the entire sequence shown in either FIG. 24 or FIG. 25.

As a practical matter, whether any particular nucleic acid molecule or polypeptide is at least 80%, 85%, 90%, 95%, 96%, 97%, 98% or 99% identical to a nucleotide sequence or polypeptide sequence of the present invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al., Comp. App. Biosci. 6:237-245 (1990). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 95%, 96%, 97%, 98% or 99% identical to a reference polypeptide can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al., *Comp. App. Biosci.* 6:237-245 (1990). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to be made for the purposes of the present invention.

As used herein, a nucleic acid that "hybridizes under stringent conditions" to a nucleic acid sequence of the invention, refers to a polynucleotide that hybridizes in an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

As used herein, the term Golgi localization domain refers to the amino acid sequence of a Golgi resident polypeptide which is responsible for anchoring the polypeptide in location within the Golgi complex. Generally, localization domains comprise amino terminal "tails" of an enzyme.

As used herein, the term effector function refers to those biological activities attributable to the Fc region (a native sequence Fc region or amino acid sequence variant Fc region) of an antibody. Examples of antibody effector functions include, but are not limited to, Fc receptor binding affinity, antibody-dependent cellular cytotoxicity (ADCC), antibody-dependent cellular phagocytosis (ADCP), cytokine secretion, immune-complex-mediated antigen uptake by antigen-presenting cells, down-regulation of cell surface receptors, etc.

As used herein, the terms engineer, engineered, engineering and glycosylation engineering are considered to include any manipulation of the glycosylation pattern of a naturally occurring or recombinant polypeptide or fragment thereof. Glycosylation engineering includes metabolic engineering of the glycosylation machinery of a cell, including genetic manipulations of the oligosaccharide synthesis pathways to achieve altered glycosylation of glycoproteins expressed in cells. Furthermore, glycosylation engineering includes the effects of mutations and cell environment on glycosylation.

As used herein, the term host cell covers any kind of cellular system which can be engineered to generate the polypeptides and antigen-binding molecules of the present invention. In one embodiment, the host cell is engineered to allow the production of an antigen binding molecule with modified glycoforms. In a preferred embodiment, the antigen binding molecule is an antibody, antibody fragment, or fusion protein. In certain embodiments, the host cells have been further manipulated to express increased levels of one or more polypeptides having GnTIII activity. Host cells include cultured cells, e.g., mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

As used herein, the term Fc-mediated cellular cytotoxicity includes antibody-dependent cellular cytotoxicity and cellular cytotoxicity mediated by a soluble Fc-fusion protein containing a human Fc-region. It is an immune mechanism leading to the lysis of "antibody-targeted cells" by "human immune effector cells", wherein:

The human immune effector cells are a population of leukocytes that display Fc receptors on their surface through which they bind to the Fc-region of antibodies or of Fc-fusion proteins and perform effector functions. Such a population may include, but is not limited to, peripheral blood mononuclear cells (PBMC) and/or natural killer (NK) cells.

The antibody-targeted cells are cells bound by the antibodies or Fc-fusion proteins. The antibodies or Fc fusion-proteins bind to target cells via the protein part N-terminal to the Fc region.

As used herein, the term increased Fc-mediated cellular cytotoxicity is defined as either an increase in the number of "antibody-targeted cells" that are lysed in a given time, at a given concentration of antibody, or of Fc-fusion protein, in the medium surrounding the target cells, by the mechanism of Fc-mediated cellular cytotoxicity defined above, and/or a reduction in the concentration of antibody, or of Fc-fusion protein, in the medium surrounding the target cells, required to achieve the lysis of a given number of "antibody-targeted cells", in a given time, by the mechanism of Fc-mediated cellular cytotoxicity. The increase in Fc-mediated cellular cytotoxicity is relative to the cellular cytotoxicity mediated by the same antibody, or Fc-fusion protein, produced by the same type of host cells, using the same standard production, purification, formulation and storage methods, which are known to those skilled in the art, but that has not been produced by host cells engineered to express the glycosyltransferase GnTIII by the methods described herein.

By antibody having increased antibody dependent cellular cytotoxicity (ADCC) is meant an antibody, as that term is defined herein, having increased ADCC as determined by any suitable method known to those of ordinary skill in the art. One accepted in vitro ADCC assay is as follows:

1) the assay uses target cells that are known to express the target antigen recognized by the antigen-binding region of the antibody;

2) the assay uses human peripheral blood mononuclear cells (PBMCs), isolated from blood of a randomly chosen healthy donor, as effector cells;

3) the assay is carried out according to following protocol:
 i) the PBMCs are isolated using standard density centrifugation procedures and are suspended at $5 \times 10^6$ cells/ml in RPMI cell culture medium;
 ii) the target cells are grown by standard tissue culture methods, harvested from the exponential growth phase with a viability higher than 90%, washed in RPMI cell culture medium, labeled with 100 micro-Curies of $^{51}$Cr, washed twice with cell culture medium, and resuspended in cell culture medium at a density of $10^5$ cells/ml;
 iii) 100 microliters of the final target cell suspension above are transferred to each well of a 96-well microtiter plate;
 iv) the antibody is serially-diluted from 4000 ng/ml to 0.04 ng/ml in cell culture medium and 50 microliters of the resulting antibody solutions are added to the target cells in the 96-well microtiter plate, testing in triplicate various antibody concentrations covering the whole concentration range above;
 v) for the maximum release (MR) controls, 3 additional wells in the plate containing the labeled target cells, receive 50 microliters of a 2% (V/V) aqueous solution of non-ionic detergent (Nonidet, Sigma, St. Louis), instead of the antibody solution (point iv above);
 vi) for the spontaneous release (SR) controls, 3 additional wells in the plate containing the labeled target cells, receive 50 microliters of RPMI cell culture medium instead of the antibody solution (point iv above);
 vii) the 96-well microtiter plate is then centrifuged at $50 \times g$ for 1 minute and incubated for 1 hour at 4° C.;
 viii) 50 microliters of the PBMC suspension (point i above) are added to each well to yield an effector:target cell ratio of 25:1 and the plates are placed in an incubator under 5% $CO_2$ atmosphere at 37° C. for 4 hours;
 ix) the cell-free supernatant from each well is harvested and the experimentally released radioactivity (ER) is quantified using a gamma counter;
 x) the percentage of specific lysis is calculated for each antibody concentration according to the formula (ER-MR)/(MR-SR)×100, where ER is the average radioactivity quantified (see point ix above) for that antibody concentration, MR is the average radioactivity quantified (see point ix above) for the MR controls (see point v above), and SR is the average radioactivity quantified (see point ix above) for the SR controls (see point vi above);

4) "increased ADCC" is defined as either an increase in the maximum percentage of specific lysis observed within the antibody concentration range tested above, and/or a reduction in the concentration of antibody required to achieve one half of the maximum percentage of specific lysis observed within the antibody concentration range tested above. The increase in ADCC is relative to the ADCC, measured with the above assay, mediated by the same antibody, produced by the same type of host cells, using the same standard production, purification, formulation and storage methods, which are known to those skilled in the art, but that has not been produced by host cells engineered to overexpress GnTIII.

In one aspect, the present invention is related to antigen binding molecules having the binding specificity of the murine B-Ly1 antibody, and to the discovery that their effector functions can be enhanced by altered glycosylation. In one embodiment, the antigen binding molecule is a chimeric antibody. In a preferred embodiment, the invention is directed to a chimeric antibody, or a fragment thereof, comprising the CDRs shown in FIG. 7. Specifically, in a preferred embodiment, the invention is directed to an isolated polynucleotide comprising: (a) a sequence selected from a group consisting of: SEQ ID NO.:5, SEQ ID NO.: 6 and SEQ ID NO.:7. (CDRs $V_{H-1}$); and (b) a sequence selected from a group consisting of: SEQ ID NO.:21, SEQ ID NO.:22 and SEQ ID NO.:23. (CDRs $V_{H-2}$); and SEQ ID NO:24. In another preferred embodiment, the invention is directed to an isolated polynucleotide comprising SEQ ID NO.:8, SEQ ID NO.: 9 and SEQ ID NO.: 10. (CDRs $V_L$). In one embodiment, any of these polynucleotides encodes a fusion polypeptide.

In another embodiment, the antigen binding molecule comprises the $V_H$ domain of the murine B-Ly1 antibody shown in FIG. 1, or a variant thereof; and a non-murine polypeptide. In another preferred embodiment, the invention is directed to an antigen binding molecule comprising the $V_L$ domain of the murine B-Ly1 antibody shown in FIG. 2, or a variant thereof; and a non-murine polypeptide.

In another aspect, the invention is directed to antigen binding molecules comprising one or more truncated CDRs of BLy-1. Such truncated CDRs will contain, at a minimum, the specificity-determining amino acid residues for the given CDR. By "specificity-determining residue" is meant those residues that are directly involved in the interaction with the antigen. In general, only about one-fifth to one-third of the residues in a given CDR participate in binding to antigen. The specificity-determining residues in a particular CDR can be identified by, for example, computation of interatomic contacts from three-dimensional modeling and determination of the sequence variability at a given residue position in accordance with the methods described in Padlan et al., *FASEB J.* 9(1):133-139 (1995), the contents of which are hereby incorporated by reference in their entirety.

Accordingly, the invention is also directed to an isolated polynucleotide comprising at least one complementarity determining region of the murine B-Ly1 antibody, or a variant or truncated form thereof containing at least the specificity-determining residues for said complementarity determining region, wherein said isolated polynucleotide encodes a fusion polypeptide. Preferably, such isolated polynucleotides encode a fusion polypeptide that is an antigen binding molecule. In one embodiment, the polynucleotide comprises three complementarity determining regions of the murine B-Ly1 antibody, or variants or truncated forms thereof containing at least the specificity-determining residues for each of said three complementarity determining regions. In another embodiment, the polynucleotide encodes the entire variable region of the light or heavy chain of a chimeric (e.g., humanized) antibody. The invention is further directed to the polypeptides encoded by such polynucleotides.

In another embodiment, the invention is directed to an antigen combining molecule comprising at least one complementarity determining region of the murine B-Ly1 antibody, or a variant or truncated form thereof containing at lest the specificity-determining residues for said complementarity determining region, and comprising a sequence derived from a heterologous polypeptide. In one embodiment, the antigen binding molecule comprises three complementarity determining regions of the murine B-Ly1 antibody, or variants or truncated forms thereof containing at least the specificity-determining residues for each of said three complementarity determining regions. In another aspect, the antigen binding molecule comprises the variable region of an antibody light or heavy chain. In one particularly useful embodiment, the antigen binding molecule is a chimeric, e.g., humanized, antibody. The invention is also directed to methods of making such antigen binding molecules, and the use of same in the treatment of disease, including B cell lymphomas.

It is known that several mechanism are involved in the therapeutic efficacy of anti-CD20 antibodies, including antibody dependent cellular cytotoxicity (ADCC), complement-dependent cytotoxicity (CDC), and the induction of growth arrest or apoptosis. For example, the majority of experimental evidence indicates that rituximab operates through conventional effector mechanisms measured by CDC and ADCC assays. Similarly, it has been shown that the resistance of different lymphoma cells to rituximab in vivo is a function of their sensitivity to CDC in vitro. In contrast, the mode of action in vivo of another antibody that has been approved for therapeutic use, B1, requires neither complement nor natural killer (NK) cell activity. Rather, the efficacy of B1 in vivo is due to its ability to induce potent apoptosis.

In general, anti-CD20 monoclonal antibodies fall into two distinct categories based on their mechanism of action in eradicating lymphoma cells. Type I anti-CD20 antibodies primarily utilize complement to kill target cells, while Type II antibodies operate by different mechanisms, primarily apoptosis. Rituximab and 1F5 are examples of Type I anti-CD20 antibodies, whereas B1 is an example of a Type II antibody. See, e.g., Cragg, M. S, and Glennie, M. J., Blood 103(7): 2738-2743 (April 2004); Teeling, J. L. et al., Blood 104(6): 1793-1800 (September 2004), the entire contents of which are hereby incorporated by reference.

The present invention is the first known instance in which a Type II anti-CD20 antibody has been engineered to have increases effector functions such as ADCC, while still retaining potent apoptosis ability. Accordingly, the present invention is directed to an engineered Type II anti-CD20 antibody having increased ADCC as a result of said engineering and without loss of substantial ability to induces apoptosis. In one embodiment, the Type II anti-CD20 antibodies have been engineered to have an altered pattern of glycosylation in the Fc region. In a particular embodiment, the altered glycosylation comprises an increased level of bisected complex residues in the Fc region. In another particular embodiment, the altered glycosylation comprises and reduced level of fucose residues in the Fc region. See U.S. Pat. Appl. Pub. No. 2004 0093621 to Shitara et al., the entire contents of which is incorporated by reference. In another embodiment, the Type II anti-CD20 antibodies have undergone polypeptide engineering as taught in U.S. Pat. No. 6,737,056 to Presta or U.S. Pat. Appl. Pub. No. 2004 0185045 (Macrogenics) or U.S. Pat. Appl. Pub. No. 2004 0132101 (Xencor), the entire contents of each of which are incorporated by reference. The invention is further directed to methods of making such engineered Type II antibodies and to methods of using such antibodies in the treatment of various B cell disorders, including B cell lymphomas.

Chimeric mouse/human antibodies have been described. See, for example, Morrison, S. L. et al., *PNAS I*1:6851-6854 (November 1984); European Patent Publication No. 173494; Boulianna, G. L, at al., *Nature* 312:642 (December 1984); Neubeiger, M. S. et al., *Nature* 314:268 (March 1985); European Patent Publication No. 125023; Tan et al., *J. Immunol.* 135:8564 (November 1985); Sun, L. K et al., *Hybridoma* 5(1):517 (1986); Sahagan et al., *J. Immunol.* 137:1066-1074 (1986). See generally, Muron, *Nature* 312:597 (December 1984); Dickson, *Genetic Engineering News* 5(3) (March 1985); Marx, *Science* 229:455 (August 1985); and Morrison, *Science* 229:1202-1207 (September 1985). Robinson et al., in PCT Publication Number WO/88104936 describe a chimeric antibody with human constant region and murine variable region, having specificity to an epitope of CD20; the murine portion of the chimeric antibody of the Robinson references is derived from the 2H7 mouse monoclonal antibody (gamma 2b, kappa). While the reference notes that the described chimeric antibody is a "prime candidate" for the treatment of B cell disorders, this statement can be viewed as no more than a suggestion to those in the art to determine whether or not this suggestion is accurate for this particular antibody, particularly because the reference lacks any data to support an assertion of therapeutic effectiveness, and importantly, data using higher order mammals such as primates or humans.

Methodologies for generating chimeric antibodies are available to those in the art. For example, the light and heavy chains can be expressed separately, using, for example, immunoglobulin light chain and immunoglobulin heavy chains in separate plasmids, or on a single (e.g., polycistronic) vector. These can then be purified and assembled in vitro into complete antibodies; methodologies for accomplishing such assembly have been described. See, for example, Scharff, M., Harvey Lectures 69:125 (1974). In vitro reaction parameters for the formation of IgG antibodies from reduced isolated light and heavy chains have also been described. See, for example, Sears et al., *Biochem.* 16(9): 2016-25 (1977).

In a particularly preferred embodiment, the chimeric ABM of the present invention is a humanized antibody. Methods for humanizing non-human antibodies are known in the art. For example, humanized ABMs of the present invention can be prepared according to the methods of U.S. Pat. No. 5,225,539 to Winter, U.S. Pat. No. 6,180,370 to Queen et al., or U.S. Pat. No. 6,632,927 to Adair et al., the entire contents of each of which is hereby incorporated by reference. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239: 1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies. The subject humanized anti-CD20 antibodies will comprise constant regions of human immunoglobulin.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanized antibody (Sims et al., *J. Immunol.*, 151:2296 (1993); Chothia et al., *J. Mol. Biol.*, 196:901 (1987)). Another method of selecting the human framework sequence is to compare the sequence of each individual subregion of the full rodent framework (i.e., FR1, FR2, FR3, and FR4) or some combination of the individual subregions (e.g., FR1 and FR2) against a library of known human variable region sequences that correspond to that framework subregion (e.g., as determined by Kabat numbering), and choose the human sequence for each subregion or combination that is the closest to that of the rodent (Leung U.S. Patent Application Publication No. 2003/0040606A1, published Feb. 27, 2003). Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

In another embodiment, the antigen binding molecules of the present invention are engineered to have enhanced binding affinity according to, for example, the methods disclosed in U.S. Pat. Appl. Pub. No. 2004/0132066 to Balint et al., the entire contents of which are hereby incorporated by reference.

In one embodiment, the antigen binding molecule of the present invention is conjugated to an additional moiety, such as a radiolabel or a toxin. Such conjugated ABMs can be produced by numerous methods that are well known in the art.

A variety of radionuclides are applicable to the present invention and those skilled in the art are credited with the ability to readily determine which radionuclide is most appropriate under a variety of circumstances. For example, $^{131}$iodine is a well known radionuclide used for targeted immunotherapy. However, the clinical usefulness of $^{131}$iodine can be limited by several factors including: eight-day physical half-life; dehalogenation of iodinated antibody both in the blood and at tumor sites; and emission characteristics (eg, large gamma component) which can be suboptimal for localized dose deposition in tumor. With the advent of superior chelating agents, the opportunity for attaching metal chelating groups to proteins has increased the opportunities to utilize other radionuclides such as $^{111}$indium and $^{90}$yttrium. $^{90}$Yttrium provides several benefits for utilization in radioimmunotherapeutic applications: the 64 hour half-life of $^{90}$yttrium is long enough to allow antibody accumulation by tumor and, unlike eg, $^{131}$iodine, $^{90}$yttrium is a pure beta emitter of high energy with no accompanying gamma irradiation in its decay, with a range in tissue of 100 to 1000 cell diameters. Furthermore, the minimal amount of penetrating radiation allows for outpatient administration of $^{90}$yttrium-labeled antibodies. Additionally, internalization of labeled antibody is not required for cell killing, and the local emission of ionizing radiation should be lethal for adjacent tumor cells lacking the target antigen.

Effective single treatment dosages (i.e., therapeutically effective amounts) of $^{90}$yttrium labeled anti-CD20 antibodies range from between about 5 and about 75 mCi, more preferably between about 10 and about 40 mCi. Effective single treatment non-marrow ablative dosages of $^{131}$iodine labeled anti-CD20 antibodies range from between about 5 and about 70 mCi, more preferably between about 5 and about 40 mCi. Effective single treatment ablative dosages (ie, may require autologous bone marrow transplantation) of $^{131}$iodine labeled anti-CD20 antibodies range from between about 30 and about 600 mCi, more preferably between about 50 and less than about 500 mCi. In conjunction with a chimeric anti-CD20 antibody, owing to the longer circulating half life vis-a-vis murine antibodies, an effective single treatment non-marrow ablative dosages of $^{131}$iodine labeled chimeric anti-CD20 antibodies range from between about 5 and about 40 mCi, more preferably less than about 30 mCi. Imaging criteria for, e.g., the $^{111}$indium label, are typically less than about 5 mCi.

With respect to radiolabeled anti-CD20 antibodies, therapy therewith can also occur using a single therapy treatment or using multiple treatments. Because of the radionuclide component, it is preferred that prior to treatment, peripheral stem cells ("PSC") or bone marrow ("BM") be "harvested" for patients experiencing potentially fatal bone marrow toxicity resulting from radiation. BM and/or PSC are harvested using standard techniques, and then purged and frozen for possible reinfusion. Additionally, it is most preferred that prior to treatment a diagnostic dosimetry study using a diagnostic labeled antibody (eg, using $^{111}$indium) be conducted on the patient, a purpose of which is to ensure that the therapeutically labeled antibody (eg, using $^{90}$yttrium) will not become unnecessarily "concentrated" in any normal organ or tissue.

In a preferred embodiment, the present invention is directed to an isolated polynucleotide comprising a sequence that encodes a polypeptide having an amino acid sequence as shown in Table 3 below. The invention is further directed to an isolated nucleic acid comprising a sequence at least 80%, 85%, 90%, 95%, 96%, 97%, 98% or 99% identical to a nucleotide sequence shown in Table 2 below. In another embodiment, the invention is directed to an isolated nucleic acid comprising a sequence that encodes a polypeptide having an amino acid sequence at least 80%, 85%, 90%, 95%, 96%, 97%, 98% or 99% identical to an amino acid sequence in Table 3. The invention also encompasses an isolated nucleic acid comprising a sequence that encodes a polypeptide having the amino acid sequence of any of the constructs in Table 3 with conservative amino acid substitutions.

TABLE 2

| CONSTRUCT | NUCLEOTIDE SEQUENCE | SEQ ID NO |
|---|---|---|
| B-HH1 | CAGGTGCAATTGGTGCAGTCTGGCGCTGAAGTTA AGAAGCCTGGGAGTTCAGTGAAGGTCTCCTGCAA GGCTTCCGGATACACCTTCAGCTATTCTTGGATG AGCTGGGTGCGGCAGGCCCCTGGACAAGGGCTCG AGTGGATGGGACGGATCTTTCCCGGCGATGGGGA TACTGACTACGCACAGAAATTCCAAGGAAGAGTC ACAATTACCGCCGACAAATCCACTAGCACAGCCT ATATGGAGCTGAGCAGCCTGAGATCTGAGGACAC GGCCGTGTATTACTGTGCAAGAAATGTCTTTGAT GGTTACTGGCTTGTTTACTGGGGCCAGGGAACCC TGGTCACCGTCTCCTCA | 29 |
| B-HH2 | CAGGTGCAATTGGTGCAGTCTGGCGCTGAAGTTA AGAAGCCTGGGAGTTCAGTGAAGGTCTCCTGCAA GGCTTCCGGATACGCCTTCAGCTATTCTTGGATG AACTGGGTGCGGCAGGCCCCTGGACAAGGGCTCG AGTGGATGGGACGGATCTTTCCCGGCGATGGGGA TACTGACTACAATGGGAAATTCAAGGGCAGAGTC ACAATTACCGCCGACAAATCCACTAGCACAGCCT | 31 |

TABLE 2-continued

| CONSTRUCT | NUCLEOTIDE SEQUENCE | SEQ ID NO |
|---|---|---|
| | ATATGGAGCTGAGCAGCCTGAGATCTGAGGACAC GGCCGTGTATTACTGTGCAAGAAATGTCTTTGAT GGTTACTGGCTTGTTTACTGGGGCCAGGGAACCC TGGTCACCGTCTCCTCA | |
| B-HH3 | CAGGTGCAATTGGTGCAGTCTGGCGCTGAAGTTA AGAAGCCTGGGAGTTCAGTGAAGGTCTCCTGCAA GGCTTCCGGATACGCCTTCAGCTATTCTTGGATG AACTGGGTGCGGCAGGCCCCTGGACAAGGGCTCG AGTGGATGGGACGGATCTTTCCCGGCGATGGGGA TACTGACTACAATGGGAAATTCAAGGGCAGAGTC ACAATTACCGCCGACAAATCCACTAGCACAGCCT ATATGGAGCTGAGCAGCCTGAGATCTGAGGACAC GGCCGTGTATCTGTGTGCAAGAAATGTCTTTGAT GGTTACTGGCTTGTTTACTGGGGCCAGGGAACCC TGGTCACCGTCTCCTCAGCTAGCACC | 33 |
| B-HH4 | CAGGTGCAATTGGTGCAGTCTGGCGCTGAAGTTA AGAAGCCTGGAGCTTCAGTGAAGGTCTCCTGCAA GGTCTCCGGATACGCGTTCAGCTATTCTTGGATG AACTGGGTGCGGCAGGCCCCTGGACAAGGGCTCG AGTGGATGGGACGGATCTTTCCCGGCGATGGGGA TACTGACTACAATGGGAAATTCAAGGGCAGAGTC ACAATTACCGCCGAGAAATCCACTAGCACAGCCT ATATGGAGCTGAGCAGCCTGAGATCTGAGGACAC GGCCGTGTATTACTGTGCAAGAAATGTCTTTGAT GGTTACTGGCTTGTTTACTGGGGCCAGGGAACCC TGGTCACCGTCTCCTCA | 35 |
| B-HH5 | CAGGTGCAATTGGTGCAGTCTGGCGCTGAAGTTA AGAAGCCTGGGAGTTCAGTGAAGGTCTCCTGCAA GGCTTCCGGATACGCGTTCAGCTATTCTTGGATG AGCTGGGTGCGGCAGGCGCCTGGACAAGGGCTCG AGTGGATGGGACGGATCTTTCCCGGCGATGGGGA TACTGACTACAATGGGAAATTCAAGGGCAGAGTC ACAATTACCGCCGACAAATCCACTAGCACAGCCT ATATGGAGCTGAGCAGCCTGAGATCTGAGGACAC GGCCGTGTATTACTGTGCAAGAAATGTCTTTGAT GGTTACTGGCTTGTTTACTGGGGCCAGGGAACCC TGGTCACCGTCTCCTCA | 37 |
| B-HH6 | CAGGTGCAATTGGTGCAGTCTGGCGCTGAAGTTA AGAAGCCTGGGAGTTCAGTGAAGGTCTCCTGCAA GGCTTCCGGATACGCCTTCAGCTATTCTTGGATC AATTGGGTGCGGCAGGCGCCTGGACAAGGGCTCG AGTGGATGGGACGGATCTTTCCCGGCGATGGGGA TACTGACTACAATGGGAAATTCAAGGGCAGAGTC ACAATTACCGCCGACAAATCCACTAGCACAGCCT ATATGGAGCTGAGCAGCCTGAGATCTGAGGACAC GGCCGTGTATTACTGTGCAAGAAATGTCTTTGAT GGTTACTGGCTTGTTTACTGGGGCCAGGGAACCC TGGTCACCGTCTCCTCA | 39 |
| B-HH7 | CAGGTGCAATTGGTGCAGTGTGGCGCTGAAGTTA AGAAGCCTGGGAGTTCAGTGAAGGTCTCCTGCAA GGCTTCCGGATACGCCTTCAGGTATTCTTGGATC TCGTGGGTGCGGCAGGCGCCTGGACAAGGGCTCG AGTGGATGGGACGGATCTTTCCCGGCGATGGGGA TACTGACTACAATGGGAAATTCAAGGGCAGAGTC ACAATTACCGCCGACAAATCCACTAGCACAGCCT ATATGGAGCTGAGCAGCCTGAGATCTGAGGACAC GGCCGTGTATTACTGTGCAAGAAATGTCTTTGAT GGTTACTGGCTTGTTTACTGGGGCCAGGGAACCC TGGTCACCGTCTCCTCA | 41 |
| B-HH8 | CAGGTGCAATTGGTGCAGTCTGGCGCTGAAGTTA AGAAGCCTGGCGCCTCAGTGAAGGTCTCCTGCAA GGCTTCCGGATACACCTTCACATACAGCTGGATG AACTGGGTGCGGCAGGCCCCTGGACAAGGGCTCG AGTGGATGGGACGGATCTTTCCCGGCGATGGGGA TACTGACTACAATGGGAAATTCAAGGGCAGAGTC ACAATTACCGCCGACAAATCCACTAGCACAGCCT ATATGGAGCTGAGCAGCCTGAGATCTGAGGACAC GGCCGTGTATTACTGTGCAAGAAATGTCTTTGAT GGTTACTGGCTTGTTTACTGGGGCCAGGGAACCC TGGTCACCGTCTCCTCA | 43 |

TABLE 2-continued

| CONSTRUCT | NUCLEOTIDE SEQUENCE | SEQ ID NO |
|---|---|---|
| B-HH9 | CAGGTGCAATTGGTGCAGTCTGGCGCTGAAGTTA AGAAGCCTGGCGCCTCAGTGAAGGTCTCCTGCAA GGCTTCCGGATACACCTTCAGCTATTCTTGGATG AACTGGGTGCGGCAGGCCCCTGGACAAGGGCTCG AGTGGATGGGACGGATCTTTCCCGGCGATGGGGA TACTGACTACAATGGGAAATTCAAGGGCAGAGTC ACAATTACCGCCGACAAATCCACTAGCACAGCCT ATATGGAGCTGAGCAGCCTGAGATCTGAGGACAC GGCCGTGTATTACTGTGCAAGAAATGTCTTTGAT GGTTACTGGCTTGTTTACTGGGGCCAGGGAACCC TGGTCACCGTCTCCTCA | 45 |
| B-HL1 | CAGGTGCAATTGGTGCAGTCTGGCGCTGAAGTTA AGAAGCCTGGGGCCTCAGTGAAGGTCTCCTGCAA GGCTTCCGGATACACCTTCACCTATTCTTGGATG CACTGGGTGCGGCAGGCCCCTGGACAAGGGCTCG AGTGGATGGGACGGATCTTTCCCGGCGATGGGGA TACTGACTACACAGAAATTCAAGGAAGAGTC ACAATGACACGGGACACGTCCACTTCCACCGTCT ATATGGAGCTGAGCAGCCTGAGATCTGAGGACAC GGCCGTGTATTACTGTGCAAGAAATGTCTTTGAT GGTTACTGGCTTGTTTACTGGGGCCAGGGAACCC TGGTCACCGTCTCCTGA | 47 |
| B-HL2 | GAGGTGCAATTGGTGCAGTCTGGCGCTGAAGTTA AGAAGCCTGGGGCCACCGTGAAGATCTCCTGCAA GGTGTCCGGATACACCTTCACCTATTCTTGGATG CACTGGGTGCAGCAGGCCCCTGGAAAGGGGCTCG AGTGGATGGGACGGATCTTTCCCGGCGATGGGGA TACTGACTACGCAGAGAAATTCCAAGGAAGAGTC ACAATCACAGCCGACAGTCCACTGACACCGCCT ATATGGAGCTGAGCAGCCTGAGATCTGAGGACAC GGCCGTGTATTACTGTGCAACCAATGTCTTTGAT GGTTACTGGCTTGTTTACTGGGGCCAGGGAACCC TGGTCACCGTCTCCTCA | 49 |
| B-HL3 | GAGGTGCAATTGGTGCAGTCTGGCGCTGAAGTTA AGAAGCCTGGGGCCACCGTGAAGATCTCCTGCAA GGTGTCCGGATACACCTTCACCTATTCTTGGATG CACTGGGTGCAGCAGGCCCCTGGAAAGGGGCTCG AGTGGATGGGACGGATCTTTCCCGGCGATGGGGA TACTGACTACGCAGAGAAATTCCAAGGAAGAGTC ACAATCACAGCCGACAGTCCACTGACACCGCCT ATATGGAGCTGAGCAGCCTGAGATCTGAGGACAC GGCCGTGTATTACTGTGCAACCAATGTCTTTGAT GGTTACTGGCTTGTTTACTGGGGCCAGGGAACCC TGGTCACCGTCTCCTCA | 51 |
| B-HL4 | CAGATGCAATTGGTGCAGTCTGGCGCTGAAGTTA AGAAGACCGGGAGTTCAGTGAAGGTCTCCTGCAA GGCTTCCGGATACACCTTCACCTATTCTTGGATG AGCTGGGTGCGGCAGGCCCCTGGACAAGGGCTCG AGTGGATGGGACGGATCTTTCCCGGCGATGGGGA TACTGACTACGCACAGAAATTCCAAGGAAGAGTC ACAATTACCGCCGACAAATCCACTAGCACAGCCT ATATGGAGCTGAGCAGCCTGAGATCTGAGGACAC GGCCGTGTATTACTGTGCAAGAAATGTCTTTGAT GGTTACTGGCTTGTTTACTGGGGCCAGGGAACCC TGGTCACCGTGTCCTCAGCTAGCACC | 53 |
| B-HL8 | GAAGTGCAGCTGGTGGAGTCTGGAGGAGGCTTGG TCAAGCCTGGCGGGTCCCTGCGGCTCTCCTGTGC AGCCTCTGGATTCACATTTAGCTATTCTTGGATG AACTGGGTGCGGCAGGCCCCTGGAAAGGGCTCG AGTGGGTGGGACGGATCTTTCCCGGCGATGGGGA TACTGACTACAATGGGAAATTCAAGGGCAGAGTC ACAATTACCGCCGACAAATCCACTAGCACAGCCT ATATGGAGCTGAGCAGCCTGAGATCTGAGGACAC GGCCGTGTATTACTGTGCAAGAAATGTGTTTGAT GGTTACTGGCTTGTTTACTGGGGCCAGGGAACCC TGGTCACCGTCTCCTCA | 55 |
| B-HL10 | CGGAATTCGGCCCACCGGTGGCCACCATGGACTG GACCTGGAGGATCCTCTTCTTGGTGGCAGCAGCC AGAGGAGCCCAGTCCGAAGTGCAGCTGGTGGAGT CTGGAGGAGGCTTGGTCAAGCCTGGCGGGTCCCT GCGGCTCTCCTGTGCAGCCTCTGGATTCGCATTC AGCTATTCTTGGATGAACTGGGTGCGGCAGGCTC CTGGAAAGGGCCTCGAGTGGGTGGGACGGATCTT TCCCGGCGATGGGGATACTGACTACAATGGGAAA TTCAAGGGCAGAGTCACAATTACCGCCGACAAAT CCACTAGCACAGCCTATATGGAGCTGAGCAGCCT GAGATCTGAGGACACGGCCGTGTATTACTGTGCA AGAAATGTCTTTGATGGTTACTGGCTTGTTTACT GGGGCCAGGGAACCCTGGTCACCGTCTCCTCAGC TAGCGAATTCTCGA | 57 |
| B-HL11 | CAGGTGCAGCTGGTGGAGTCTGGAGGAGGCTTGG TCAAGCCTGGCGGGTCCCTGCGGCTGTCCTGTGC AGCCTCTGGATCACATTTAGCTATTCTTGGATGA ACTGGGTGCGGCAGGCTCCTGGAAAGGGCCTCGA GTGGGTGGGACGGATCTTTCCCGGCGATGGGGAT ACTGACTACAATGGGAAATTCAAGGGCAGAGTCA CAATTACCGCCGACAAATCCACTAGCACAGCCTA TATGGAGCTGAGCAGCCTGAGATCTGAGGACACG GCCGTGTATTACTGTGCAAGAAATGTCTTTGATG GTTACTGGCTTGTTTACTGGGGCCAGGGAACCCT GGTCACCGTCTCCTCA | 59 |
| B-HL12 | CGGAATTCGGCCCACCGGTGGCCACCATGGACTG GACCTGGAGGATCCTCTTCTTGGTGGCAGCAGCC AGAGGAGCCCAGTCCGAAGTCAGCTGGTGGAGT CTGGAGGAGGCTTGGTCAAGCCTGGCGGGTCCCT GCGGCTCTCCTGTGCAGCCTCTGGATTCGCATTC AGCTATTCTTGGATGAACTGGGTGCGGCAGGCTC CTGGAAAGGGCCTCGAGTGGGTGGGACGGATCTT TCCCGGCGATGGGGATACTGACTACAATGGGAAA TTCAAGGGCAGAGTCACAATTACCGCCGACAAAT CCACTAGCACAGCCTATATGGAGCTGAGCAGCCT GAGATCTGAGGACACGGCCGTGTATTACTGTGCA AGAAATGTCTTTGATGGTTACTGGCTTGTTTACT GGGGCCAGGGAACCCTGGTCACCGTCTCCTCAGC TAGCGAATTCTCGA | 61 |
| B-HL13 | CGGAATTCGGCCCACCGGTGGCCACCATGGACTG GACCTGGAGGATCCTCTTCTTGGTGGCAGCAGCC AGAGGAGCCCAGTCCGAAGTCAGCTGGTGGAGT CTGGAGGAGGCTTGGTCAAGCCTGGCGGGTCCCT GCGGCTCTCCTGTGCAGCCTCTGGATTCGCATTC AGCTATTCTTGGATGAACTGGGTGCGGCAGGCTC CTGGAAAGGGCCTCGAGTGGGTGGGACGGATCTT TCCCGGCGATGGGGATACTGACTACAATGGGAAA TTCAAGGGCAGAGTCACAATTACCGCCGACAAAT CCACTAGCACAGCCTATATGGAGCTGAGCAGCCT GAGATCTGAGGACACGGCCGTGTATTACTGTGCA AGAAATGTCTTTGATGGTTACTGGCTTGTTTACT GGGGCCAGGGAACCCTGGTCACCGTCTCCTCAGC TAGCGAATTCTCGA | 63 |
| B-HL14 | CGGAATTCGGCCCACCGGTGGCCACCATGGACTG GACCTGGAGGATCCTCTTCTTGGTGGCAGCAGCC AGAGGAGCCCAGTCCGAAGTCAGCTGGTGGAGT CTGGAGGAGGCTTGGTCAAGCCTGGCGGGTCCCT GCGGCTCTCCTGTGCAGCCTCTGGATTCGCATTC AGCTATTCTTGGATGAACTGGGTGCGGCAGGCTC CTGGAAAGGGCCTCGAGTGGGTGGGACGGATCTT TCCCGGCGATGGGGATACTGACTACAATGGGAAA TTCAAGGGCAGAGTCACAATTACCGCCGACAAAT CCACTAGCACAGCCTATATGGAGCTGAGCAGCCT GAGATCTGAGGACACGGCCGTGTATTACTGTGCA AGAAATGTCTTTGATGGTTACTGGCTTGTTTACT GGGGCCAGGGAACCCTGGTCACCGTCTCCTCAGC TAGCGAATTCTCGA | 65 |
| B-HL15 | CGGAATTCGGCCCACCGGTGGCCACCATGGACTG GACCTGGAGGATCCTCTTCTTGGTGGCAGCAGCC AGAGGAGCCCAGTCCGAAGTCAGCTGGTGGAGT CTGGAGGAGGCTTGGTCAAGCCTGGCGGGTCCCT GCGGCTCTCCTGTGCAGCCTCTGGATTCGCATTC AGCTATTCTTGGATGAACTGGGTGCGGCAGGCTC CTGGAAAGGGCCTCGAGTGGGTGGGACGGATCTT TCCCGGCGATGGGGATACTGACTACAATGGGAAA TTCAAGGGCAGAGTCACAATTACCGCCGACAAAT CCACTAGCACAGCCTATATGGAGCTGAGCAGCCT | 67 |

TABLE 2-continued

| CONSTRUCT | NUCLEOTIDE SEQUENCE | SEQ ID NO |
|---|---|---|
| | GAGATCTGAGGACACGGCCGTGTATTACTGTGCA AGAAATGTCTTTGATGGTTACTGGCTTGTTTACT GGGGCCAGGGAACCCTGGTCACCGTCTCCTCAGC TAGCGAATTCTCGA | |
| B-HL16 | CGGAATTCGGCCCACCGGTGGCCACCATGGACTG GACCTGGAGGATCCTCTTCTTGGTGGCAGCAGCC AGAGGAGCCCAGTCCGAAGTGCAGCTGGTGGAGT CTGGAGGAGGCTTGGTCAAGCCTGGCGGGTCCCT GCGGCTCTCCTGTGCAGCCTCTGGATTCGCATTC AGCTATTCTTGGATGAACTGGGTGCGGCAGGCTC CTGGAAAGGGCCTCGAGTGGGTGGGACGGATCTT TCCCGGCGATGGGGATACTGACTACAATGGGAAA TTCAAGGGCAGAGTCACAATTACCGCCGACAAAT CCACTAGCACAGCCTATATGGAGCTGAGCAGCCT GAGATCTGAGGACACGGCCGTGTATTACTGTGCA AGAAATGTCTTTGATGGTTACTGGCTTGTTTACT GGGGCCAGGGAACCCTGGTCACCGTCTCCTCAGC TAGCGAATTCTCGA | 69 |
| B-HL17 | CGGAATTCGGCCCACCGGTGGCCACCATGGACTG GACCTGGAGGATCCTCTTCTTGGTGGCAGCAGCC AGAGGAGCCCAGTCCGAAGTGCAGCTGGTGGAGT CTGGAGGAGGCTTGGTCAAGCCTGGCGGGTCCCT GCGGCTCTCCTGTGCAGCCTCTGGATTCGCATTC AGCTATTCTTGGATGAACTGGGTGCGGCAGGCTC CTGGAAAGGGCCTCGAGTGGGTGGGACGGATCTT TCCCGGCGATGGGGATACTGACTACAATGGGAAA TTCAAGGGCAGAGTCACAATTACCGCCGACAAAT CCACTAGCACAGCCTATATGGAGCTGAGCAGCCT GAGATCTGAGGACACGGCCGTGTATTACTGTGCA AGAAATGTCTTTGATGGTTACTGGCTTGTTTACT GGGGCCAGGGAACCCTGGTCACCGTCTCCTCAGC TAGCGAATTCTCGA | 71 |
| VH Signal Sequence | ATGGACTGGAGCTGGAGGATCCTCTTCTTGGTGG CAGCAGCCACAGGAGCCCACTCC | 73 |
| B-KV1 | GATATCGTGATGACCCAGACTCCACTCTCCCTGC CCGTCACCCCTGGAGAGCCCGCCAGCATTAGCTG CAGGTCTAGCAAGAGCCTCTTGCACAGCAATGGC ATCACTTATTTGTATTGGTACCTGCAAAAGCCAG GGCAGTCTCCACAGCTCCTGATTTATCAAATGTC CAACCTTGTCTCTGGCGTCCCTGACCGGTTCTCC GGATCCGGGTCAGGCACTGATTTCACACTGAAAA TCAGCAGGGTGGAGGCTGAGGATGTTGGAGTTTA TTACTGCGCTCAGAATCTAGAACTTCCTTACACC TTCGGCGGAGGGACCAAGGTGGAGATCAAACGTA CGGTG | 75 |
| VL Signal Sequence | ATGGACATGAGGGTCCCCGCTGAGCTCCTGGGCC TGCTGCTGCTCTGGTTCCCAGGTGCCAGGTGT | 77 |

TABLE 3

| CONSTRUCT | AMINO ACID SEQUENCE | SEQ ID NO |
|---|---|---|
| B-HH1 | QVQLVQSGAEVKKPGSSVKVSCKASGYTFSYSW MSWVRQAPGQGLEWMGRIFPGDGDTDYAQKFQG RVTITADKSTSTAYMELSSLRSEDTAVYYCARN VFDGYWLVYWGQGTLVTVSS | 30 |
| B-HH2 | QVQLVQSGAEVKKPGSSVKVSCKASGYTFSYSW MNWVRQAPGQGLEWMGRIFPGDGDTDYNGKFKG RVTITADKSTSTAYMELSSLRSEDTAVYYCARN VFDGYWLVYWGQGTLVTVSS | 32 |
| B-HH3 | QVQLVQSGAEVKKPGSSVKVSCKASGYTFSYSW MNWVRQAPGQGLEWMGRIFPGDGDTDYNGKFKG RVTITADKSTSTAYMELSSLRSEDTAVYYCARN VFDGYWLVYWGQGTLVTVSS | 34 |

TABLE 3-continued

| CONSTRUCT | AMINO ACID SEQUENCE | SEQ ID NO |
|---|---|---|
| B-HH4 | QVQLVQSGAEVKKPGSSVKVSCKASGYTFSYSW MNWVRQAPGQGLEWMGRIFPGDGDTDYNGKFKG RVTITADKSTSTAYMELSSLRSEDTAVYYCARN VFDGYWLVYWGQGTLVTVSS | 36 |
| B-HH5 | QVQLVQSGAEVKKPGSSVKVSCKASGYTFSYSW MSWVRQAPGQGLEWMGRIFPGDGDTDYNGKFKG RVTITADKSTSTAYMELSSLRSEDTAVYYCARN VFDGYWLVYWGQGTLVTVSS | 38 |
| B-HH6 | QVQLVQSGAEVKKPGSSVKVSCKASGYTFSYSW INWVRQAPGQGLEWMGRIFPGDGDTDYNGKFKG RVTITADKSTSTAYMELSSLRSEDTAVYYCARN VFDGYWLVYWGQGTLVTVSS | 40 |
| B-HH7 | QVQLVQSGAEVKKPGSSVKVSCKASGYTFSYSW ISWVRQAPGQGLEWMGRIFPGDGDTDYNGKFKG RVTITADKSTSTAYMELSSLRSEDTAVYYCARN VFDGYWLVYWGQGTLVTVSS | 42 |
| B-HH8 | QVQLVQSGAEVKKPGSSVKVSCKASGYTFSYSW MNWVRQAPGQGLEWMGRIFPGDGDTDYNGKFKG RVTITADKSTSTAYMELSSLRSEDTAVYYCARN VFDGYWLVYWGQGTLVTVSS | 44 |
| B-HH9 | QVQLVQSGAEVKKPGSSVKVSCKASGYTFSYSW MNWVRQAPGQGLEWMGRIFPGDGDTDYNGKFKG RVTITADKSTSTAYMELSSLRSEDTAVYYCARN VFDGYWLVYWGQGTLVTVSS | 46 |
| B-HL1 | QVQLVQSGAEVKKPGSSVKVSCKASGYTFSYSW MHWVRQAPGQGLEWMGRIFPGDGDTDYAQKFQG RVTMTRDTSTSTVYMELSSLRSEDTAVYYCARN VFDGYWLVYWGQGTLVTVSS | 48 |
| B-HL2 | QVQLVQSGAEVKKPGSSVKVSCKASGYTFSYSW MHWVQQAPGQGLEWMGRIFPGDGDTDYAEKFQG RVTITADTSTDTAYMELSSLRSEDTAVYYCATN VFDGYWLVYWGQGTLVTVSS | 50 |
| B-HL3 | QVQLVQSGAEVKKPGSSVKVSCKASGYTFSYSW MHWVQQAPGQGLEWMGRIFPGDGDTDYNGKFQG RVTMADTSTDTAYMELSSLRSEDTAVYYCATN VFDGYWLVYWGQGTLVTVSS | 52 |
| B-HL4 | QVQLVQSGAEVKKTGSSVKVSCKASGYTFTYSW MSWVRQAPGQGLEWMGRIFPGDGDTDYAQKFQG RVTITADKSTSTAYMELSSLRSEDTAVYYCARN VFDGYWLVYWGQGTLVTVSS | 54 |
| B-HL8 | QVQLVQSGGGLVKPGSSLRLSCAASGFTFSYSW MNWVRQAPGKGLEWVGRIFPGDGDTDYNGKFKG RVTITADKSTSTAYMELSSLRSEDTAVYYCARN VFDGYWLVYWGQGTLVTVSS | 56 |
| B-HL10 | EVQLVESGGGLVKPGSSLRLSCAASGFAFSYSW MNWVRQAPGKGLEWVGRIFPGDGDTDYNGKFKG RVTITADKSTSTAYMELSSLRSEDTAVYYCARN VFDGYWLVYWGQGTLVTVSS | 58 |
| B-HL11 | QVQLVESGGGLVKPGSSLRLSCAASGFTFSYSW MNWVRQAPGKGLEWVGRIFPGDGDTDYNGKFKG RVTITADKSTSTAYMELSSLRSEDTAVYYCARN VFDGYWLVYWGQGTLVTVSS | 60 |
| B-HL12 | EVQLVESGGGLVKPGSSLRLSCAASGFTFSYSW MNWVRQAPGKGLEWVGRIFPGDGDTDYNGKFKG RVTITADKSTSTAYMELSSLRSEDTAVYYCARN VFDGYWLVYWGQGTLVTVSS | 62 |
| B-HL13 | EVQLVESGGGLVVPGSSLRLSCAASGFTFSYSW MNWVRQAPGKGLEWVGRIFPGDGDTDYNGKFKG RVTITADKSTSTAYMELSSLRSEDTAVYYCARN VFDGYWLVYWGQGTLVTVSS | 64 |

TABLE 3-continued

| CONSTRUCT | AMINO ACID SEQUENCE | SEQ ID NO |
|---|---|---|
| B-HL14 | EVQLVESGGGLKKPGGSLRLSCAASGFTFSYSW MNWVRQAPGKGLEWMGRIFPGDGDTDYNGKFKG RVTITADKSTSTAYMELSSLRSEDTAVYYCARN VFDGYWLVYWGQGTLVTVSS | 66 |
| B-HL15 | EVQLVESGGGLVKPGGSLRLSCAASGFTFSYSW MNWVRQAPGKGLEWMGRIFPGDGDTDYNGKFKG RVTITADKSTSTAYMELSSLRSEDTAVYYCARN VFDGYWLVYWGQGTLVTVSS | 68 |
| B-HL16 | EVQLVESGGGLVKPGGSLRVSCAASGFTFSYSW MNWVRQAPGKGLEWMGRIFPGDGDTDYNGKFKG RVTITADKSTSTAYMELSSLRSEDTAVYYCARN VFDGYWLVYWGQGTLVTVSS | 70 |
| B-HL17 | EVQLVESGGGLVKPGGSLRLSCAASGFTFSYSW MNWVRQAPGKGLEWMGRIFPGDGDTDYNGKFKG RVTITADKSTSTAYMELSSLRSEDTAVYYCARN VFDGYWLVYWGQGTLVTVSS | 72 |
| VH Signal Sequence | MDWTWRILFLVAAATGAHS | 74 |
| B-KV1 | DIYMTQTPLSLPVTPGEPASISGRSSKSLLHSNG ITYLYWYLQKPGQSPQLLIYQMSNLVSGVPDRFS GSGSGTDFTLKISRVEAEDVGVYYCAQNLELPYT FGGGTKVEIKRTV | 76 |
| VL Signal Sequence | MDMRVPAQLLGLLLLWFPGARC | 78 |

Figure 5B:
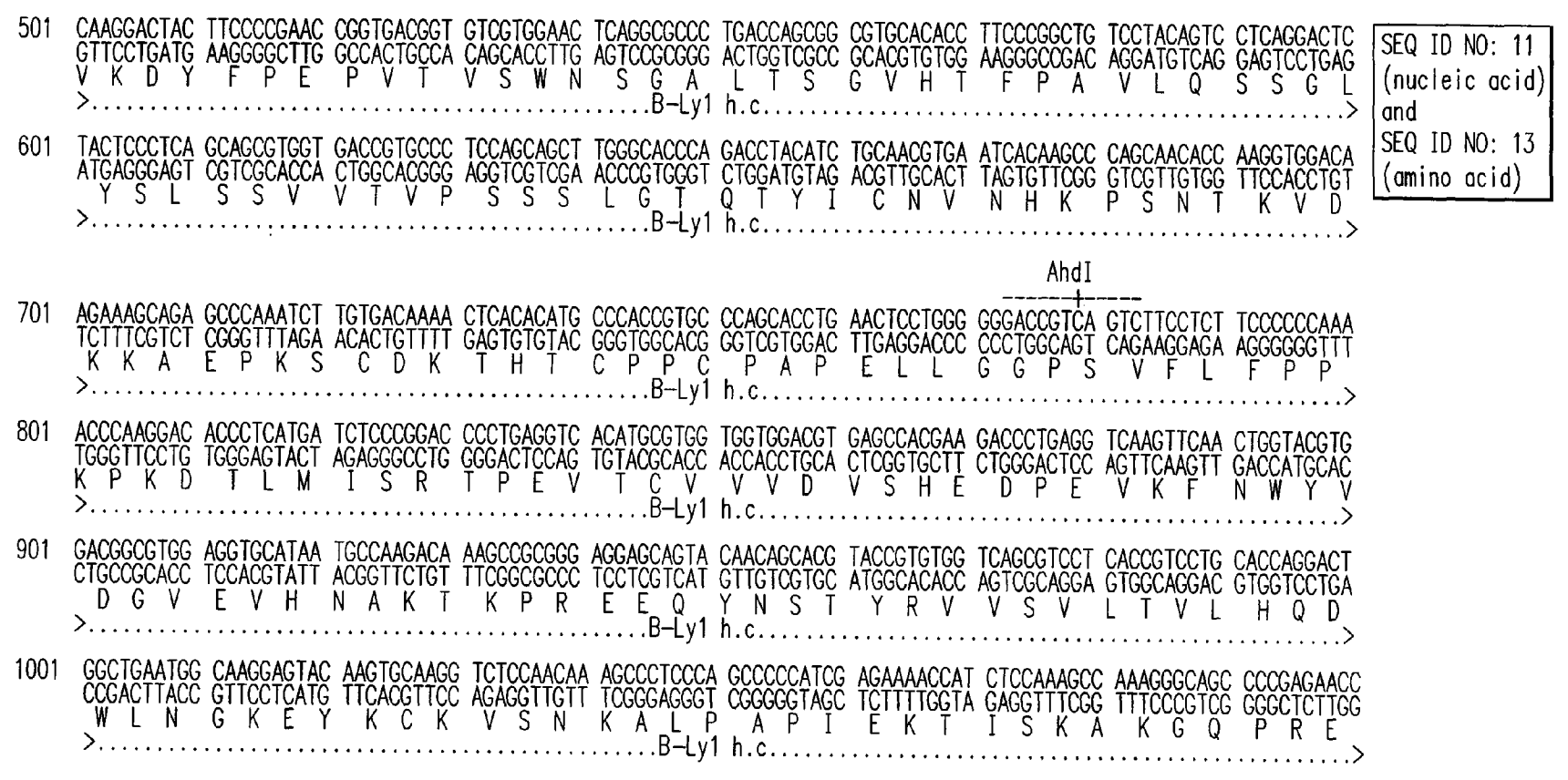

In another preferred embodiment, the present invention is directed to an isolated polynucleotide comprising a sequence that encodes a polypeptide having the amino acid sequence shown in FIG. 1 or FIG. 2. The invention is further directed to an isolated nucleic acid comprising a sequence at least 80%, 85%, 90%, 95%, 96%, 97%, 98% or 99% identical to the nucleotide sequence shown in FIG. 5 or FIG. 6. In another embodiment, the invention is directed to an isolated nucleic acid comprising a sequence that encodes a polypeptide having an amino acid sequence at least 80%, 85%, 90%, 95%, 96%, 97%, 98% or 99% identical to the amino acid sequence FIG. 5 or FIG. 6. The invention also encompasses an isolated nucleic acid comprising a sequence that encodes a polypeptide having the amino acid sequence of any of FIG. 1, FIG. 2, FIG. 5 or FIG. 6 with conservative amino acid substitutions.

In another embodiment, the present invention is directed to an expression vector and/or a host cell which comprise one or more isolated polynucleotides of the present invention.

Generally, any type of cultured cell line can be used to express the ABM of the present invention. In a preferred embodiment, CHO cells, BHK cells, NS0 cells, SP2/0 cells, YO myeloma cells, P3X63 mouse myeloma cells, PER cells, PER.C6 cells or hybridoma cells, other mammalian cells, yeast cells, insect cells, or plant cells are used as the background cell line to generate the engineered host cells of the invention.

The therapeutic efficacy of the ABMs of the present invention can be enhanced by producing them in a host cell that further expresses a polynucleotide encoding a polypeptide having GnTIII activity. In a preferred embodiment, the polypeptide having GnTIII activity is a fusion polypeptide comprising the Golgi localization domain of a Golgi resident polypeptide. In another preferred embodiment, the expression of the ABMs of the present invention in a host cell that expresses a polynucleotide encoding a polypeptide having GnTIII activity results in ABMs with increased Fc receptor binding affinity and increased effector function. Accordingly, in one embodiment, the present invention is directed to a host cell comprising (a) an isolated nucleic acid comprising a sequence encoding a polypeptide having GnTIII activity; and (b) an isolated polynucleotide encoding an ABM of the present invention, such as a chimeric, primatized or humanized antibody that binds human CD20. In a preferred embodiment, the polypeptide having GnTIII activity is a fusion polypeptide comprising the catalytic domain of GnTIII and the Golgi localization domain is the localization domain of mannosidase II. Methods for generating such fusion polypeptides and using them to produce antibodies with increased effector functions are disclosed in U.S. Provisional Pat. Appl. No. 60/495,142, the entire contents of which are expressly incorporated herein by reference. In another preferred embodiment, the chimeric ABM is a chimeric antibody or a fragment thereof, having the binding specificity of the murine B-LY1 antibody. In a particularly preferred embodiment, the chimeric antibody comprises a human Fc. In another preferred embodiment, the antibody is primatized or humanized.

In one embodiment, one or several polynucleotides encoding an ABM of the present invention may be expressed under the control of a constitutive promoter or, alternately, a regulated expression system. Suitable regulated expression systems include, but are not limited to, a tetracycline-regulated expression system, an ecdysone-inducible expression system, a lac-switch expression system, a glucocorticoid-inducible expression system, a temperature-inducible promoter system, and a metallothionein metal-inducible expression system. If several different nucleic acids encoding an ABM of the present invention are comprised within the host cell system, some of them may be expressed under the control of a constitutive promoter, while others are expressed under the control of a regulated promoter. The maximal expression level is considered to be the highest possible level of stable polypeptide expression that does not have a significant adverse effect on cell growth rate, and will be determined using routine experimentation. Expression levels are determined by methods generally known in the art, including Western blot analysis using an antibody specific for the ABM or an antibody specific for a peptide tag fused to the ABM; and Northern blot analysis. In a further alternative, the polynucleotide may be operatively linked to a reporter gene; the expression levels of a chimeric ABM having substantially the same binding specificity of the murine B-Ly1 antibody are determined by measuring a signal correlated with the expression level of the reporter gene. The reporter gene may be transcribed together with the nucleic acid(s) encoding said fusion polypeptide as a single mRNA molecule; their respective coding sequences may be linked either by an internal ribosome entry site (IRES) or by a cap-independent translation enhancer (CITE). The reporter gene may be translated together with at least one nucleic acid encoding a chimeric ABM having substantially the same binding specificity of the murine B-Ly1 antibody such that a single polypeptide chain is formed. The nucleic acids encoding the AMBs of the present invention may be operatively linked to the reporter gene under the control of a single promoter, such that the nucleic acid encoding the fusion polypeptide and the reporter gene are transcribed into an RNA molecule which is alternatively spliced into two separate messenger RNA (mRNA) molecules; one of the resulting mRNAs is translated into said reporter protein, and the other is translated into said fusion polypeptide.

Methods which are well known to those skilled in the art can be used to construct expression vectors containing the coding sequence of an ABM having substantially the same binding specificity of the murine B-Ly1 antibody along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING A LABORATORY MANUAL, Cold Spring Harbor Laboratory, N.Y. (1989) and Ausubel et al., CURRENT PROTOCOLS IN MOLECULAR BIOLOGY, Greene Publishing Associates and Wiley Interscience, N.Y. (1989).

A variety of host-expression vector systems may be utilized to express the coding sequence of the ABMs of the present invention. Preferably, mammalian cells are used as host cell systems transfected with recombinant plasmid DNA or cosmid DNA expression vectors containing the coding sequence of the protein of interest and the coding sequence of the fusion polypeptide. Most preferably, CHO cells, BHK cells, NS0 cells, SP2/0 cells, YO myeloma cells, P3X63 mouse myeloma cells, PER cells, PER.C6 cells or hybridoma cells, other mammalian cells, yeast cells, insect cells, or plant cells are used as host cell system. Some examples of expression systems and selection methods are described in the following references, and references therein: Borth et al., *Biotechnol. Bioen.* 71(4):266-73 (2000-2001), in Werner et al., *Arzneimittelforschung/Drug Res.* 48(8):870-80 (1998), in Andersen and Krummen, *Curr. Op. Biotechnol.* 13:117-123 (2002), in Chadd and Chamow, *Curr. Op. Biotechnol.* 12:188-194 (2001), and in Giddings, *Curr. Op. Biotechnol.* 12: 450-454 (2001). In alternate embodiments, other eukaryotic host cell systems may be contemplated, including yeast cells transformed with recombinant yeast expression vectors containing the coding sequence of an ABM of the present invention; insect cell systems infected with recombinant virus expression vectors (e.g., baculovirus) containing the coding sequence of a chimeric ABM having substantially the same binding specificity of the murine B-Ly1 antibody; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the coding sequence of the ABM of the invention; or animal cell systems infected with recombinant virus expression vectors (e.g., adenovirus, vaccinia virus) including cell lines engineered to contain multiple copies of the DNA encoding a chimeric ABM having substantially the same binding specificity of the murine B-Ly1 antibody either stably amplified (CHO/dhfr) or unstably amplified in double-minute chromosomes (e.g., murine cell lines). In one embodiment, the vector comprising the polynucleotide(s) encoding the ABM of the invention is polycistronic. Also, in one embodiment the ABM discussed above is an antibody or a fragment thereof. In a preferred embodiment, the ABM is a humanized antibody.

For the methods of this invention, stable expression is generally preferred to transient expression because it typically achieves more reproducible results and also is more amenable to large-scale production. Rather than using expression vectors which contain viral origins of replication, host cells can be transformed with the respective coding nucleic acids controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched media, and then are switched to a selective media. The selectable marker in the recombinant plasmid confers resistance to the selection and allows selection of cells which have stably integrated the plasmid into their chromosomes and grow to form foci which in turn can be cloned and expanded into cell lines.

A number of selection systems may be used, including, but not limited to, the herpes simplex virus thymidine kinase (Wigler et al., *Cell* 11:223 (1977)), hypoxanthine-guanine phosphoribosyltransferase (Szybalska & Szybalski, *Proc. Natl. Acad. Sci. USA* 48:2026 (1962)), and adenine phosphoribosyltransferase (Lowy et al., *Cell* 22:817 (1980)) genes, which can be employed in tk⁻, hgprt⁻ or aprt⁻ cells, respectively. Also, antimetabolite resistance can be used as the basis of selection for dhfr, which confers resistance to methotrexate (Wigler et al., *Natl. Acad. Sci. USA* 77:3567 (1989); O'Hare et al., *Proc. Natl. Acad. Sci. USA* 78:1527 (1981)); gpt, which confers resistance to mycophenolic acid (Mulligan & Berg, *Proc. Natl. Acad. Sci. USA* 78:2072 (1981)); neo, which confers resistance to the aminoglycoside G-418 (Colberre-Garapin et al., *J. Mol. Biol.* 150:1 (1981)); and hygro, which confers resistance to hygromycin (Santerre et al., *Gene* 30:147 (1984) genes. Recently, additional selectable genes have been described, namely trpB, which allows cells to utilize indole in place of tryptophan; hisD, which allows cells to utilize histinol in place of histidine (Hartman & Mulligan, *Proc. Natl. Acad. Sci. USA* 85:8047 (1988)); the glutamine synthase system; and ODC (ornithine decarboxylase) which confers resistance to the ornithine decarboxylase inhibitor, 2-(difluoromethyl)-DL-ornithine, DFMO (McConlogue, *in: Current Communications in Molecular Biology*, Cold Spring Harbor Laboratory ed. (1987)).

The present invention is further directed to a method for modifying the glycosylation profile of the ABMs of the present invention that are produced by a host cell, comprising expressing in said host cell a nucleic acid encoding an ABM of the invention and a nucleic acid encoding a polypeptide with GnTIII activity, or a vector comprising such nucleic acids. Preferably, the modified polypeptide is IgG or a fragment thereof comprising the Fc region. In a particularly preferred embodiment the ABM is a humanized antibody or a fragment thereof.

The modified ABMs produced by the host cells of the invention exhibit increased Fc receptor binding affinity and/or increased effector function as a result of the modification. In a particularly preferred embodiment the ABM is a humanized antibody or a fragment thereof containing the Fc region. Preferably, the increased Fc receptor binding affinity is increased binding to a Fcγ activating receptor, such as the FcγRIIIa receptor. The increased effector function is preferably an increase in one or more of the following: increased antibody-dependent cellular cytotoxicity, increased antibody-dependent cellular phagocytosis (ADCP), increased cytokine secretion, increased immune-complex-mediated antigen uptake by antigen-presenting cells, increased Fc-mediated cellular cytotoxicity, increased binding to NK cells, increased binding to macrophages, increased binding to polymorphonuclear cells (PMNs), increased binding to monocytes, increased crosslinking of target-bound antibodies, increased direct signaling inducing apoptosis, increased dendritic cell maturation, and increased T cell priming.

The present invention is also directed to a method for producing an ABM of the present invention, having modified oligosaccharides in a host cell comprising (a) culturing a host cell engineered to express at least one nucleic acid encoding a polypeptide having GnTIII activity under conditions which permit the production of an ABM according to the present invention, wherein said polypeptide having GnTIII activity is expressed in an amount sufficient to modify the oligosaccharides in the Fc region of said ABM produced by said host cell;

and (b) isolating said ABM. In a preferred embodiment, the polypeptide having GnTIII activity is a fusion polypeptide comprising the catalytic domain of GnTIII. In a particularly preferred embodiment, the fusion polypeptide further comprises the Golgi localization domain of a Golgi resident polypeptide.

Preferably, the Golgi localization domain is the localization domain of mannosidase II or GnTI. Alternatively, the Golgi localization domain is selected from the group consisting of: the localization domain of mannosidase I, the localization domain of GnTII, and the localization domain of a 1-6 core fucosyltransferase. The ABMs produced by the methods of the present invention have increased Fc receptor binding affinity and/or increased effector function. Preferably, the increased effector function is one or more of the following: increased Fc-mediated cellular cytotoxicity (including increased antibody-dependent cellular cytotoxicity), increased antibody-dependent cellular phagocytosis (ADCP), increased cytokine secretion, increased immune-complex-mediated antigen uptake by antigen-presenting cells, increased binding to NK cells, increased binding to macrophages, increased binding to monocytes, increased binding to polymorphonuclear cells; increased direct signaling inducing apoptosis, increased crosslinking of target-bound antibodies, increased dendritic cell maturation, or increased T cell priming. The increased Fc receptor binding affinity is preferably increased binding to Fc activating receptors such as FcγRIIIa. In a particularly preferred embodiment the ABM is a humanized antibody or a fragment thereof.

In another embodiment, the present invention is directed to a chimeric ABM having substantially the same binding specificity of the murine B-Ly1 antibody produced by the methods of the invention which has an increased proportion of bisected oligosaccharides in the Fc region of said polypeptide. It is contemplated that such an ABM encompasses antibodies and fragments thereof comprising the Fc region. In a preferred embodiment, the ABM is a humanized antibody. In one embodiment, the percentage of bisected oligosaccharides in the Fc region of the ABM is at least 50%, more preferably, at least 60%, at least 70%, at least 80%, or at least 90%, and most preferably at least 90-95% of the total oligosaccharides. In yet another embodiment, the ABM produced by the methods of the invention has an increased proportion of nonfucosylated oligosaccharides in the Fc region as a result of the modification of its oligosaccharides by the methods of the present invention. In one embodiment, the percentage of nonfucosylated oligosaccharides is at least 50%, preferably, at least 60% to 70%, most preferably at least 75%. The nonfucosylated oligosaccharides may be of the hybrid or complex type. In a particularly preferred embodiment, the ABM produced by the host cells and methods of the invention has an increased proportion of bisected, nonfucosylated oligosaccharides in the Fc region. The bisected, nonfucosylated oligosaccharides may be either hybrid or complex. Specifically, the methods of the present invention may be used to produce ABMs in which at least 15%, more preferably at least 20%, more preferably at least 25%, more preferably at least 30%, more preferably at least 35% of the oligosaccharides in the Fc region of the ABM are bisected, nonfucosylated. The methods of the present invention may also be used to produce polypeptides in which at least 15%, more preferably at least 20%, more preferably at least 25%, more preferably at least 30%, more preferably at least 35% of the oligosaccharides in the Fc region of the polypeptide are bisected hybrid nonfucosylated.

In another embodiment, the present invention is directed to a chimeric ABM having substantially the same binding specificity of the murine B-Ly1 antibody engineered to have increased effector function and/or increased Fc receptor binding affinity, produced by the methods of the invention. Preferably, the increased effector function is one or more of the following: increased Fc-mediated cellular cytotoxicity (including increased antibody-dependent cellular cytotoxicity), increased antibody-dependent cellular phagocytosis (ADCP), increased cytokine secretion, increased immune-complex-mediated antigen uptake by antigen-presenting cells, increased binding to NK cells, increased binding to macrophages, increased binding to monocytes, increased binding to polymorphonuclear cells, increased direct signaling inducing apoptosis, increased crosslinking of target-bound antibodies, increased dendritic cell maturation, or increased T cell priming. In a preferred embodiment, the increased Fc receptor binding affinity is increased binding to a Fc activating receptor, most preferably FcγRIIIa. In one embodiment, the ABM is an antibody, an antibody fragment containing the Fc region, or a fusion protein that includes a region equivalent to the Fc region of an immunoglobulin. In a particularly preferred embodiment, the ABM is a humanized antibody.

The present invention is further directed to pharmaceutical compositions comprising the ABMs of the present invention and a pharmaceutically acceptable carrier.

The present invention is further directed to the use of such pharmaceutical compositions in the method of treatment of cancer. Specifically, the present invention is directed to a method for the treatment of cancer comprising administering a therapeutically effective amount of the pharmaceutical composition of the invention.

The present invention further provides methods for the generation and use of host cell systems for the production of glycoforms of the ABMs of the present invention, having increased Fc receptor binding affinity, preferably increased binding to Fc activating receptors, and/or having increased effector functions, including antibody-dependent cellular cytotoxicity. The glycoengineering methodology that can be used with the ABMs of the present invention has been described in greater detail in U.S. Pat. No. 6,602,684 and Provisional U.S. Patent Application No. 60/441,307 and WO 2004/065540, the entire contents of each of which is incorporated herein by reference in its entirety. The ABMs of the present invention can alternatively be glycoengineered to have reduced fucose residues in the Fc region according to the techniques disclosed in EP 1 176 195 A1, the entire contents of which is incorporated by reference herein.

Generation of Cell Lines for the Production of Proteins with Altered Glycosylation Pattern The present invention provides host cell expression systems for the generation of the ABMs of the present invention having modified glycosylation patterns. In particular, the present invention provides host cell systems for the generation of glycoforms of the ABMs of the present invention having an improved therapeutic value. Therefore, the invention provides host cell expression systems selected or engineered to express a polypeptide having GnTIII activity. In one embodiment, the polypeptide having GnTIII activity is a fusion polypeptide comprising the Golgi localization domain of a heterologous Golgi resident polypeptide. Specifically, such host cell expression systems may be engineered to comprise a recombinant nucleic acid molecule encoding a polypeptide having GnTIII, operatively linked to a constitutive or regulated promoter system.

In one specific embodiment, the present invention provides a host cell that has been engineered to express at least one nucleic acid encoding a fusion polypeptide having GnTIII activity and comprising the Golgi localization domain of a heterologous Golgi resident polypeptide. In one aspect, the host cell is engineered with a nucleic acid molecule comprising at least one gene encoding a fusion polypeptide having GnTIII activity and comprising the Golgi localization domain of a heterologous Golgi resident polypeptide.

Generally, any type of cultured cell line, including the cell lines discussed above, can be used as a background to engineer the host cell lines of the present invention. In a preferred embodiment, CHO cells, BHK cells, NS0 cells, SP2/0 cells, YO myeloma cells, P3X63 mouse myeloma cells, PER cells, PER.C6 cells or hybridoma cells, other mammalian cells, yeast cells, insect cells, or plant cells are used as the background cell line to generate the engineered host cells of the invention.

The invention is contemplated to encompass any engineered host cells expressing a polypeptide having GnTIII activity, including a fusion polypeptide that comprises the Golgi localization domain of a heterologous Golgi resident polypeptide as defined herein.

One or several nucleic acids encoding a polypeptide having GnTIII activity may be expressed under the control of a constitutive promoter or, alternately, a regulated expression system. Such systems are well known in the art, and include the systems discussed above. If several different nucleic acids encoding fusion polypeptides having GnTIII activity and comprising the Golgi localization domain of a heterologous Golgi resident polypeptide are comprised within the host cell system, some of them may be expressed under the control of a constitutive promoter, while others are expressed under the control of a regulated promoter. Expression levels of the fusion polypeptides having GnTIII activity are determined by methods generally known in the art, including Western blot analysis, Northern blot analysis, reporter gene expression analysis or measurement of GnTIII activity. Alternatively, a lectin may be employed which binds to biosynthetic products of the GnTIII, for example, $E_4$-PHA lectin. Alternatively, a functional assay which measures the increased Fc receptor binding or increased effector function mediated by antibodies produced by the cells engineered with the nucleic acid encoding a polypeptide with GnTIII activity may be used.

Identification of Transfectants or Transformants that Express the Protein Having a Modified Glycosylation Pattern The host cells which contain the coding sequence of a chimeric ABM having substantially the same binding specificity of the murine B-Ly1 antibody and which express the biologically active gene products may be identified by at least four general approaches; (a) DNA-DNA or DNA-RNA hybridization; (b) the presence or absence of "marker" gene functions; (c) assessing the level of transcription as measured by the expression of the respective mRNA transcripts in the host cell; and (d) detection of the gene product as measured by immunoassay or by its biological activity.

In the first approach, the presence of the coding sequence of a chimeric ABM having substantially the same binding specificity of the murine B-Ly1 antibody and the coding sequence of the polypeptide having GnTIII activity can be detected by DNA-DNA or DNA-RNA hybridization using probes comprising nucleotide sequences that are homologous to the respective coding sequences, respectively, or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the coding sequence of the ABM of the invention, or a fragment thereof, and the coding sequence of the polypeptide having GnTIII activity are inserted within a marker gene sequence of the vector, recombinants containing the respective coding sequences can be identified by the absence of the marker gene function. Alternatively, a marker gene can be placed in tandem with the coding sequences under the control of the same or different promoter used to control the expression of the coding sequences. Expression of the marker in response to induction or selection indicates expression of the coding sequence of the ABM of the invention and the coding sequence of the polypeptide having GnTIII activity.

In the third approach, transcriptional activity for the coding region of the ABM of the invention, or a fragment thereof, and the coding sequence of the polypeptide having GnTIII activity can be assessed by hybridization assays. For example, RNA can be isolated and analyzed by Northern blot using a probe homologous to the coding sequences of the ABM of the invention, or a fragment thereof, and the coding sequence of the polypeptide having GnTIII activity or particular portions thereof. Alternatively, total nucleic acids of the host cell may be extracted and assayed for hybridization to such probes.

In the fourth approach, the expression of the protein products can be assessed immunologically, for example by Western blots, immunoassays such as radioimmuno-precipitation, enzyme-linked immunoassays and the like. The ultimate test of the success of the expression system, however, involves the detection of the biologically active gene products.

Generation and Use of ABMs Having Increased Effector Function Including Antibody-Dependent Cellular Cytotoxicity In preferred embodiments, the present invention provides glycoforms of chimeric ABMs having substantially the same binding specificity of the murine B-Ly1 antibody and having increased effector function including antibody-dependent cellular cytotoxicity. Glycosylation engineering of antibodies has been previously described. See, e.g., U.S. Pat. No. 6,602,684, incorporated herein by reference in its entirety.

Clinical trials of unconjugated monoclonal antibodies (mAbs) for the treatment of some types of cancer have recently yielded encouraging results. Dillman, *Cancer Biother. & Radiopharm.* 12:223-25 (1997); Deo et al., *Immunology Today* 18:127 (1997). A chimeric, unconjugated IgG1 has been approved for low-grade or follicular B-cell non-Hodgkin's lymphoma. Dillman, *Cancer Biother. & Radiopharm.* 12:223-25 (1997), while another unconjugated mAb, a humanized IgG1 targeting solid breast tumors, has also been showing promising results in phase II clinical trials. Deo et al., *Immunology Today* 18:127 (1997). The antigens of these two mAbs are highly expressed in their respective tumor cells and the antibodies mediate potent tumor destruction by effector cells in vitro and in vivo. In contrast, many other unconjugated mAbs with fine tumor specificities cannot trigger effector functions of sufficient potency to be clinically useful. Frost et al., *Cancer* 80:317-33 (1997); Surfus et al., *J. Immunother.* 19:184-91 (1996). For some of these weaker mAbs, adjunct cytokine therapy is currently being tested. Addition of cytokines can stimulate antibody-dependent cellular cytotoxicity (ADCC) by increasing the activity and number of circulating lymphocytes. Frost et al., *Cancer* 80:317-33 (1997); Surfus et al., *J. Immunother.* 19:184-91 (1996). ADCC, a lytic attack on antibody-targeted cells, is triggered upon binding of leukocyte receptors to the constant region (Fc) of antibodies. Deo et al., *Immunology Today* 18:127 (1997).

A different, but complementary, approach to increase ADCC activity of unconjugated IgG1s is to engineer the Fc region of the antibody. Protein engineering studies have shown that FcγRs interact with the lower hinge region of the IgG CH2 domain. Lund et al., *J. Immunol.* 157:4963-69 (1996). However, FcγR binding also requires the presence of oligosaccharides covalently attached at the conserved Asn 297 in the CH2 region. Lund et al., *J. Immunol.* 157:4963-69 (1996); Wright and Morrison, *Trends Biotech.* 15:26-31 (1997), suggesting that either oligosaccharide and polypeptide both directly contribute to the interaction site or that the oligosaccharide is required to maintain an active CH2 polypeptide conformation. Modification of the oligosaccharide structure can therefore be explored as a means to increase the affinity of the interaction.

An IgG molecule carries two N-linked oligosaccharides in its Fc region, one on each heavy chain. As any glycoprotein, an antibody is produced as a population of glycoforms which share the same polypeptide backbone but have different oligosaccharides attached to the glycosylation sites. The oligosaccharides normally found in the Fc region of serum IgG are of complex bi-antennary type (Wormald et al., *Biochemistry* 36:130-38 (1997), with a low level of terminal sialic acid and bisecting N-acetylglucosamine (GlcNAc), and a variable degree of terminal galactosylation and core fucosylation. Some studies suggest that the minimal carbohydrate structure required for FcγR binding lies within the oligosaccharide core. Lund et al., *J. Immunol.* 157:4963-69 (1996)

The mouse- or hamster-derived cell lines used in industry and academia for production of unconjugated therapeutic mAbs normally attach the required oligosaccharide determinants to Fc sites. IgGs expressed in these cell lines lack, however, the bisecting GlcNAc found in low amounts in serum IgGs. Lifely et al., *Glycobiology* 318:813-22 (1995). In contrast, it was recently observed that a rat myeloma-produced, humanized IgG1 (CAMPATH-1H) carried a bisecting GlcNAc in some of its glycoforms. Lifely et al., *Glycobiology* 318:813-22 (1995). The rat cell-derived antibody reached a similar maximal in vitro ADCC activity as CAMPATH-1H antibodies produced in standard cell lines, but at significantly lower antibody concentrations.

The CAMPATH antigen is normally present at high levels on lymphoma cells, and this chimeric mAb has high ADCC activity in the absence of a bisecting GlcNAc. Lifely et al., *Glycobiology* 318:813-22 (1995). In the N-linked glycosylation pathway, a bisecting GlcNAc is added by GnTIII. Schachter, *Biochem. Cell Biol.* 64:163-81 (1986).

Previous studies used a single antibody-producing CHO cell line, that was previously engineered to express, in an externally-regulated fashion, different levels of a cloned GnT III gene enzyme (Umana, P., et al., *Nature Biotechnol.* 17:176-180 (1999)). This approach established for the first time a rigorous correlation between expression of GnTIII and the ADCC activity of the modified antibody. Thus, the invention contemplates a recombinant, chimeric antibody or a fragment thereof with the binding specificity of the murine B-Ly1 antibody, having altered glycosylation resulting from increased GnTIII activity. The increased GnTIII activity results in an increase in the percentage of bisected oligosaccharides, as well as a decrease in the percentage of fucose residues, in the Fc region of the ABM. This antibody, or fragment thereof, has increased Fc receptor binding affinity and increased effector function. In addition, the invention is directed to antibody fragment and fusion proteins comprising a region that is equivalent to the Fc region of immunoglobulins.

Therapeutic Applications of ABMs Produced According to the Methods of the Invention.

The ABMs of the present can be used alone to target and kill tumor cells in vivo. The ABMs can also be used in conjunction with an appropriate therapeutic agent to treat human carcinoma. For example, the ABMs can be used in combination with standard or conventional treatment methods such as chemotherapy, radiation therapy or can be conjugated or linked to a therapeutic drug, or toxin, as well as to a lymphokine or a tumor-inhibitory growth factor, for delivery of the therapeutic agent to the site of the carcinoma. The conjugates of the ABMs of this invention that are of prime importance are (1) immunotoxins (conjugates of the ABM and a cytotoxic moiety) and (2) labeled (e.g. radiolabeled, enzyme-labeled, or fluorochrome-labeled) ABMs in which the label provides a means for identifying immune complexes that include the labeled ABM. The ABMs can also be used to induce lysis through the natural complement process, and to interact with antibody dependent cytotoxic cells normally present.

The cytotoxic moiety of the immunotoxin may be a cytotoxic drug or an enzymatically active toxin of bacterial or plant origin, or an enzymatically active fragment ("A chain") of such a toxin. Enzymatically active toxins and fragments thereof used are diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolacca americana* proteins (PAPI, PAPII, and PAP-S), *momordica charantia* inhibitor, curcin, crotin, sapaonaria officinalis inhibitor, gelonin, mitogellin, restrictocin, phenomycin, and enomycin. In another embodiment, the ABMs are conjugated to small molecule anticancer drugs. Conjugates of the ABM and such cytotoxic moieties are made using a variety of bifunctional protein coupling agents. Examples of such reagents are SPDP, IT, bifunctional derivatives of imidoesters such a dimethyl adipimidate HCl, active esters such as disuccinimidyl suberate, aldehydes such as glutaraldehyde, bis-azido compounds such as bis(p-azidobenzoyl) hexanediamine, bis-diazonium derivatives such as bis-(p-diazoniumbenzoyl)-ethylenediamine, diisocyanates such as tolylene 2,6-diisocyanate, and bis-active fluorine compounds such as 1,5-difluoro-2,4-dinitrobenzene. The lysing portion of a toxin may be joined to the Fab fragment of the ABMs. Additional appropriate toxins are known in the art, as evidenced in e.g., published U.S. Patent Application No. 2002/0128448, incorporated herein by reference in its entirety.

In one embodiment, a chimeric, glycoengineered ABM having substantially the same binding specificity of the murine B-Ly1 antibody, is conjugated to ricin A chain. Most advantageously, the ricin A chain is deglycosylated and produced through recombinant means. An advantageous method of making the ricin immunotoxin is described in Vitetta et al., *Science* 238, 1098 (1987), hereby incorporated by reference.

When used to kill human cancer cells in vitro for diagnostic purposes, the conjugates will typically be added to the cell culture medium at a concentration of at least about 10 nM. The formulation and mode of administration for in vitro use are not critical. Aqueous formulations that are compatible with the culture or perfusion medium will normally be used. Cytotoxicity may be read by conventional techniques to determine the presence or degree of cancer.

As discussed above, a cytotoxic radiopharmaceutical for treating cancer may be made by conjugating a radioactive isotope (e.g., I, Y, Pr) to a chimeric, glycoengineered ABM having substantially the same binding specificity of the murine B-Ly1 antibody. The term "cytotoxic moiety" as used herein is intended to include such isotopes.

In another embodiment, liposomes are filled with a cytotoxic drug and the liposomes are coated with the ABMs of the present invention. Because there are many CD20 molecules on the surface of the malignant B-cell, this method permits delivery of large amounts of drug to the correct cell type.

Techniques for conjugating such therapeutic agents to antibodies are well known (see, e.g., Arnon et al., "Monoclonal Antibodies for Immunotargeting of Drugs in Cancer Therapy", in *Monoclonal Antibodies and Cancer Therapy*, Reisfeld et al. (eds.), pp. 243-56 (Alan R. Liss, Inc. 1985); Hellstrom et al., "Antibodies For Drug Delivery", in *Controlled Drug Delivery* (2nd Ed.), Robinson et al. (eds.), pp. 623-53 (Marcel Dekker, Inc. 1987); Thorpe, "Antibody Carriers Of Cytotoxic Agents In Cancer Therapy: A Review", in *Monoclonal Antibodies '84: Biological And Clinical Applications*, Pinchera et al. (eds.), pp. 475-506 (1985); and Thorpe et al., "The Preparation And Cytotoxic Properties Of Antibody-Toxin Conjugates", *Immunol. Rev.*, 62:119-58 (1982)).

Still other therapeutic applications for the ABMs of the invention include conjugation or linkage, e.g., by recombinant DNA techniques, to an enzyme capable of converting a prodrug into a cytotoxic drug and the use of that antibody-enzyme conjugate in combination with the prodrug to convert the prodrug to a cytotoxic agent at the tumor site (see, e.g., Senter et al., "Anti-Tumor Effects of Antibody-alkaline Phosphatase", *Proc. Natl. Acad. Sci. USA* 85:4842-46 (1988); "Enhancement of the in vitro and in vivo Antitumor Activities of Phosphorylated Mitocycin C and Etoposide Derivatives by Monoclonal Antibody-Alkaline Phosphatase Conjugates", Cancer Research 49:5789-5792 (1989); and Senter, "Activation of Prodrugs by Antibody-Enzyme Conjugates: A New Approach to Cancer Therapy," *FASEB J.* 4:188-193 (1990)).

Still another therapeutic use for the ABMs of the invention involves use, either unconjugated, in the presence of complement, or as part of an antibody-drug or antibody-toxin conjugate, to remove tumor cells from the bone marrow of cancer patients. According to this approach, autologous bone marrow may be purged ex vivo by treatment with the antibody and the marrow infused back into the patient [see, e.g., Ramsay et al., "Bone Marrow Purging Using Monoclonal Antibodies", *J. Clin. Immunol.*, 8(2):81-88 (1988)].

Furthermore, it is contemplated that the invention comprises a single-chain immunotoxin comprising antigen binding domains that allow substantially the same specificity of binding as the murine B-Ly1 antibody (e.g., polypeptides comprising the CDRs of the murine B-Ly1 antibody) and further comprising a toxin polypeptide. The single-chain immunotoxins of the invention may be used to treat human carcinoma in vivo.

Similarly, a fusion protein comprising at least the antigen-binding region of an ABM of the invention joined to at least a functionally active portion of a second protein having antitumor activity, e.g., a lymphokine or oncostatin, can be used to treat human carcinoma in vivo.

The present invention provides a method for selectively killing tumor cells expressing CD20. This method comprises reacting the immunoconjugate (e.g., the immunotoxin) of the invention with said tumor cells. These tumor cells may be from a human carcinoma.

Additionally, this invention provides a method of treating carcinomas (for example, human carcinomas) in vivo. This method comprises administering to a subject a pharmaceutically effective amount of a composition containing at least one of the immunoconjugates (e.g., the immunotoxin) of the invention.

In a further aspect, the invention is directed to an improved method for treating B-cell proliferative disorders including B-cell lymphoma, as well as an autoimmune disease produced in whole or in part by pathogenic autoantibodies, based on B-cell depletion comprising administering a therapeutically effective amount of an ABM of the present invention to a human subject in need thereof. In a preferred embodiment, the ABM is a glycoengineered anti-CD20 antibody with a binding specificity substantially the same as that of the murine B-Ly1 antibody. In another preferred embodiment the antibody is humanized. Examples of autoimmune diseases or disorders include, but are not limited to, immune-mediated thrombocytopenias, such as acute idiopathic thrombocytopenic purpurea and chronic idiopathic thrombocytopenic purpurea, dermatomyositis, Sydenham's chorea, lupus nephritis, rheumatic fever, polyglandular syndromes, Henoch-Schonlein purpura, post-streptococcal nephritis, erythema nodosum, Takayasu's arteritis, Addison's disease, erythema multiforme, polyarteritis nodosa, ankylosing spondylitis, Goodpasture's syndrome, thromboangitis ubiterans, primary biliary cirrhosis, Hashimoto's thyroiditis, thyrotoxicosis, chronic active hepatitis, polymyositis/dermatomyositis, polychondritis, pamphigus vulgaris, Wegener's granulomatosis, membranous nephropathy, amyotrophic lateral sclerosis, tabes dorsalis, polymyaglia, pernicious anemia, rapidly progressive glomerulonephritis and fibrosing alveolitis, inflammatory responses such as inflammatory skin diseases including psoriasis and dermatitis (e.g. atopic dermatitis); systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g. Type 1 diabetes mellitus or insulin dependent diabetes mellitus); multiple sclerosis; Reynaud's syndrome; autoimmune thyroiditis; allergic encephalomyelitis; Sjorgen's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious amenia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Behcet disease; giant cell arteritis; immune complex nephritis; IgA nephropathy; IgM polyneuropathies; immune thrombocytopenic purpura (ITP) or autoimmune thrombocytopenia etc. In this aspect of the invention, the ABMs of the invention are used to deplete the blood of normal B-cells for an extended period.

In accordance with the practice of this invention, the subject may be a human, equine, porcine, bovine, murine, canine, feline, and avian subjects. Other warm blooded animals are also included in this invention.

The subject invention further provides methods for inhibiting the growth of human tumor cells, treating a tumor in a subject, and treating a proliferative type disease in a subject. These methods comprise administering to the subject an effective amount of the composition of the invention.

It is apparent, therefore, that the present invention encompasses pharmaceutical compositions, combinations and methods for treating human carcinomas, such as a B cell lymphoma. For example, the invention includes pharmaceutical compositions for use in the treatment of human carcinomas comprising a pharmaceutically effective amount of an antibody of the present invention and a pharmaceutically acceptable carrier.

The ABM compositions of the invention can be administered using conventional modes of administration including, but not limited to, intravenous, intraperitoneal, oral, intralymphatic or administration directly into the tumor. Intravenous administration is preferred.

In one aspect of the invention, therapeutic formulations containing the ABMs of the invention are prepared for storage by mixing an antibody having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Exemplary anti-CD20 ABM formulations are described in WO98/56418, expressly incorporated herein by reference. This publication describes a liquid multidose formulation comprising 40 mg/mL rituximab, 25 mM acetate, 150 mM trehalose, 0.9% benzyl alcohol, 0.02% polysorbate 20 at pH 5.0 that has a minimum shelf life of two years storage at 2-8° C. Another anti-CD20 formulation of interest comprises 10 mg/mL rituximab in 9.0 mg/mL sodium chloride, 7.35 mg/mL sodium citrate dihydrate, 0.7 mg/mL polysorbate 80, and Sterile Water for Injection, pH6.5. In the present invention, RITUXAN® will be substituted by an ABM of the present invention.

Lyophilized formulations adapted for subcutaneous administration are described in WO97/04801. Such lyophihized formulations may be reconstituted with a suitable diluent to a high protein concentration and the reconstituted formulation may be administered subcutaneously to the mammal to be treated herein.

The formulation herein may also contain more than one active compound as necessary for the particular indication being treated, preferably those with complementary activities that do not adversely affect each other. For example, it may be desirable to further provide a cytotoxic agent, chemotherapeutic agent, cytokine or immunosuppressive agent (e.g. one which acts on T cells, such as cyclosporin or an antibody that binds T cells, e.g., one which binds LFA-1). The effective amount of such other agents depends on the amount of antagonist present in the formulation, the type of disease or disorder or treatment, and other factors discussed above. These are generally used in the same dosages and with administration routes as used hereinbefore or about from 1 to 99% of the heretofore employed dosages.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antagonist, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

The compositions of the invention may be in a variety of dosage forms which include, but are not limited to, liquid solutions or suspension, tablets, pills, powders, suppositories, polymeric microcapsules or microvesicles, liposomes, and injectable or infusible solutions. The preferred form depends upon the mode of administration and the therapeutic application.

The compositions of the invention also preferably include conventional pharmaceutically acceptable carriers and adjuvants known in the art such as human serum albumin, ion exchangers, alumina, lecithin, buffer substances such as phosphates, glycine, sorbic acid, potassium sorbate, and salts or electrolytes such as protamine sulfate.

The most effective mode of administration and dosage regimen for the pharmaceutical compositions of this invention depends upon the severity and course of the disease, the patient's health and response to treatment and the judgment of the treating physician. Accordingly, the dosages of the compositions should be titrated to the individual patient. Nevertheless, an effective dose of the compositions of this invention will generally be in the range of from about 0.01 to about 2000 mg/kg.

The molecules described herein may be in a variety of dosage forms which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application.

The composition comprising an ABM of the present invention will be formulated, dosed, and administered in a fashion consistent with good medical practice. Factors for consideration in this context include the particular disease or disorder being treated, the particular mammal being treated, the clinic condition of the individual patient, the cause of the disease or disorder, the site of delivery of the agent, the method of administration, the scheduling of administration, and other factors known to medical practitioners. The therapeutically effective amount of the antagonist to be administered will be governed by such considerations.

As a general proposition, the therapeutically effective amount of the antibody administered parenterally per dose will be in the range of about 0.1 to 20 mg/kg of patient body weight per day, with the typical initial range of antagonist used being in the range of about 2 to 10 mg/kg.

In a preferred embodiment, the ABM is an antibody, preferably a humanized antibody Suitable dosages for such an unconjugated antibody are, for example, in the range from about 20 mg/m$^2$ to about 1000 mg/m$^2$. In one embodiment, the dosage of the antibody differs from that presently recommended for RITUXAN®. For example, one may administer to the patient one or more doses of substantially less than 375 mg/m$^2$ of the antibody, e.g., where the dose is in the range from about 20 mg/m$^2$ to about 250 mg/m$^2$, for example from about 0.50 mg/m$^2$ to about 200 mg/m$^2$.

Moreover, one may administer one or more initial dose(s) of the antibody followed by one or more subsequent dose(s), wherein the mg/m$^2$ dose of the antibody in the subsequent dose(s) exceeds the mg/m$^2$ dose of the antibody in the initial dose(s). For example, the initial dose may be in the range from about 20 mg/m$^2$ to about 250 mg/m$^2$ (e.g., from about 50 mg/m$^2$ to about 200 mg/m$^2$) and the subsequent dose may be in the range from about 250 mg/m$^2$ to about 1000 mg/m$^2$.

As noted above, however, these suggested amounts of ABM are subject to a great deal of therapeutic discretion. The key factor in selecting an appropriate dose and scheduling is the result obtained, as indicated above. For example, relatively higher doses may be needed initially for the treatment of ongoing and acute diseases. To obtain the most efficacious results, depending on the disease or disorder, the antagonist is administered as close to the first sign, diagnosis, appearance, or occurrence of the disease or disorder as possible or during remissions of the disease or disorder.

The ABM of the present invention is administered by any suitable means, including parenteral, subcutaneous, intraperitoneal, intrapulinonary, and intranasal, and, if desired for local immunosuppressive treatment, intralesional administration. Parenteral infusions include intramuscular, intravenous, intraarterial, intraperitoneal, or subcutaneous administration. In addition, the antagonist may suitably be administered by pulse infusion, e.g., with declining doses of the antagonist. Preferably the dosing is given by injections, most preferably intravenous or subcutaneous injections, depending in part on whether the administration is brief or chronic.

One may administer other compounds, such as cytotoxic agents, chemotherapeutic agents, immunosuppressive agents and/or cytokines with the antagonists herein. The combined administration includes coadministration, using separate formulations or a single pharmaceutical formulation, and consecutive administration in either order, wherein preferably there is a time period while both (or all) active agents simultaneously exert their biological activities.

It would be clear that the dose of the composition of the invention required to achieve cures may be further reduced with schedule optimization.

In accordance with the practice of the invention, the pharmaceutical carrier may be a lipid carrier. The lipid carrier may be a phospholipid. Further, the lipid carrier may be a fatty acid. Also, the lipid carrier may be a detergent. As used herein, a detergent is any substance that alters the surface tension of a liquid, generally lowering it.

In one example of the invention, the detergent may be a nonionic detergent. Examples of nonionic detergents include, but are not limited to, polysorbate 80 (also known as Tween 80 or (polyoxyethylenesorbitan monooleate), Brij, and Triton (for example Triton WR-1339 and Triton A-20).

Alternatively, the detergent may be an ionic detergent. An example of an ionic detergent includes, but is not limited to, alkyltrimethylammonium bromide.

Additionally, in accordance with the invention, the lipid carrier may be a liposome. As used in this application, a "liposome" is any membrane bound vesicle which contains any molecules of the invention or combinations thereof.

The examples below explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

EXAMPLES

[NOTE: Unless otherwise specified, references to the numbering of specific amino acid residue positions in the following examples are according to the Kabat numbering system.]

Example 1

Materials and Methods

Cloning and Expression of Recombinant Antibody B-Ly1

B-Ly1 expressing hybridoma cells were grown in RPMI containing 10% FBS and 4 mM L-glutamine. 6×10$^6$ cells with a viability >90% were harvested and total RNA was isolated using a Qiagen RNAeasy midi kit. cDNAs encoding the variable light and heavy chains of B-Ly1 were amplified by RT-PCR. The RT-PCR reaction was performed using the following conditions: 30 min 50° C. for the first strand cDNA synthesis; 15 min 95° C. initial denaturation; 30 cycles of 1 min 94° C., 1 min 45° C., 1.5 min 72° C.; and a final elongation step for 10 min at 72° C. The expected size of the PCR products was confirmed by gel electrophoresis. The PCR products were cloned into suitable *E. coli* vectors and DNA sequencing confirmed that the variable light and heavy chain encoding genes were isolated.

For construction of chimeric B-Ly1 expression vectors, synthetic signal sequences and appropriate restriction sites were fused to the variable chains by additional PCR reactions. After a final confirmation of the correct DNA sequence of the variable chains, they were combined with the corresponding human IgG1 constant regions. Once the genes were constructed, they were cloned under control of the MPSV promoter and upstream of a synthetic polyA site, using two separate vectors, one for each chain, resulting in the plasmids pETR1808 (heavy chain expression vector) and pETR1813 (light chain expression vector). Each vector carried an EBV OriP sequence.

Chimeric B-Ly1 was produced by co-transfecting HEK293-EBNA cells with vectors pETR1808 and pETR1813 using a calcium phosphate-transfection approach. Exponentially growing HEK293-EBNA cells were transfected by the calcium phosphate method. Cells were grown as adherent monolayer cultures in T flasks using DMEM culture medium supplemented with 10% FCS, and were transfected when they were between 50 and 80% confluent. For the transfection of a T75 flask, 8 million cells were seeded 24 hours before transfection in 14 ml DMEM culture medium supplemented with FCS (at 10% V/V final), 250 μg/ml neomycin, and cells were placed at 37° C. in an incubator with a 5% $CO_2$ atmosphere overnight. For each T75 flask to be transfected, a solution of DNA, $CaCl_2$ and water was prepared by mixing 47 μg total plasmid vector DNA divided equally between the light and heavy chain expression vectors, 235 μl of a 1M $CaCl_2$ solution, and adding water to a final volume of 469 μl. To this solution, 469 μl of a 50 mM HEPES, 280 mM NaCl, 1.5 mM $Na_2HPO_4$ solution at pH 7.05 were added, mixed immediately for 10 sec and left to stand at room temperature for 20 sec. The suspension was diluted with 12 ml of DMEM supplemented with 2% FCS, and added to the T75 in place of the existing medium. The cells were incubated at 37° C., 5% $CO_2$ for about 17 to 20 hours, then medium was replaced with 12 ml DMEM, 0% FCS. For the production of unmodified antibody "chB-Ly1", the cells were transfected only with antibody expression vectors pETR1808 and pETR1813 in a 1:1 ratio. For the production of the glycoengineered antibody "chB-Ly1-ge", the cells were co-transfected with four plasmids, two for antibody expression (pETR1808 and pETR1813), one for a fusion GnTIII polypeptide expression (pETR1519), and one for mannosidase II expression (pCLF9) at a ratio of 4:4:1:1, respectively. At day 5 post-transfection, supernatant was harvested, centrifuged for 5 min at 1200 rpm, followed by a second centrifugation for 10 min at 4000 rpm and kept at 4° C.

chB-Ly1 and chB-Ly1-ge were purified from culture supernatant using three sequential chromatographic steps, Protein A chromatography, cation exchange chromatography, and a size exclusion chromatography step on a Superdex 200 column (Amersham Pharmacia) exchanging the buffer to phosphate buffer saline and collecting the monomeric antibody peak from this last step. Antibody concentration was estimated using a spectrophotometer from the absorbance at 280 nm.

Oligosaccharide Analysis

Oligosaccharides were enzymatically released from the antibodies by PNGaseF digestion, with the antibodies being either immobilized on a PVDF membrane or in solution.

The resulting digest solution containing the released oligosaccharides either prepared directly for MALDI/TOF-MS analysis or was further digested with EndoH glycosidase prior to sample preparation for MALDI/TOF-MS analysis.

Oligosaccharide Release Method for PVDF Membrane-Immobilized Antibodies

The wells of a 96-well plate made with a PVDF (Immobilon P, Millipore, Bedford, Mass.) membrane were wetted with 100 μl methanol and the liquid was drawn through the PVDF membrane using vacuum applied to the Multiscreen vacuum manifold (Millipore, Bedford, Mass.). The PVDF membranes were washed three times with 300 μl of water. The wells were then washed with 50 μl RCM buffer (8M Urea, 360 mM Tris, 3.2 mM EDTA, pH 8.6). Between 3040 μg antibody was loaded in a well containing 10 μl RCM buffer. The liquid in the well was drawn through the membrane by applying vacuum, and the membrane was subsequently washed twice with 50 μl RCM buffer. The reduction of disulfide bridges was performed by addition of 50 μl of 0.1M dithiothreitol in RCM and incubation at 37° C. for 1 h.

Following reduction, a vacuum was applied to remove the dithiothreitol solution from the well. The wells were washed three times with 300 μl water before performing the carboxymethylation of the cysteine residues by addition of 50 μl of 0.1 M iodoacetic acid in RCM buffer and incubation at room temperature in the dark for 30 min.

After carboxymethylation, the wells were drawn with vacuum and subsequently washed three times with 300 μl water. The PVDF membrane was then blocked, to prevent adsorption of the endoglycosidase, by incubating 100 μl of a 1% aqueous solution of polyvinylpyrrolidone 360 at room temperature for 1 hour. The blocking reagent was then removed by gentle vacuum followed by three washes with 300 μl water.

N-linked oligosaccharides were released by addition of 2.5 mU peptide-N-glycosydase F (recombinat N-Glycanase, GLYKO, Novato, Calif.) and 0.1 mU Sialidase (GLYKO, Novato, Calif.), to remove any potential charged monosaccharide residues, in a final volume of 25 μl in 20 mM $NaHCO_3$, pH7.0). Digestion was performed for 3 hours at 37° C.

Oligosaccharide Release Method for Antibodies in Solution

Between 40 and 50 μg of antibody were mixed with 2.5 mU of PNGaseF (Glyko, U.S.A.) in 2 mM Tris, pH7.0 in a final volume of 25 microliters, and the mix was incubated for 3 hours at 37° C.

Use of Endoglycosidase H Digestion of PNGaseF-Released Oligosaccharides for the Assignment of Hybrid Bisected Oligosaccharide Structures to MALDI/TOF-MS Neutral Oligosaccharide Peaks The PNGaseF released oligosaccharides were subsequently digested with Endoglycosidase H (EC 3.2.1.96). For the EndoH digestion, 15 mU of EndoH (Roche, Switzerland) were added to the PNGaseF digest (antibody in solution method above) to give a final volume of 30 microliters, and the mix was incubated for 3 hours at 37° C. EndoH cleaves between the N-acetylglucosamine residues of the chitobiose core of N-linked oligosaccharides. The enzyme can only digest oligomannose and most hybrid type glycans, whereas complex type oligosaccharides are not hydrolyzed.

Sample Preparation for MALDI/TOF-MS

The enzymatic digests containing the released oligosaccharides were incubated for a further 3 h at room after the addition of acetic acid to a final concentration of 150 mM, and were subsequently passed through 0.6 ml of cation exchange resin (AG50W-X8 resin, hydrogen form, 100-200 mesh, Bio-Rad, Switzerland) packed into a micro-bio-spin chromatography column (BioRad, Switzerland) to remove cations and proteins. One microliter of the resulting sample was applied to a stainless steel target plate, and mixed on the plate with 1 μl of sDHB matrix. sDHB matrix was prepared by dissolving 2 mg of 2,5-dihydroxybenzoic acid plus 0.1 mg of 5-methoxysalicylic acid in 1 ml of ethanol/10 mM aqueous sodium chloride 1:1 (v/v). The samples were air dried, 0.2 μl ethanol was applied, and the samples were finally allowed to re-crystallize under air.

MALDI/TOF-MS

The MALDI-TOF mass spectrometer used to acquire the mass spectra was a Voyager Elite (Perspective Biosystems). The instrument was operated in the linear configuration, with an acceleration of 20 kV and 80 ns delay. External calibration using oligosaccharide standards was used for mass assignment of the ions. The spectra from 200 laser shots were summed to obtain the final spectrum.

Whole Blood B Cell Depletion 495 ul heparinized blood from a healthy donor was aliquoted into 5 ml polystyrene tubes, 5 μl 100-fold concentrated antibody samples (1-1000 ng/ml final concentration) or PBS only were added and the tubes were incubated at 370. After 24 h 50 μl blood was transferred to a fresh tube and stained with anti-CD3-FITC, anti-CD19-PE and anti-CD45-

CyChrome (Becton-Dickinson) for 15 min at room temperature in the dark. Before analysis, 500 µl FACS buffer (PBS containing 2% FCS and 5 mM EDTA) was added to the tubes. The CD3-FITC and CD19-PE fluorescence of the blood samples were flowcytometrically analyzed by setting a threshold on CD45-CyChrome. B cell-depletion was determined by plotting the ratio of CD19⁺ B cells to CD3⁺ T cells.

Binding of Anti-CD20 Antibodies to Raji Cells 500,000 in 180 µl FACS buffer (PBS containing 2% FCS and 5 mM EDTA) were transferred to 5 ml polystyrene tubes and 20 ul 10 fold concentrated anti-CD20 antibody samples (1-5000 ng/ml final concentration) or PBS only were added and the tubes were incubated at 4° C. for 30 min. Subsequently, samples were washed twice with FACS buffer and pelleted at 300×g for 3 min. Supernatant was aspirated off and cells were taken up in 100 µl FACS buffer and 1 µl anti-Fc-specific F(ab')2-FITC fragments (Jackson Immuno Research Laboratories, USA) was added and the tubes were incubated at 4° C. for 30 min. Samples were washed twice with FACS buffer and taken up in 500 µl of FACS buffer containing 0.5 µg/ml PI for analysis by Flow Cytometry. Binding was determined by plotting the geometric mean fluorescence against the antibody concentrations.

Example 2

High Homology Acceptor Approach

The high homology antibody acceptor framework search was performed by aligning the mouse B-ly1 protein sequence to a collection of human germ-line sequences and picking that human sequence that showed the highest sequence identity. Here, the sequence VH1_10 from the VBase database was chosen as the heavy chain framework acceptor sequence, and the VK_2_40 sequence was chosen to be the framework acceptor for the light chain. Onto these two acceptor frameworks, the three complementary determining regions (CDRs) of the mouse heavy and light variable domains were grafted. Since the framework 4 region is not part of the variable region of the germ line V gene, the alignment for that position was done individually. The JH4 region was chosen for the heavy chain, and the JK4 region was chosen for the light chain. Molecular modelling of the designed immunoglobulin domain revealed one spot potentially requiring the murine amino acid residues instead of the human ones outside of the CDR. Re-introducing murine amino acid residues into the human framework would generate the so-called back mutations. For example, the human acceptor amino acid residue at Kabat position 27 was back mutated to a tyrosine residue. Humanized antibody variants were designed that either included or omitted the back mutations. The humanized antibody light chain did not require any back mutations. After having designed the protein sequences, DNA sequences encoding these proteins were synthesized as detailed below.

Mixed Framework Approach

In order to avoid introducing back mutations at critical amino acid residue positions (critical to retain good antigen binding affinity or antibody functions) of the human acceptor framework, it was investigated whether either the whole framework region 1 (FR1), or framework regions 1 (FR1) and 2 (FR2) together, could be replaced by human antibody sequences already having donor residues, or functionally equivalent ones, at those important positions in the natural human germline sequence. For this purpose, the $V_H$ frameworks 1 and 2 of the mouse Bly1 sequence were aligned individually to human germ-line sequences. Here, highest sequence identity was not important, and was not used, for choosing acceptor frameworks, but instead matching of several critical residues was assumed to be more important. Those critical residues comprise residues 24, 71, and 94 (Kabat numbering), and also those residues at position 27, 28, and 30 (Kabat numbering), which lie outside of the CDR1 definition by Kabat, but often are involved in antigen binding. The IMGT sequence VH_3_15 was chosen as a suitable one. After having designed the protein sequences, DNA sequences encoding these proteins were synthesized as detailed below. Using this approach no back mutations were required either for the light or heavy chain, in order to retain good levels of antigen binding.

Synthesis of the Antibody Genes

After having designed the amino acid sequence of the humanized antibody V region, the DNA sequence had to be generated. The DNA sequence data of the individual framework regions was found in the databases for human germ line sequences. The DNA sequence of the CDR regions was taken from the corresponding murine cDNA data. With these sequences, the whole DNA sequence was virtually assembled. Having this DNA sequence data, diagnostic restriction sites were introduced in the virtual sequence, by introducing silent mutations, creating recognition sites for restriction endonucleases. To obtain the physical DNA chain, gene synthesis was performed (e.g., Wheeler et al. 1995). In this method, oligonucleotides are designed from the genes of interest, such, that a series of oligonucleotides is derived from the coding strand, and one other series is from the non-coding strand. The 3' and 5' ends of each oligonucleotide (except the very first and last in the row) always show complementary sequences to two primers derived from the opposite strand. When putting these oligonucleotides into a reaction buffer suitable for any heat stable polymerase, and adding $Mg^{2+}$, dNTPs and a DNA polymerase, each oligonucleotide is extended from its 3' end. The newly formed 3' end of one primer then anneals with the next primer of the opposite strand, and extending its sequence further under conditions suitable for template dependant DNA chain elongation. The final product was cloned into a conventional vector for propagation in E. coli.

Antibody Production

Human heavy and light chain leader sequences (for secretion) were added upstream of the above variable region sequences and these were then joined upstream of human IgG1 kappa constant heavy and light chain sequences, respectively, using standard molecular biology techniques. The resulting full antibody heavy and light chain DNA sequences were subcloned into mammalian expression vectors (one for the light chain and one for the heavy chain) under the control of the MPSV promoter and upstream of a synthetic polyA site, each vector carrying an EBV OriP sequence, as described in Example 1 above. Antibodies were produced as described in Example 1 above, namely by co-transfecting HEK293-EBNA with the mammalian antibody heavy and light chain expression vectors, harvesting the conditioned culture medium 5 to 7 days post-transfection, and purifying the secreted antibodies by Protein A affinity chromatography, followed by cation exchange chromatography and a final size exclusion chromatographic step to isolate pure monomeric IgG1 antibodies. The antibodies were formulated in a 25 mM potassium phosphate, 125 mM sodium chloride, 100 mM glycine solution of pH 6.7. Glycoengineered variants of the humanized antibody variants were produced by co-transfection of the antibody expression vectors together with a GnT-III glycosyltransferase expression vectors, or together with a GnT-III expression vector plus a Golgi mannosidase II expression vector, as described for the chimeric antibody in Example 1 above. Glycoengineered antibodies were purified and formulated as described above for the non-glycoengineered antibodies. The oligosaccharides attached to the Fc region of the antibodies was analysed by MALDI/TOF-MS as described below.

Oligossacharide Analysis

Oligosaccharide Release Method for Antibodies in Solution

Between 40 and 50 µg of antibody were mixed with 2.5 mU of PNGaseF (Glyko, U.S.A.) in 2 mM Tris, pH7.0 in a final volume of 25 microliters, and the mix was incubated for 3 hours at 37° C.

Sample Preparation for MALDI/TOF-MS

The enzymatic digests containing the released oligosaccharides were incubated for a further 3 h at room temperature after the addition of acetic acid to a final concentration of 150 mM, and were subsequently passed through 0.6 ml of cation exchange resin (AG50W-X8 resin, hydrogen form, 100-200 mesh, BioRad, Switzerland) packed into a micro-bio-spin chromatography column (BioRad, Switzerland) to remove cations and proteins. One microliter of the resulting sample was applied to a stainless steel target plate, and mixed on the plate with 1 µl of sDHB matrix. sDHB matrix was prepared by dissolving 2 mg of 2,5-dihydroxybenzoic acid plus 0.1 mg of 5-methoxysalicylic acid in 1 ml of ethanol/10 mM aqueous sodium chloride 1:1 (v/v). The samples were air dried, 0.2 µl ethanol was applied, and the samples were finally allowed to re-crystallize under air.

MALDI/TOF-MS

The MALDI-TOF mass spectrometer used to acquire the mass spectra was a Voyager Elite (Perspective Biosystems). The instrument was operated in the linear configuration, with an acceleration of 20 kV and 80 ns delay. External calibration using oligosaccharide standards was used for mass assignment of the ions. The spectra from 200 laser shots were summed to obtain the final spectrum.

Antigen Binding Assay

The purified, monomeric humanized antibody variants were tested for binding to human CD20 on Raji B-cell lymphoma target cells using a flow cytometry-based assay, as described for the chimeric B-ly1 antibody in Example 1 above.

Binding of Monomeric IgG1 Glycovariants to NK Cells and Fc☐RIIIA-Expressing CHO Cell Line Human NK cells were isolated from freshly isolated peripheral blood mononuclear cells (PBMC) applying a negative selection enriching for CD16- and CD56-positive cells (MACS system, Miltenyi Biotec GmbH, Bergisch Gladbach/Germany). The purity determined by CD56 expression was between 88-95%. Freshly isolated NK cells were incubated in PBS without calcium and magnesium ions ($3 \times 10^5$ cells/ml) for 20 minutes at 37° C. to remove NK cell-associated IgG. Cells were incubated at $10^6$ cells/ml at different concentrations of anti-CD20 antibody (0, 0.1, 0.3, 1, 3, 10 µg/ml) in PBS, 0.1% BSA. After several washes antibody binding was detected by incubating with 1:200 FITC-conjugated F(ab')$_2$ goat anti-human, F(ab')2 specific IgG (Jackson Immuno Research, West Grove, Pa./USA) and anti-human CD56-PE (BD Biosciences, Allschwil/Switzerland). The anti-FcgammaRIIIA 3G8 F(ab')2 fragments (Ancell, Bayport, Minn./USA) were added at a concentration of 10 µg/ml to compete binding of antibody glycovariants (3 µg/ml). The fluorescence intensity referring to the bound antibody variants was determined for CD56-positive cells on a FACSCalibur (BD Biosciences, Allschwil/Switzerland). CHO cells were transfected by electroporation (280 V, 950 µF, 0.4 cm) with an expression vector coding for the FcgammaRIIIA-Val158 α-chain and the γ-chain. Transfectants were selected by addition of 6 µg/ml puromycin and stable clones were analyzed by FACS using 10 µl FITC-conjugated-anti-FcgammaRIII 3G8 monoclonal antibody (BD Biosciences, Allschwil/Switzerland) for $10^6$ cells. Binding of IgG1 to FcgammaRIIIA-Val 158-expressing CHO cells was performed analogously to the NK cell binding described above.

ADCC Assay

Human peripheral blood mononuclear cells (PBMC) were used as effector cells and were prepared using Histopaque-1077 (Sigma Diagnostics Inc., St. Louis, Mo. 63178 USA) and following essentially the manufacturer's instructions. In brief, venous blood was taken with heparinized syringes from volunteers. The blood was diluted 1:0.75-1.3 with PBS (not containing Ca++ or Mg++) and layered on Histopaque-1077. The gradient was centrifuged at 400×g for 30 min at room temperature (RT) without breaks. The interphase containing the PBMC was collected and washed with PBS (50 ml per cells from two gradients) and harvested by centrifugation at 300×g for 10 minutes at RT. After resuspension of the pellet with PBS, the PBMC were counted and washed a second time by centrifugation at 200×g for 10 minutes at RT. The cells were then resuspended in the appropriate medium for the subsequent procedures.

The effector to target ratio used for the ADCC assays was 25:1 and 10:1 for PBMC and NK cells, respectively. The effector cells were prepared in AIM-V medium at the appropriate concentration in order to add 50 µl per well of round bottom 96 well plates. Target cells were human B lymphoma cells (e.g., Raji cells) grown in DMEM containing 10% FCS. Target cells were washed in PBS, counted and resuspended in AIM-V at 0.3 million per ml in order to add 30,000 cells in 100 µl per microwell. Antibodies were diluted in AIM-V, added in 50 µl to the pre-plated target cells and allowed to bind to the targets for 10 minutes at RT. Then the effector cells were added and the plate was incubated for 4 hours at 37° C. in a humified atmosphere containing 5% $CO_2$. Killing of target cells was assessed by measurement of lactate dehydrogenase (LDH) release from damaged cells using the Cytotoxicity Detection kit (Roche Diagnostics, Rotkreuz, Switzerland). After the 4-hour incubation the plates were centrifuged at 800×g. 100 µl supernatant from each well was transferred to a new transparent flat bottom 96 well plate. 100 µl color substrate buffer from the kit were added per well. The Vmax values of the color reaction were determined in an ELISA reader at 490 nm for at least 10 min using SOFTmax PRO software (Molecular Devices, Sunnyvale, Calif. 94089, USA). Spontaneous LDH release was measured from wells containing only target and effector cells but no antibodies. Maximal release was determined from wells containing only target cells and 1% Triton X-100. Percentage of specific antibody-mediated killing was calculated as follows: ((x−SR)/(MR−SR)*100, where x is the mean of Vmax at a specific antibody concentration, SR is the mean of Vmax of the spontaneous release and MR is the mean of Vmax of the maximal release.

Complement Dependent Cytotoxicity Assay

Target cells were counted, washed with PBS, resuspended in AIM-V (Invitrogen) at 1 million cells per ml. 50 µl cells were plated per well in a flat bottom 96 well plate. Antibody dilutions were prepared in AIM-V and added in 50 µl to the cells. Antibodies were allowed to bind to the cells for 10 minutes at room temperature. Human serum complement (Quidel) was freshly thawed, diluted 3-fold with AIM-V and added in 50 µl to the wells. Rabbit complement (Cedarlane Laboratories) was prepared as described by the manufacturer, diluted 3-fold with AIM-V and added in 50 µl to the wells. As a control, complement sources were heated for 30 min at 56° C. before addition to the assay.

The assay plates were incubated for 2 h at 37° C. Killing of cells was determined by measuring LDH release. Briefly, the plates were centrifuged at 300×g for 3 min. 50 µl supernatant per well were transferred to a new 96 well plate and 50 µl of the assay reagent from the Cytotoxicity Kit (Roche) were added. A kinetic measurement with the ELISA reader determined the Vmax corresponding with LDH concentration in the supernatant. Maximal release was determined by incubating the cells in presence of 1% Trition X-100.

Whole Blood B-Cell Depletion Assay

Normal B-cell depletion in whole blood by the anti-CD20 antibodies was carried out as described in Example 1 above.

Apoptosis Assay

The apoptotic potency of the antibodies was assayed by incubating the antibody at 10 µg/ml (saturating conditions in respect to antigen binding) with the target cells (at a target cell concentration of $5 \times 10^5$ cells/ml) overnight (16-24 h). Samples were stained with AnnV-FITC and analyzed by FACS. Assay was done in triplicates.

Detection is performed by flow cytometry by following the appearance of apoptotic markers like annexin V and phosphatidy serine. Negative control (no apoptosis induced) does not contain any antibody, but only phosphate buffered saline. Positive control (maximal apoptosis) contains 5 micromolar of the strong apoptosis inducer Camptothecin (CPT).

Results and Discussion

Figure 11:
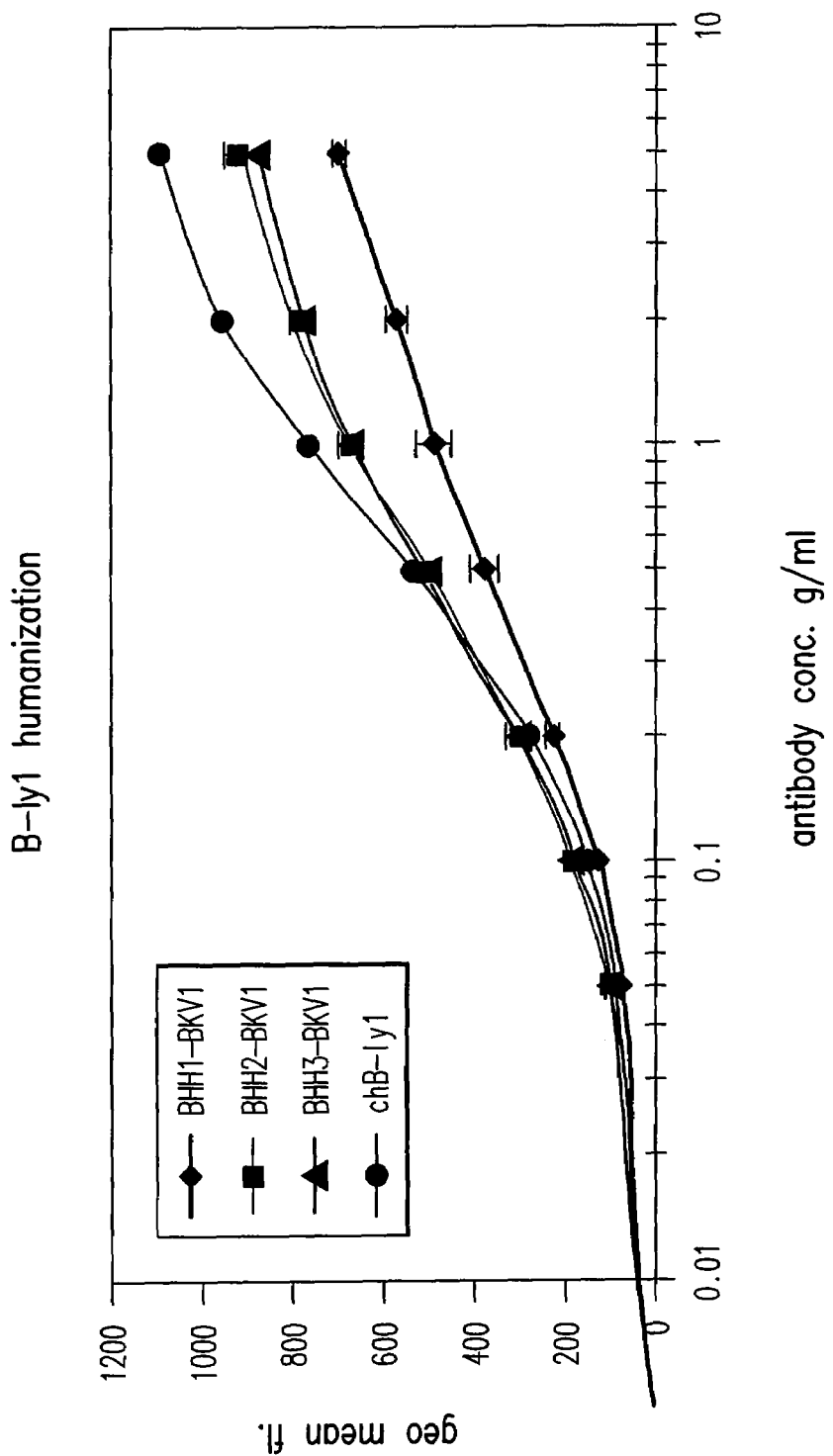
FIG. 11. Comparison of the binding behavior between B-HH1, B-HH2, B-HH3, and the parental antibody B-ly1. The data show that all Abs show a similar EC50 value, but the B-HH1 construct binds with a lower intensity/stoichiometry than the variants B-HH2 and B-HH3. B-HH1 can be distinguished from B-HH2 and B-HH3 by its partially human CDR1 and CDR2 regions (Kabat definition), as well as the Ala/Thr polymorphism at position 28 (Kabat numbering). This indicates that either position 28, the complete CDR1, and/or the complete CDR2 is important for antibody/antigen interaction.

Comparison of the binding to human CD20 antigen of antibody variants B-HH1, B-HH2, B-HH3, either complexed with the chimeric B-ly1 light chain (mVL, as described in Example 1 above) or with the humanized B-ly1 light chain (KV1), and the parental, chimeric antibody chB-ly1 (described in Example 1 above) shows that all antibodies have a similar EC50 value, but the B-HH1 construct binds with a lower intensity/stoichiometry than the variants B-HH2 and B-HH3 (FIG. 11). B-HH1 can be distinguished from B-HH2 and B-HH3 by its partially human CDR1 and CDR2 regions (Kabat definition), as well as the Ala/Thr polymorphism at position 28 (Kabat numbering). This indicates that either position 28, the complete CDR1, and/or the complete CDR2 are important for antibody/antigen interaction.

Figure 12:
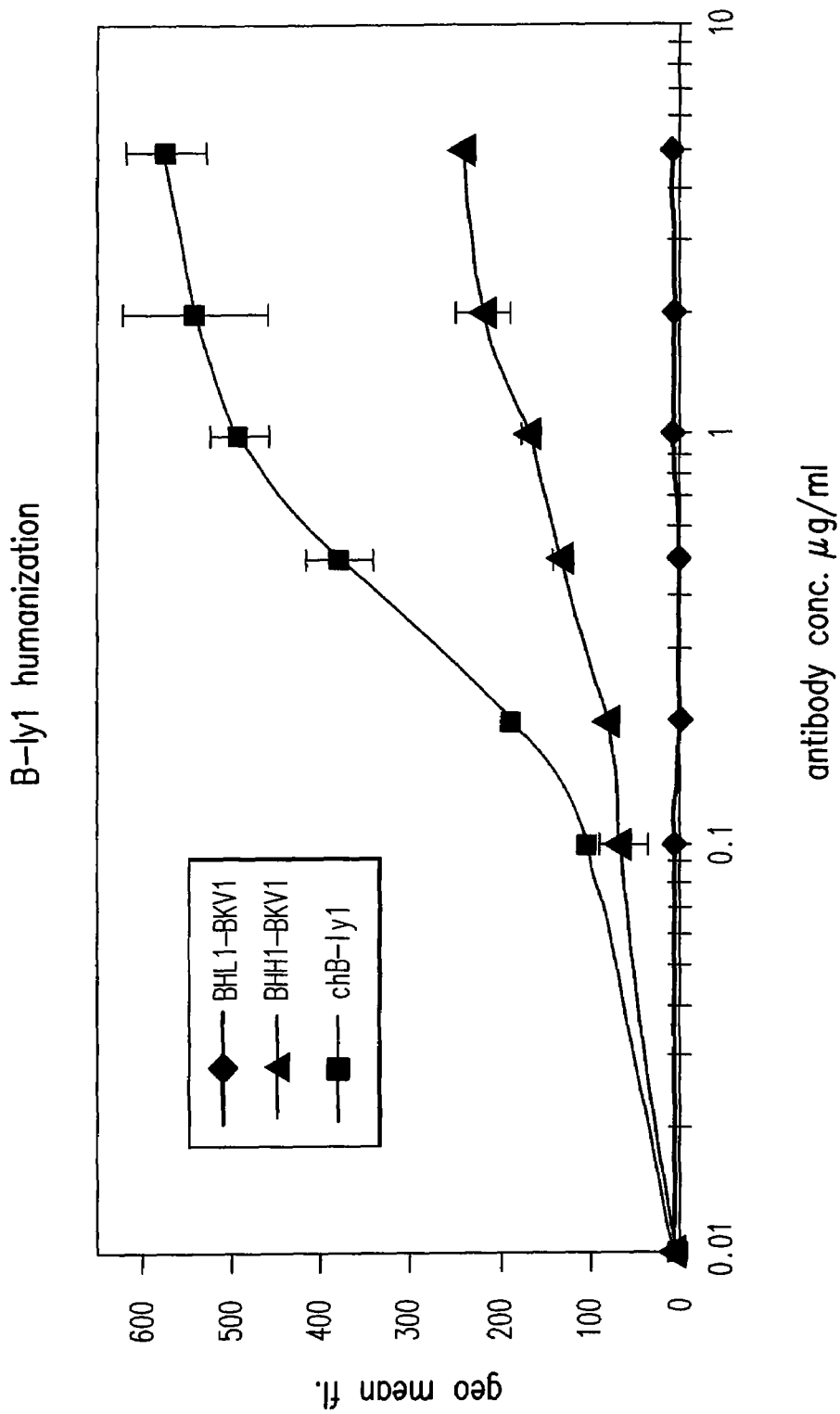
FIG. 12. The comparison of B-HL1, B-HH1, and the B-ly1 parental antibody. The data showed absence of any binding activity in the B-HL1 construct, and about half of the binding intensity/stoichiometry of B-HH1 compared to B-ly1. Both B-HL1, as well as B-HH1, are designed based on acceptor frameworks derived from the human VH1 class. Among other differences, position 71 (Kabat numbering) of the B-HL1 construct is a striking difference, indicating its putative importance for antigen binding.
Figure 13:
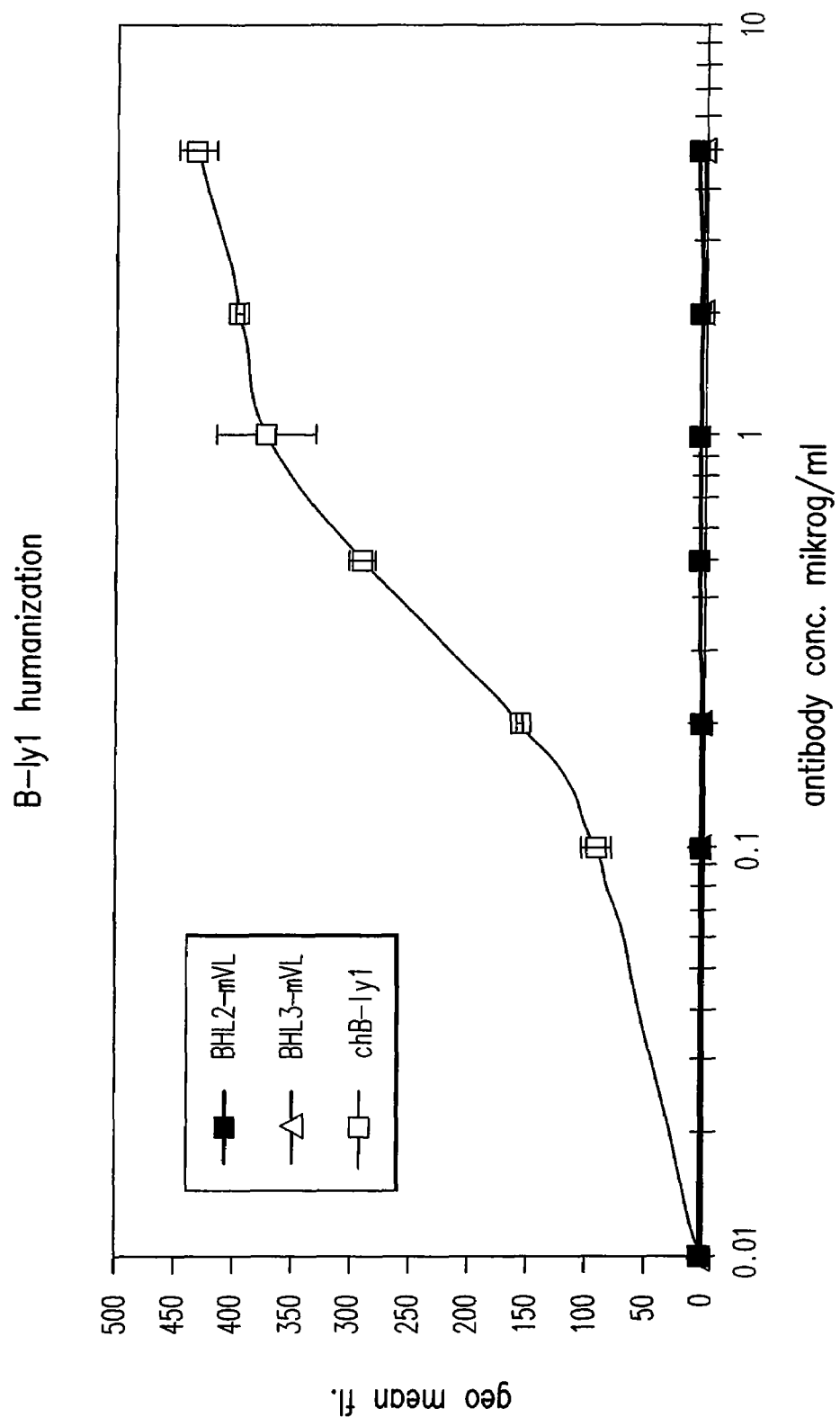
FIG. 13. Fluorocytometric analysis of the capacity of the anti-CD20 antibody to its antigen. The data showed that the B-HL2 and B-HL3 constructs do not display CD-20 binding activity.

The comparison of the B-HL1, B-HH1, and the chimeric chB-ly1 parental antibody showed absence of any binding activity in the B-HL1 construct, and about half of the binding intensity/stoichiometry of the B-HH1 compared to B-ly1 (FIG. 12). Both the B-HL1 as well as the B-HH1 are designed based on acceptor frameworks derived from the human VH1 class. Among other differences, position 71 (Kabat numbering; Kabat position 71 corresponds to position 72 of SEQ ID NO:48) of the B-HL1 construct is a striking difference, indicating its putative importance for antigen binding.

When comparing the antigen binding data of FIGS. 9 to 13, the BHH2-KV1, BHL8-KV1, and BHL11-KV1 variants show the best binding affinity, among the different humanized antibody variants tested, to human CD20 on the surface of human cells . . . . The differences between B-HH2, on one hand, and B-HL8 and B-HL11 on the other hand are located in the FR1 and FR2 regions only, with all three CDRs being identical (compare, e.g., SEQ ID NOs: 32, 56, and 60, which are not numbered according to Kabat, but whose Kabat numbering can be readily determined by one of ordinary skill). B-HL8 and B-HL11 have their FR1 and FR2 sequences derived from the human VH3 class, whereas the complete B-HH2 framework is human VH1 derived. B-HL11 is a derivative of B-HL8 with the single mutation Glu1 Gln (position 1 is the same in both Kabat numbering and the conventional numbering system used in the sequence listing), with Gln being the amino acid residue in the B-HH2 construct. This means that Glu1Gln exchange does not alter binding affinity nor intensity. The other differences between B-HH2 and B-HL8 are 14 framework residues, of which one or more will influence the antigen binding behavior of this antibody.

Figure 14:
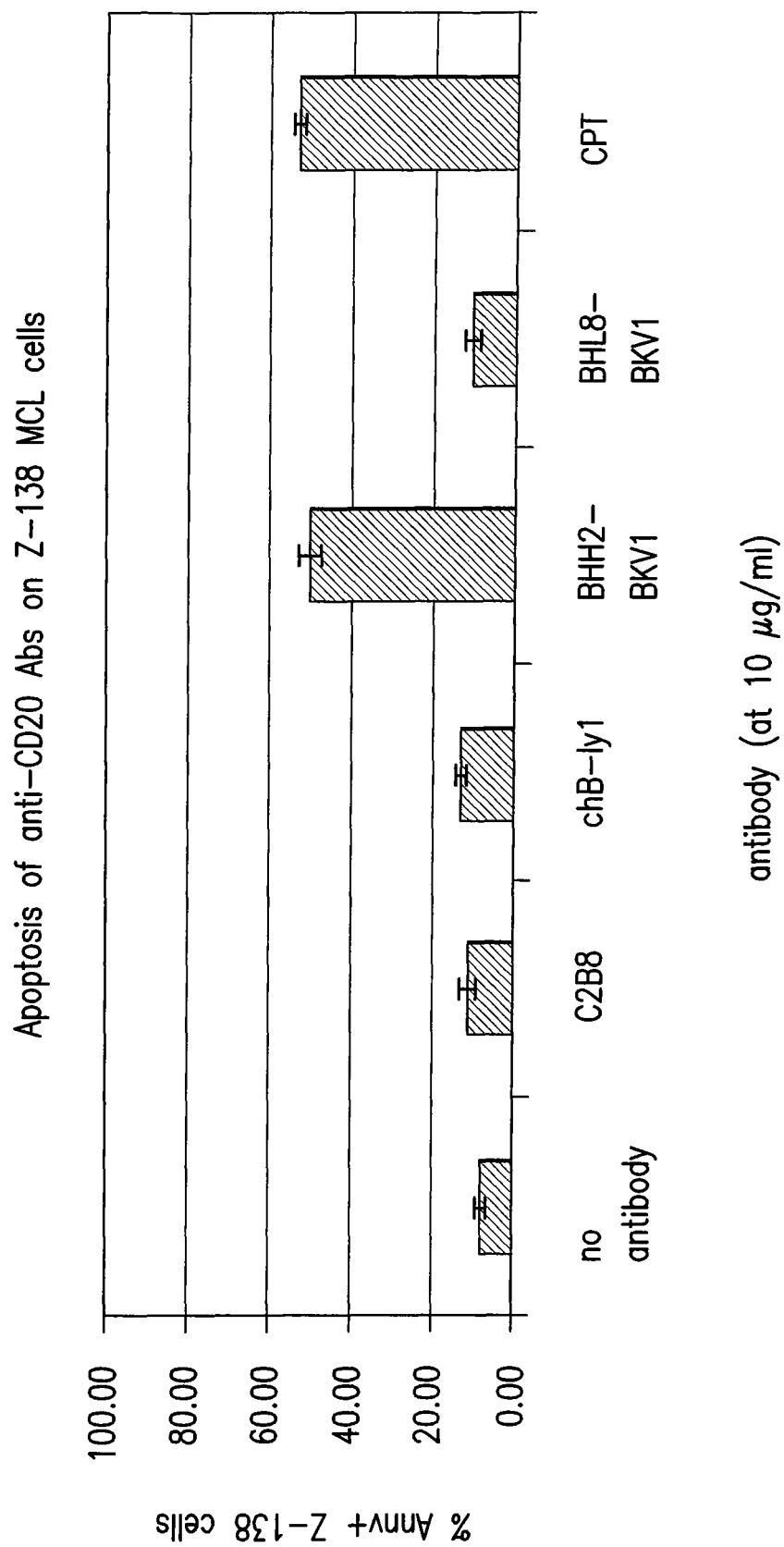
FIG. 14. Apoptosis of anti-CD20 antibodies on Z-138 MCL cells.
Figure 15:
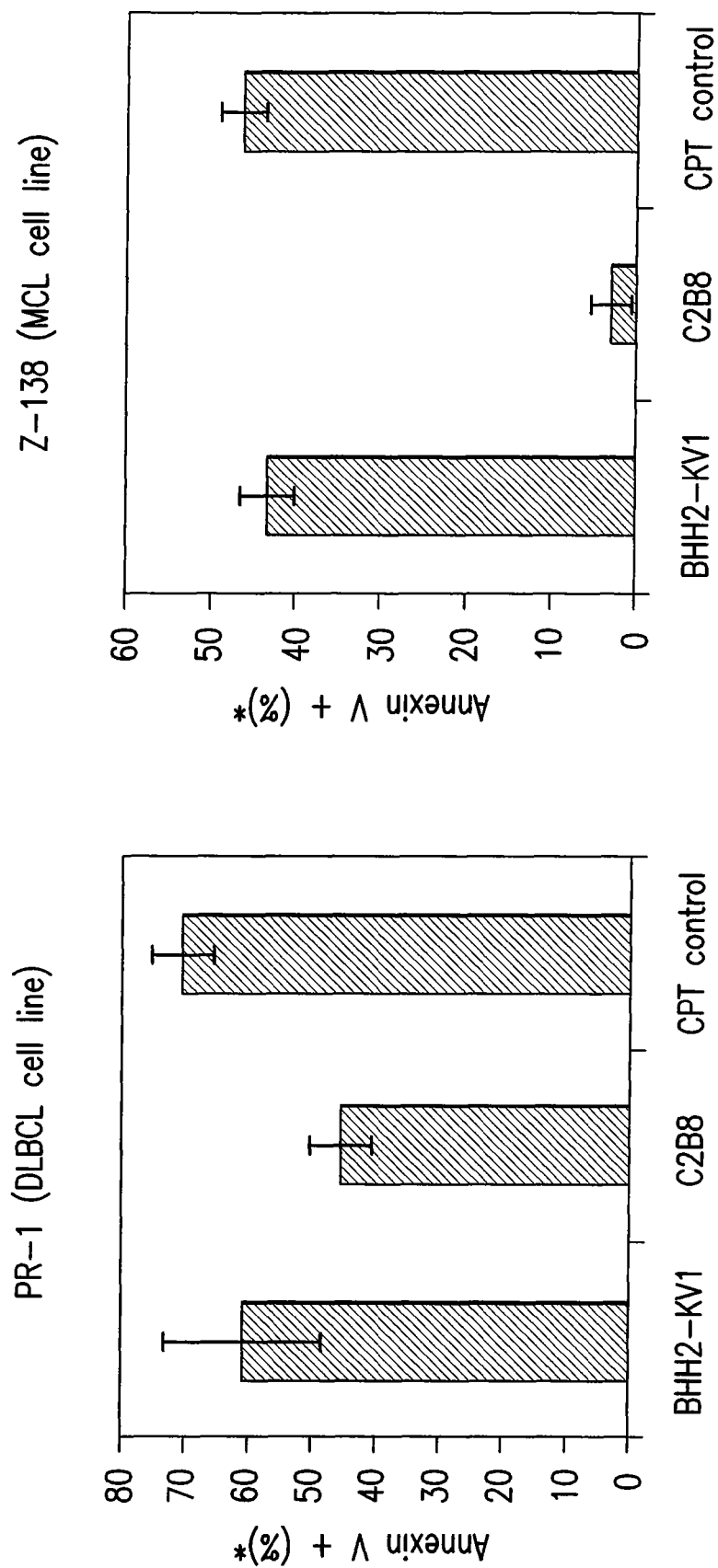
FIG. 15. Apoptosis by anti-CD20 antibodies. Assay details: $5\times10^5$ cells/well were seeded in 24-well plates ($5\times10^5$ cells/ml) in culture medium. 10 mg of the respective Ab, PBS for the negative control or 5 mM Camptothecin (CPT) positive control were added to the wells. Samples were incubated o/n (16 h), stained with AnnV-FITC and analysed by FACS. Assay was done in triplicates (*): Signal for PBS alone subtracted (PBS alone gave 8% and 2% AnnV+ for PR-1 and Z-138 cells respectively). Antibodies used were: C2B8 (chimeric, non-glycoengineered); BHH2-KV1 (humanized, non-glycoengineered). Note: this assay does not involve any additional effector cells, just targets plus antibody or controls.
Figure 21:
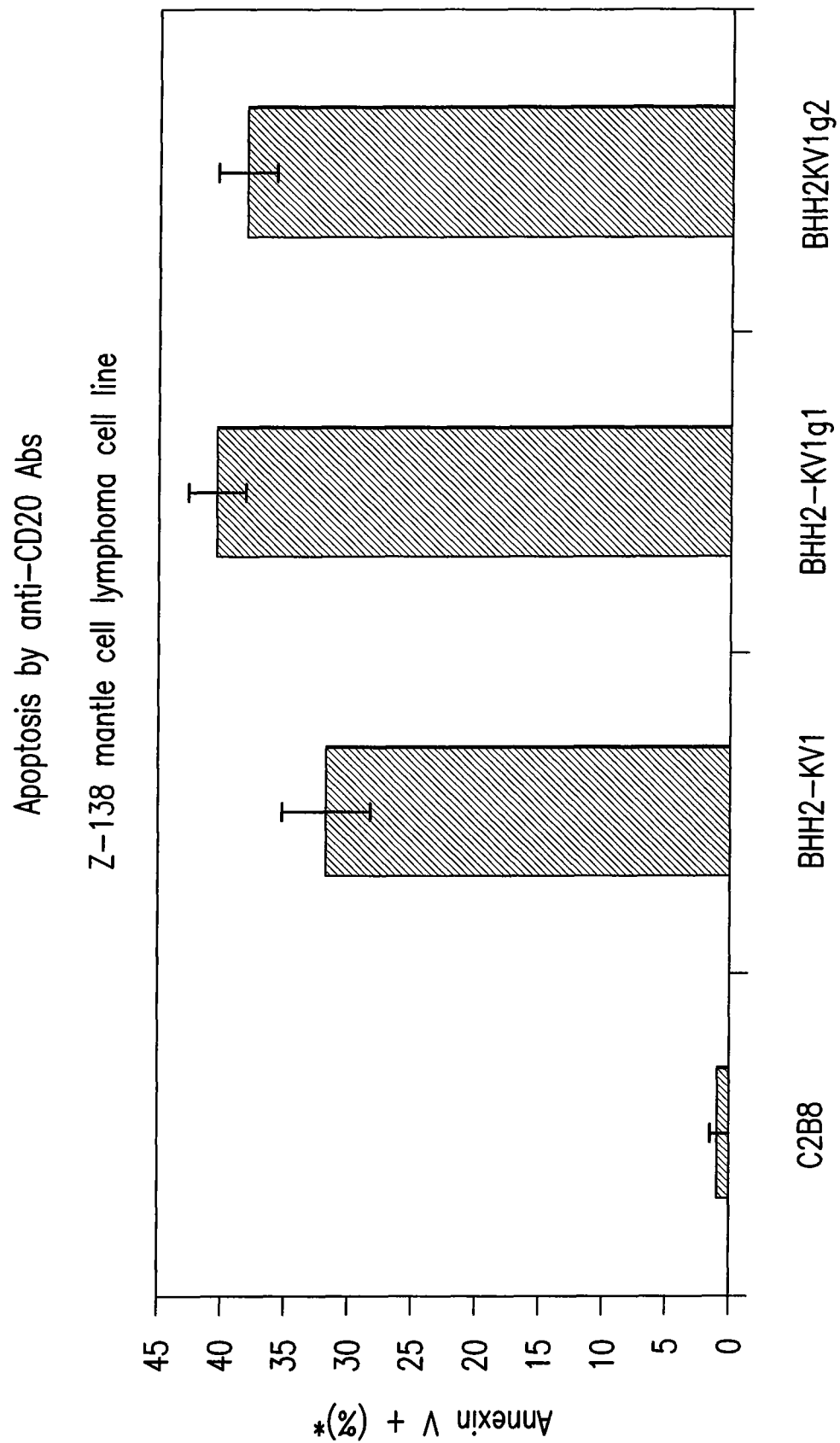
FIG. 21. Apoptosis of non-Fc engineered and Fc-engineered anti-CD20 antibodies on Z-138 MCL cells. Assay details: 5×105 cells/well were seeded in 24-well plates (5×105 cells/ml) in culture medium. 10 mg of the respective Ab, PBS for the negative control were added to the wells. Samples were incubated o/n (16 h), stained with AnnV-FITC and analysed by FACS. Assay was done in triplicates. Abs used: C2B8=rituximab (chimeric, non-glycoengineered form, same as commercial form); BHH2-KV1 (humanized, non-glycoengineered—see FIG. 6 for glycosylation profile); BHH2-KV1g1 (humanized, glycoengineered—see FIG. 7 for glycosylation profile); BHH2-KV1g2 (humanized, glycoengineered—see FIG. 8 for glycosylation profile). Note: this assay does not involve any additional effector cells, just targets plus antibody or controls. (*): Signal for PBS alone subtracted.

The B-HL4 construct is derived from the B-HH2 antibody by replacing the FR1 of the B-HH2 with that of the human germ line sequence VH1_45. This construct shows greatly diminished antigen binding capacity, despite having different amino acids at only three positions within FR1. These residues are located at positions 2, 14, and 30 (Kabat numbering). Of these, position 30 could be an influential position, since it is part of the Chothia definition of CDR1. Overall analysis of all the binding curves from FIGS. 9 to 13 indicates that the following humanized B-ly1 heavy chain residues (Kabat numbering) are important for binding to CD20: N35 (end of Kabat CDR1), full Kabat CDR1, full Kabat CDR2 and full Kabat CDR3, residues A71 and R94 (in this case R94 cannot be replaced by a threonine) and Y27. A28 and S30 also contribute to a lesser extent. In addition, Kabat CDR3 and all canonical residues are important for antigen binding. No back mutations were introduced in the humanized light chain, which had the full Kabat CDR1, CDR2 and CDR3 grafted. In induction of apoptosis (FIGS. 14, 15 and 21), the most potent variant was humanized B-ly1 variant BHH2-KV1 (even more potent than the original chB-ly1 and a lot more potent than an antibody with a sequence identical to rituximab, C2B8). Other humanized variants (derivatives of BHL8) that can recover the increased apoptosis are: B-HL12 to B-HL17 (see Table) and BHH8 (mixed frameworks) and BHH9 ("mixed frameworks" with one back mutation, S30T). Positions 9 and 48 (Kabat numbering) can contact the antigen. Variants BHH4 to BHH7 are other humanized B-ly1 variants that do not introduce additional non-human sequences.

Important properties of the humanized B-ly1 antibody are that it is a type II anti-CD20 antibody as defined in Cragg, M. S, and Glennie, M. J., *Blood* 103(7):2738-2743 (April 2004); . It therefore did not induce, upon binding to CD20, any significant resistance to non-ionic detergent extraction of CD20 from the surface of CD20+ human cells, using the assay described for this purposes in Polyak, M. J. and Deans, J. P., *Blood* 99(9):3256-3262 (2002). It certainly induced significantly less resistance to non-ionic detergent extraction of CD20 than the C2B8 antibody does (another anti-CD20 antibody with identical sequence to rituximab, (See U.S. Pat. Pub. No. 2003 0003097 to Reff). As expected of a type II anti-CD20 antibody, the humanized B-ly1 did not have any significant complement mediated lysis activity and certainly a lot complement mediated lysis activity than the anti-CD20 antibody C2B8 (chimeric IgG1 with identical sequence to rituximab). Another important property of the humanized B-ly1 antibody was that it was very potent in the homotypic aggregation assay. In this assay CD20-positive human cells, Daudi cells, were incubated in cell culture medium for up to 24 hours at 37° C. in a 5% CO2 atmosphere in a mammalian cell incubator as described in detail in (Deans reference), with the antibody at a concentration of 1 microgram per ml and in parallel at a concentration of 5 micrograms per ml. As a comparison, control, parallel incubation of the cells were done under identical conditions but using the anti-CD20 antibody C2B8. At different time points, including 8 hours and 24 hours of incubation, the cells were inspected visually using a microscope. It was found that the humanized B-ly1 antibody led to strong homotypic aggregation, with aggregates being significantly larger that those induced by addition of the C2B8 control antibody. In addition, and consistent with the antibody being anti-CD20 type II, it induced higher levels of apoptosis when CD20-positive human cells were incubated with the humanized B-ly1 antibody, relative to a control under identical conditions using the C2B8 chimeric IgG1 antibody with identical sequence to rituximab.

Figure 16:
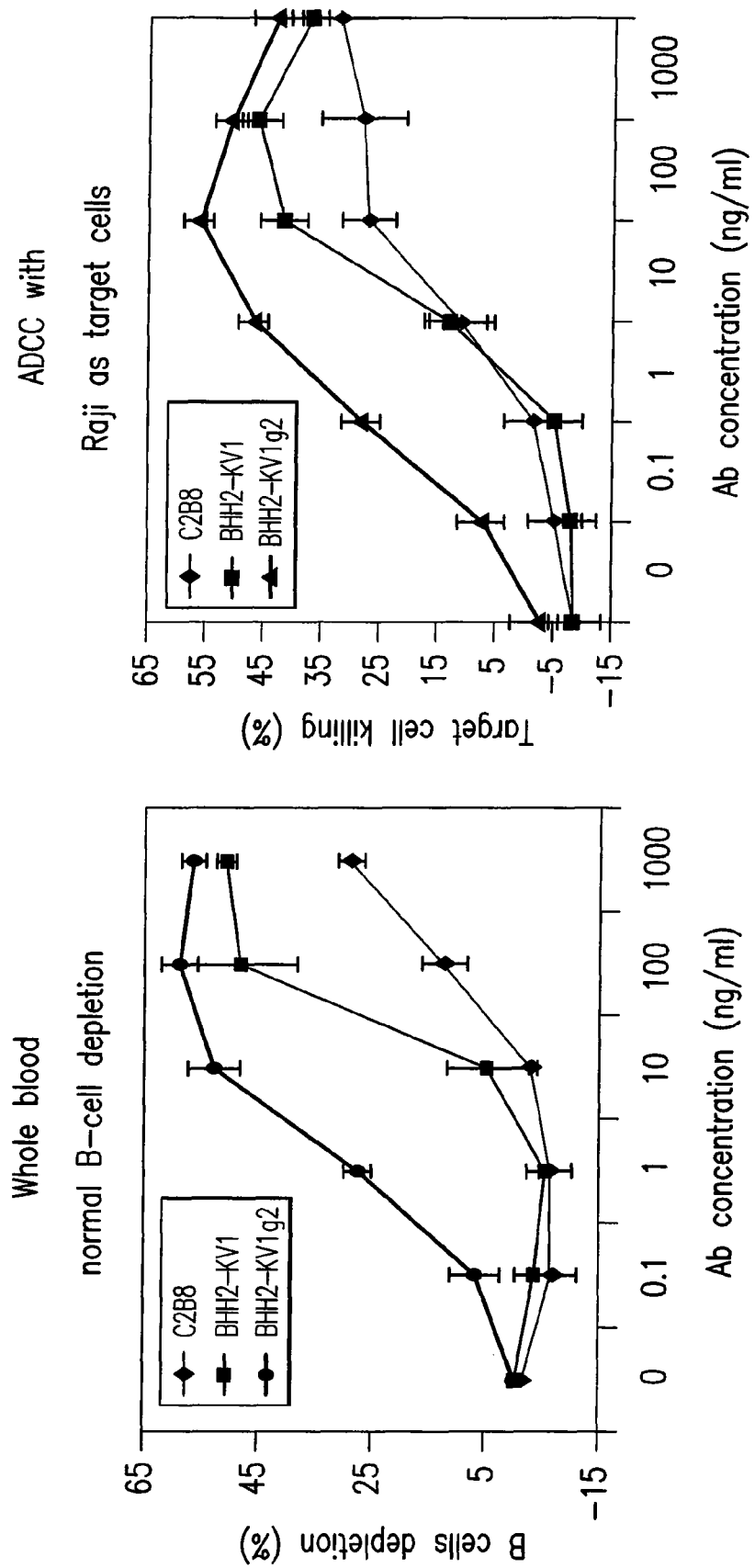
FIG. 16. Target-cell killing by anti-CD20 antibodies with immune effector cells. Assay details: B-cell depletion in normal whole blood overnight incubation and analysis for CD19+/CD3+ by FACS. ADCC using PBMCs as effectors, 4 h incubation, 25:1 effector:target ratio, target-killing measured by Calcein-retention relative to detergent-lysis (100%) and to lysis without Ab (0%). Antibodies used: C2B8 (chimeric, non-glycoengineered form); BHH2-KV1-wt (humanized, non-glycoengineered form of BHH2-KV1); BHH2-KV1-GE (humanized, glycoengineered form of BHH2-KV1).
Figure 17:
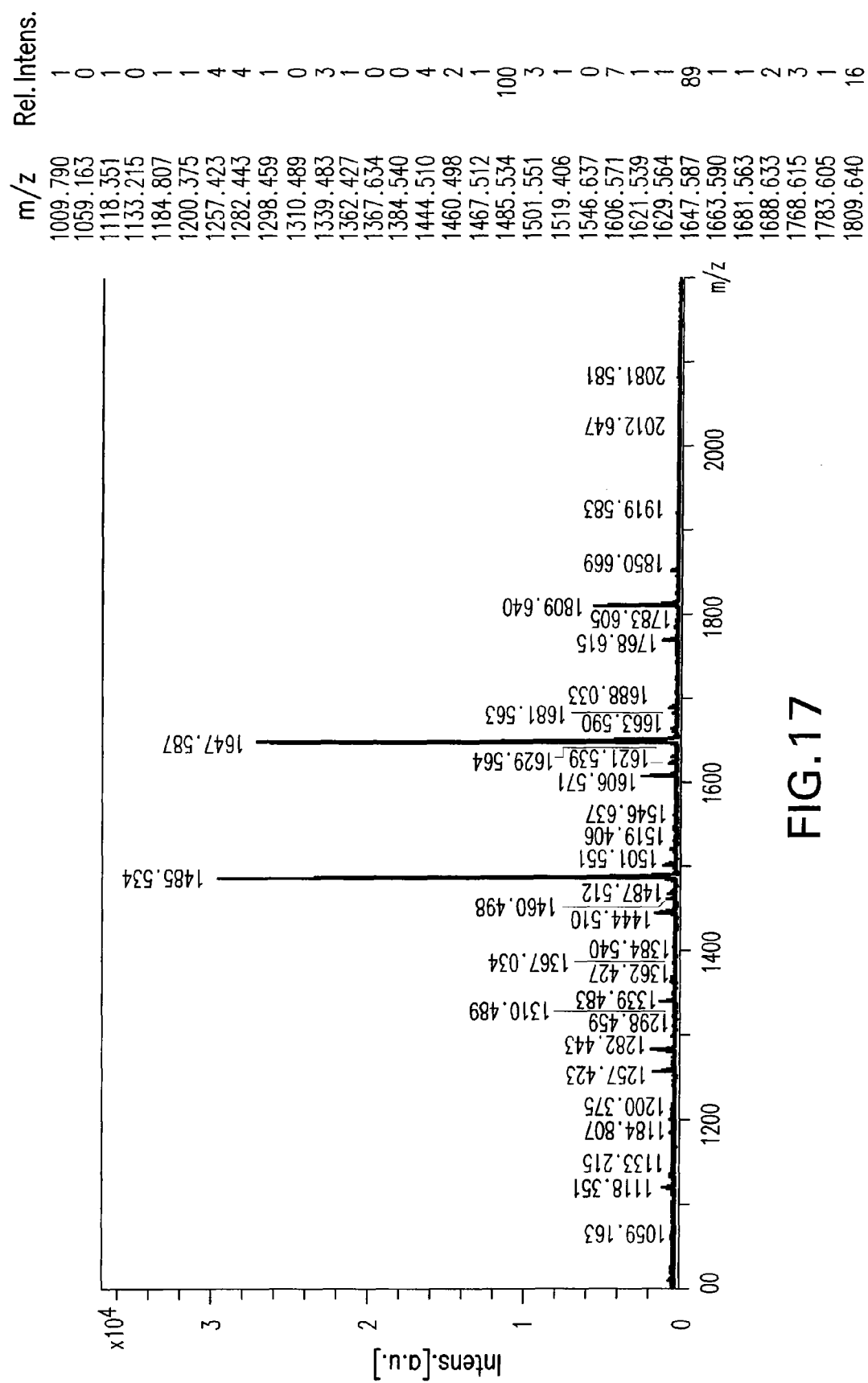
FIG. 17. MALDI/TOF-MS profile of PNGaseF-released Fc-oligosaccharides of unmodified, nonglycoengineered BHH2-KV1 humanized IgG1 B-ly1 anti-human CD20 antibody.
Figure 18:
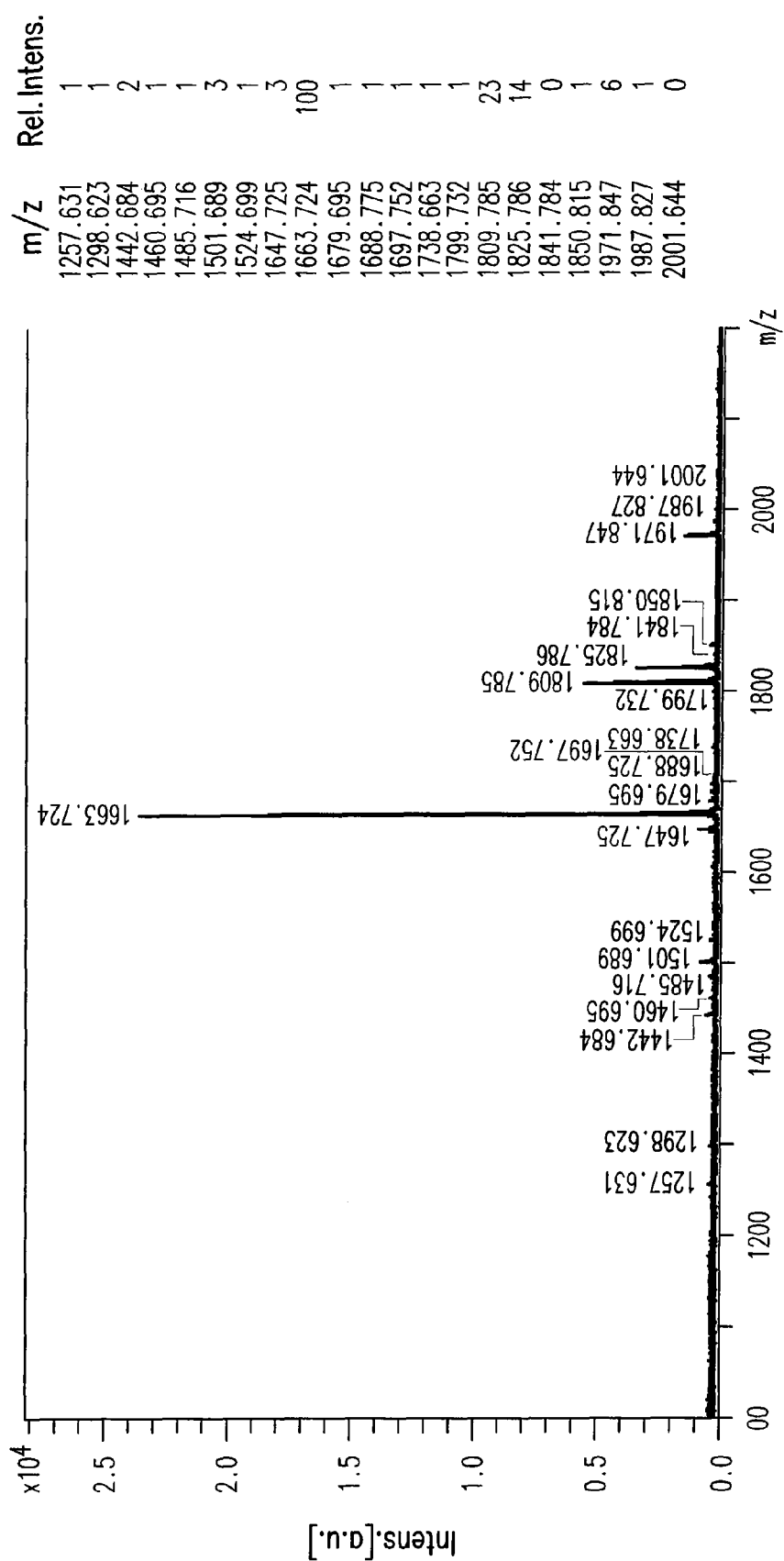
FIG. 18. MALDI/TOF-MS profile of PNGaseF-released Fc-oligosaccharides of glycoengineered BHH2-KV1g1 humanized IgG1 B-ly1 anti-human CD20 antibody. Glycoengineering done by co-expression in host cells of antibody genes and gene encoding enzyme with β-1,4-N-acetylglucosaminyltransferase III (GnT-III) catalytic activity.
Figure 19:
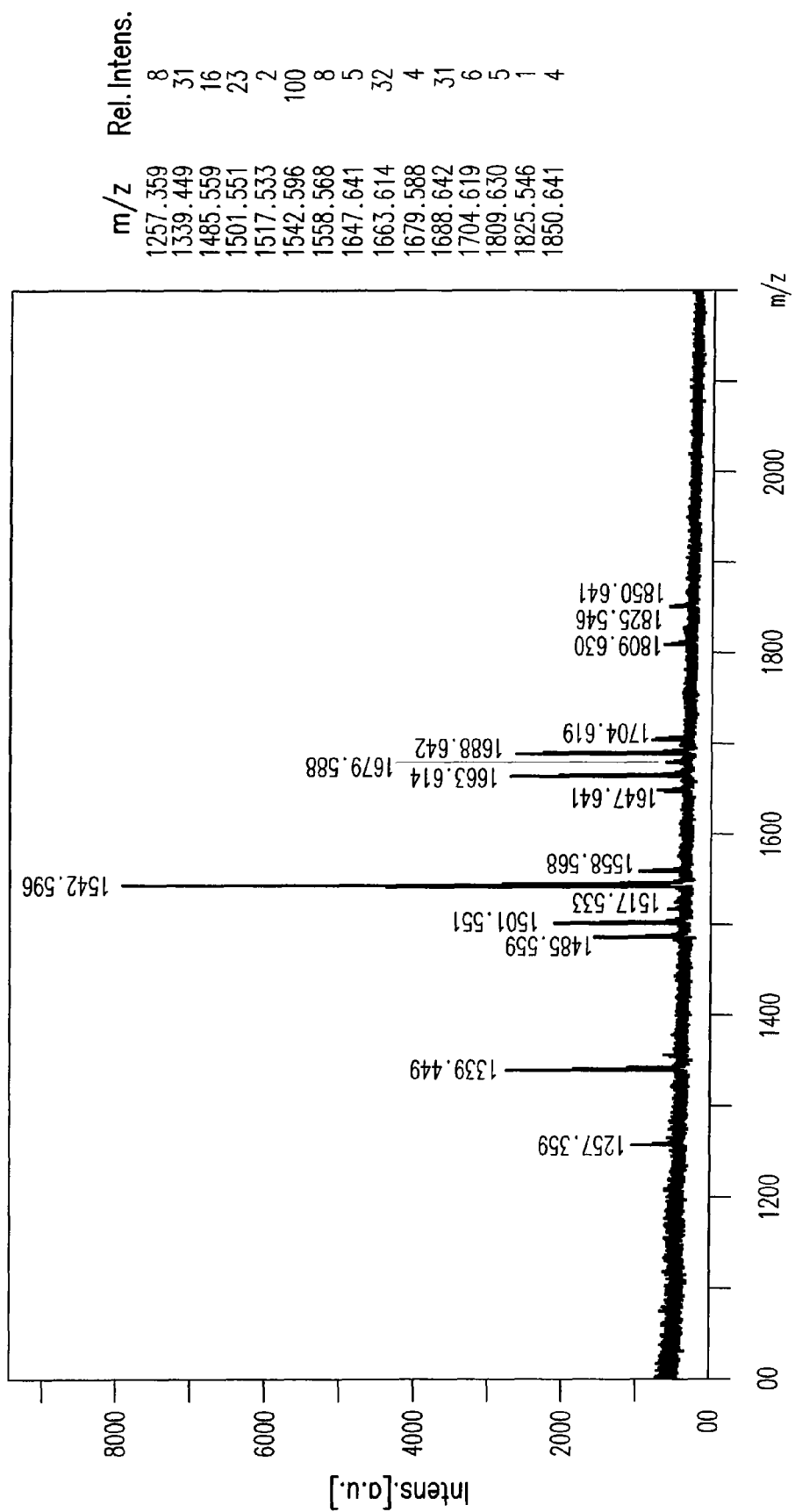
FIG. 19. MALDI/TOF-MS profile of PNGaseF-released Fc-oligosaccharides of glycoengineered BHH2-KV1g2 humanized IgG1 B-ly1 anti-human CD20 antibody. Glycoengineering done by co-expression in host cells of antibody genes and genes encoding enzyme with β-1,4-N-acetylglucosaminyltransferase III (GnT-III) catalytic activity and encoding enzyme with Golgi α-mannosidase II catalytic activity.
Figure 20:
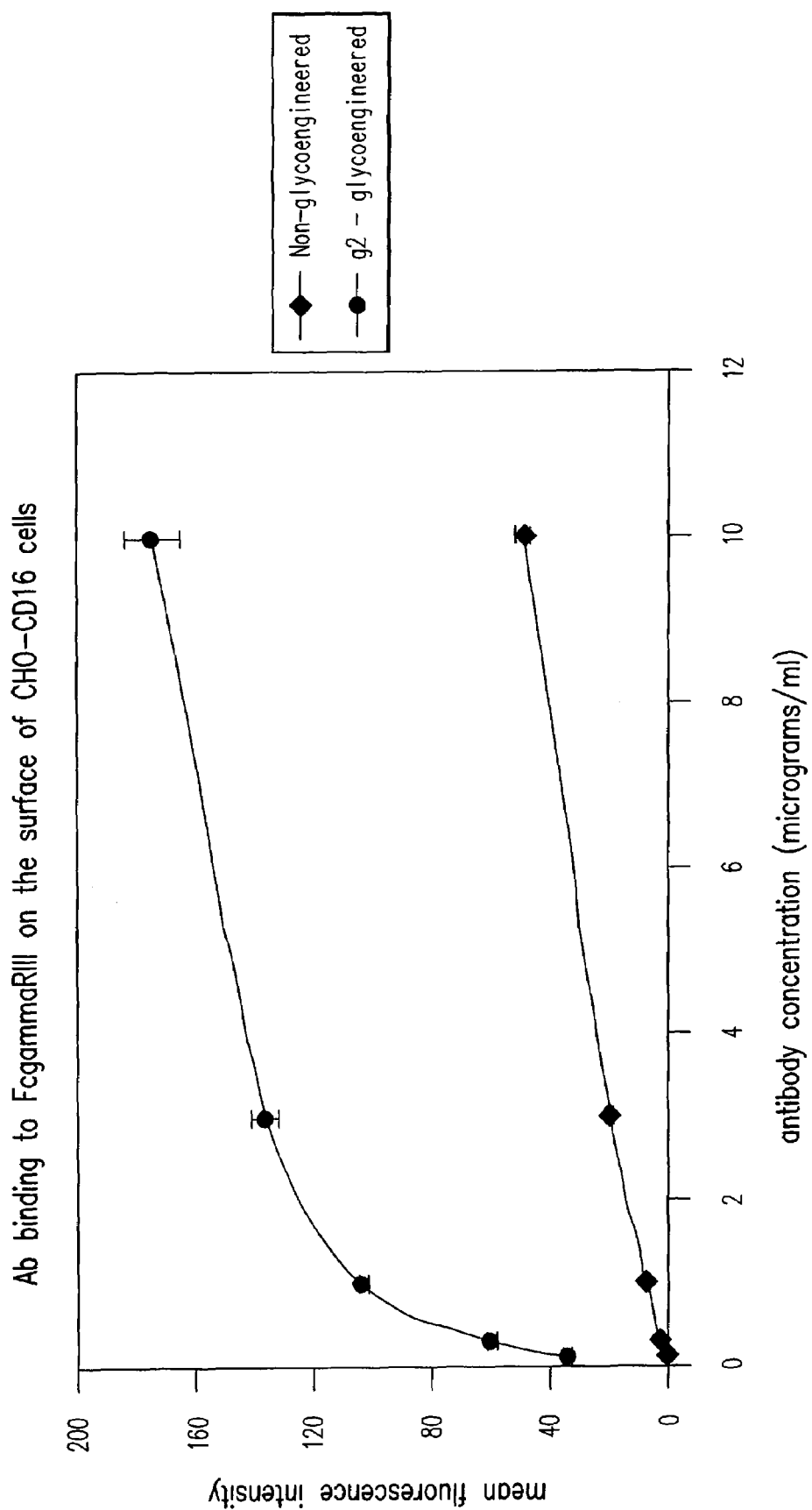
FIG. 20. Binding of non-glycoengineered and glycoengineered antibodies to human FcgammaRIIIa receptor displayed on the surface of recombinant CHO-CD16 cells.

Glycoengineered variants of the humanized antibodies were produced by co-expression of GnTIII glycosyltransferase, together with the antibody genes, in mammalian cells. This led to an increase in the fraction of non-fucosylated oligosaccharides attached to the Fc region of the antibodies, including bisected non-fucosylated oligosaccharides, as has been described in WO 2004/065540 (FIGS. 17-19). The glycoengineered antibodies had significantly higher levels of binding to human FcgammaRIII receptors (FIG. 20) and ADCC activity as well (FIG. 16), relative to the non-glycoengineered antibody and relative to the C2B8 antibody. The humanized B-ly1 antibody was also more potent at inducing human B-cell depletion in a whole blood assay (FIG. 16) than the control C2B8 antibody. This was true both for the non-glycoengineered B-ly1 antibody and for the glycoengineered version of it. The glycoengineered antibody was approximately 1000-fold more potent than the C2B8 control anti-CD20 antibody in depleting B-cells in the whole blood assay. This comparison is important both for the non-glycoengineered and for the glycoengineered humanized forms of B-ly1 antibody, because it showed that in assays that combined Fc receptor-dependent activities, such as ADCC, plus complement mediated lysis, plus induction of apoptosis, that both forms of B-ly1 were significantly more potent that C2B8, although both forms of B-ly1 have dramatically lower complement mediated lysis activity. The ADCC, Fc receptor-dependent cell killing activities and apoptosis induction were present in this superior activity of the humanized B-ly1 antibody variants. Furthermore, in the apoptosis assay, both the glycoengineered and non-glycoengineered forms of this type II anti-CD20 antibody were potent, with the Fc-engineered variants with increased binding affinity to Fcgamma receptors being even more potent in apoptosis induction than the non-Fc-engineered variant, and with all variants being significantly more potent than the control antibody C2B8. The exact mechanism for enhanced homotypic aggregation and induction of apoptopsis mediated by type II anti-CD20 antibodies is not known and concomitant binding to other molecules on the surface of CD20-positive cells, such as Fc gamma receptors, can influence this important property. It was therefore important to demonstrate that anti-CD20 antibodies of type II that have been engineered in their Fc region for increased binding affinity to Fc gamma receptors, including FcgammaRIII and with an associated increase in ADCC activity, were still able to induce strong apoptosis, even higher than the non-Fc-engineered, and homotypic aggregation. Apoptopsis induction is important as in vivo, as there are locations in the body where the target CD20-positive cells can be found, but were access to FcgammaRIII-positive cells is more difficult than in blood, such locations are, for example, lymph nodes. In those locations, the induction of apoptosis by the anti-CD20 antibody itself can be crucial for good efficacy of the anti-CD20 antibody therapy in humans, both for the treatment of haematological malignancies such as non-Hodgkins lymphomas and B-cell chronic lymphocytic leukaemia, and for the treatment of autoimmune diseases such as rheumatoid arthritis and lupus via a B-cell depletion approach. The increased binding affinity to FcgammaRIII and higher ADCC of the humanized, Fc-engineered type II anti-CD20 antibody can also be a very important attribute for such therapies. Finally, the reduced or negligible complement mediated lysis activity of this type II anti-CD20 antibodies, including humanized and Fc-engineered variants, can also be important higher complement activation by anti-CD20 antibodies has been correlated with increased, undesirable side-effects

What is claimed is:

1. An antibody that binds to human CD20 comprising:
   (a) a heavy chain variable region (VH) comprising the amino acid sequence of SEQ ID NO:40; and
   (b) a light chain variable region (VL) comprising the amino acid sequence of SEQ ID NO:76.

2. The antibody of claim 1, wherein the antibody comprises a human Fc region.

3. The antibody of claim 2, wherein the human Fc region is a human IgG1 Fc region.

4. The antibody of claim 2, wherein the Fc region comprises an N-linked oligosaccharide that has been modified.

5. The antibody of claim 4, wherein N-linked oligosaccharides of the Fc region have reduced fucose residues as compared to an antibody with non-modified N-linked oligosaccharides.

6. The antibody of claim 4, wherein the modified N-linked oligosaccharide comprises a bisected oligosaccharide.

7. The antibody of claim 6, wherein the bisected oligosaccharide is a bisected complex oligosaccharide.

8. The antibody of claim 4, wherein the modified N-linked oligosaccharide comprises a bisected, nonfucosylated oligosaccharide.

9. The antibody of claim 8, wherein the bisected, nonfucosylated oligosaccharide is a hybrid type.

10. The antibody of claim 8, wherein the bisected, nonfucosylated oligosaccharide is a complex type.

11. The antibody of claim 2, wherein the Fc region comprises an N-linked oligosaccharide lacking fucose.

12. The antibody of claim 1, wherein the antibody is an antigen-binding fragment.

13. An antibody produced by a method comprising: culturing a host cell comprising one or more polynucleotides encoding an antibody comprising a variable heavy chain region (VH) comprising the amino acid sequence of SEQ ID NO:40 and a variable light chain region (VL) comprising the amino acid sequence of SEQ ID NO:76, under conditions that permit expression of the antibody, wherein the antibody binds to human CD20.

14. The antibody of claim 13, wherein the method further comprises recovering the antibody expressed by the host cell.

15. The antibody of claim 13, wherein the host cell is a mammalian cell or a yeast cell.

16. The antibody of claim 15, wherein the mammalian cell is a CHO cell.

* * * * *

UNITED STATES PATENT AND TRADEMARK OFFICE
CERTIFICATE OF CORRECTION

PATENT NO. : 8,883,980 B2  
APPLICATION NO. : 11/889975  
DATED : November 11, 2014  
INVENTOR(S) : Pablo Umaña et al.

Page 1 of 1

It is certified that error appears in the above-identified patent and that said Letters Patent is hereby corrected as shown below:

In the Specification

At Column 3, line number 55, please replace "iodine -±31" with --iodine -131--;

At Column 23, line number 53, please replace "at lest" with --at least--;

At Column 37, line number 11, please replace "a 1-6" with --α 1-6--;

At Column 49, line number 57, please replace "3040" with --30-40--;

At Column 50, line number 65, please replace "370" with --37°--; and

At Column 55, line number 1, please replace "$_{56}$°" with --56°--.

Signed and Sealed this  
Twenty-ninth Day of September, 2015

Michelle K. Lee  
*Director of the United States Patent and Trademark Office*

SEQUENCE LISTING

```
<160> NUMBER OF SEQ ID NOS: 86

<210> SEQ ID NO 1
<211> LENGTH: 112
<212> TYPE: PRT
<213> ORGANISM: Mus sp.

<400> SEQUENCE: 1

Gly Pro Glu Leu Val Lys Pro Gly Ala Ser Val Lys Ile Ser Cys Lys
1               5                   10                  15

Ala Ser Gly Tyr Ala Phe Ser Tyr Ser Trp Met Asn Trp Val Lys Leu
            20                  25                  30

Arg Pro Gly Gln Gly Leu Glu Trp Ile Gly Arg Ile Phe Pro Gly Asp
        35                  40                  45

Gly Asp Thr Asp Tyr Asn Gly Lys Phe Lys Gly Lys Ala Thr Leu Thr
    50                  55                  60

Ala Asp Lys Ser Ser Asn Thr Ala Tyr Met Gln Leu Thr Ser Leu Thr
65                  70                  75                  80

Ser Val Asp Ser Ala Val Tyr Leu Cys Ala Arg Asn Val Phe Asp Gly
                85                  90                  95

Tyr Trp Leu Val Tyr Trp Gly Gln Gly Thr Leu Val Thr Val Ser Ala
            100                 105                 110

<210> SEQ ID NO 2
<211> LENGTH: 336
```

```
<212> TYPE: DNA
<213> ORGANISM: Mus sp.

<400> SEQUENCE: 2
ggacctgaac tggtgaagcc tggggcctca gtgaagattt cctgcaaagc ttctggctac    60
gcattcagtt actcttggat gaactgggtg aaactgaggc ctggacaggg tcttgagtgg   120
attggacgga ttttcctgg agatggggat actgactaca atgggaaatt caagggcaag    180
gccacactga ctgctgacaa atcctccaac acagcctaca tgcaactcac cagcctgacc   240
tctgtggact ctgcggtcta tttatgtgca agaaatgtct ttgatggtta ctggttagtt   300
tactggggcc aagggactct ggtcactgtc tctgca                              336

<210> SEQ ID NO 3
<211> LENGTH: 103
<212> TYPE: PRT
<213> ORGANISM: Mus sp.

<400> SEQUENCE: 3

Asn Pro Val Thr Leu Gly Thr Ser Ala Ser Ile Ser Cys Arg Ser Ser
1               5                   10                  15

Lys Ser Leu Leu His Ser Asn Gly Ile Thr Tyr Leu Tyr Trp Tyr Leu
            20                  25                  30

Gln Lys Pro Gly Gln Ser Pro Gln Leu Leu Ile Tyr Gln Met Ser Asn
        35                  40                  45

Leu Val Ser Gly Val Pro Asp Arg Phe Ser Ser Gly Ser Gly Thr
    50                  55                  60

Asp Phe Thr Leu Arg Ile Ser Arg Val Glu Ala Glu Asp Val Gly Val
65                  70                  75                  80

Tyr Tyr Cys Ala Gln Asn Leu Glu Leu Pro Tyr Thr Phe Gly Gly Gly
                85                  90                  95

Thr Lys Leu Glu Ile Lys Arg
            100

<210> SEQ ID NO 4
<211> LENGTH: 309
<212> TYPE: DNA
<213> ORGANISM: Mus sp.

<400> SEQUENCE: 4
aatccagtca ctcttggaac atcagcttcc atctcctgca ggtctagtaa gagtctccta    60
catagtaatg gcatcactta tttgtattgg tatctgcaga agccaggcca gtctcctcag   120
ctcctgattt atcagatgtc caaccttgtc tcaggagtcc cagacaggtt cagtagcagt   180
gggtcaggaa ctgatttcac actgagaatc agcagagtgg aggctgagga tgtgggtgtt   240
tattactgtg ctcaaaatct agaacttccg tacacgttcg gaggggggac caagctggaa   300
ataaaacgg                                                             309

<210> SEQ ID NO 5
<211> LENGTH: 15
<212> TYPE: DNA
<213> ORGANISM: Mus sp.

<400> SEQUENCE: 5
tactcttgga tgaac                                                      15

<210> SEQ ID NO 6
<211> LENGTH: 18
```

```
<212> TYPE: DNA
<213> ORGANISM: Mus sp.

<400> SEQUENCE: 6
ggctacgcat tcagttac                                                 18

<210> SEQ ID NO 7
<211> LENGTH: 30
<212> TYPE: DNA
<213> ORGANISM: Mus sp.

<400> SEQUENCE: 7
ggctacgcat tcagttactc ttggatgaac                                    30

<210> SEQ ID NO 8
<211> LENGTH: 48
<212> TYPE: DNA
<213> ORGANISM: Mus sp.

<400> SEQUENCE: 8
aggtctagta agagtctcct acatagtaat ggcatcactt atttgtat                48

<210> SEQ ID NO 9
<211> LENGTH: 21
<212> TYPE: DNA
<213> ORGANISM: Mus sp.

<400> SEQUENCE: 9
cagatgtcca accttgtctc a                                             21

<210> SEQ ID NO 10
<211> LENGTH: 27
<212> TYPE: DNA
<213> ORGANISM: Mus sp.

<400> SEQUENCE: 10
gctcaaaatc tagaacttcc gtacacg                                       27

<210> SEQ ID NO 11
<211> LENGTH: 1407
<212> TYPE: DNA
<213> ORGANISM: Artificial Sequence
<220> FEATURE:
<223> OTHER INFORMATION: Mouse-human chimeric cDNA

<400> SEQUENCE: 11
atgggttgga gcctcatctt gctcttcctt gtcgctgttg ctacgcgtgt cctgtccgag    60
gtcaagctgc agcagtctgg acctgaactg gtgaagcctg ggcctcagt gaagatttcc   120 tgcaaagctt ctggctacgc attcagttac tcttggatga actgggtgaa actgaggcct   180
ggacagggtc ttgagtggat tggacggatt tttcctggag atgggatac tgactacaat   240 gggaaattca gggcaaggc cacactgact gctgacaaat cctccaacac agcctacatg   300
caactcacca gcctgacctc tgtggactct gcggtctatt tatgtgcaag aaatgtcttt   360
gatggttact ggttagttta ctggggccaa gggactctgg tcactgtctc tgcagctagc   420
accaagggcc catcggtctt ccccctggca ccctcctcca agagcacctc tgggggcaca   480
gcggccctgg gctgcctggt caaggactac ttccccgaac cggtgacggt gtcgtggaac   540
tcaggcgccc tgaccagcgg cgtgcacacc ttccggctg tcctacagtc ctcaggactc   600
tactccctca gcagcgtggt gaccgtgccc tccagcagct gggcaccca gacctacatc   660
```

```
tgcaacgtga atcacaagcc cagcaacacc aaggtggaca agaaagcaga gcccaaatct      720
tgtgacaaaa ctcacacatg cccaccgtgc ccagcacctg aactcctggg gggaccgtca      780
gtcttcctct tccccccaaa acccaaggac accctcatga tctcccggac ccctgaggtc      840
acatgcgtgg tggtggacgt gagccacgaa gaccctgagg tcaagttcaa ctggtacgtg      900
gacggcgtgg aggtgcataa tgccaagaca aagccgcggg aggagcagta caacagcacg      960
taccgtgtgg tcagcgtcct caccgtcctg caccaggact ggctgaatgg caaggagtac     1020
aagtgcaagg tctccaacaa agccctccca gcccccatcg agaaaaccat ctccaaagcc     1080
aaagggcagc cccgagaacc acaggtgtac accctgcccc catcccggga tgagctgacc     1140
aagaaccagg tcagcctgac ctgcctggtc aaaggcttct atcccagcga catcgccgtg     1200
gagtgggaga gcaatgggca gccggagaac aactacaaga ccacgcctcc cgtgctggac     1260
tccgacggct ccttcttcct ctacagcaag ctcaccgtgg acaagagcag gtggcagcag     1320
gggaacgtct tctcatgctc cgtgatgcat gaggctctgc acaaccacta cacgcagaag     1380
agcctctccc tgtctccggg taaatga                                        1407
```

<210> SEQ ID NO 12
<211> LENGTH: 720
<212> TYPE: DNA
<213> ORGANISM: Artificial Sequence
<220> FEATURE:
<223> OTHER INFORMATION: Mouse-human chimeric cDNA

<400> SEQUENCE: 12

```
atggatttc aggtgcagat tatcagcttc ctgctaatca gtgcttcagt cataatgtcc        60
agaggagaca ttgtgctcac ccaaactaca aatccagtca ctcttggaac atcagcttcc      120
atctcctgca ggtctagtaa gagtctccta catagtaatg gcatcactta tttgtattgg      180
tatctgcaga agccaggcca gtctcctcag ctcctgattt atcagatgtc caaccttgtc      240
tcaggagtcc cagacaggtt cagtagcagt gggtcaggaa ctgatttcac actgagaatc      300
agcagagtgg aggctgagga tgtgggtgtt tattactgtg ctcaaaatct agaacttccg      360
tacacgttcg gaggggggac caagctggaa ataaaacgta cggtggctgc accatctgtc      420
ttcatcttcc cgccatctga tgagcagttg aaatctggaa ctgcctctgt tgtgtgcctg      480
ctgaataact tctatcccag agaggccaaa gtacagtgga aggtggataa cgccctccaa      540
tcgggtaact cccaggagag tgtcacagag caggacagca aggacagcac ctacagcctc      600
agcagcaccc tgacgctgag caaagcagac tacgagaaac acaaagtcta cgcctgcgaa      660
gtcacccatc agggcctgag ctcgcccgtc acaaagagct tcaacagggg agagtgttag      720
```

<210> SEQ ID NO 13
<211> LENGTH: 468
<212> TYPE: PRT
<213> ORGANISM: Artificial Sequence
<220> FEATURE:
<223> OTHER INFORMATION: Mouse-human chimeric polypeptide

<400> SEQUENCE: 13

```
Met Gly Trp Ser Leu Ile Leu Leu Phe Leu Val Ala Val Ala Thr Arg
1               5                   10                  15

Val Leu Ser Glu Val Lys Leu Gln Gln Ser Gly Pro Glu Leu Val Lys
                20                  25                  30

Pro Gly Ala Ser Val Lys Ile Ser Cys Lys Ala Ser Gly Tyr Ala Phe
            35                  40                  45
```

```
Ser Tyr Ser Trp Met Asn Trp Val Lys Leu Arg Pro Gly Gln Gly Leu
     50                   55                  60
Glu Trp Ile Gly Arg Ile Phe Pro Gly Asp Gly Asp Thr Asp Tyr Asn
 65              70                  75                      80
Gly Lys Phe Lys Gly Lys Ala Thr Leu Thr Ala Asp Lys Ser Ser Asn
                 85                  90                  95
Thr Ala Tyr Met Gln Leu Thr Ser Leu Thr Ser Val Asp Ser Ala Val
            100                 105                 110
Tyr Leu Cys Ala Arg Asn Val Phe Asp Gly Tyr Trp Leu Val Tyr Trp
            115                 120                 125
Gly Gln Gly Thr Leu Val Thr Val Ser Ala Ala Ser Thr Lys Gly Pro
        130                 135                 140
Ser Val Phe Pro Leu Ala Pro Ser Ser Lys Ser Thr Ser Gly Gly Thr
145                 150                 155                 160
Ala Ala Leu Gly Cys Leu Val Lys Asp Tyr Phe Pro Glu Pro Val Thr
                165                 170                 175
Val Ser Trp Asn Ser Gly Ala Leu Thr Ser Gly Val His Thr Phe Pro
            180                 185                 190
Ala Val Leu Gln Ser Ser Gly Leu Tyr Ser Leu Ser Ser Val Val Thr
            195                 200                 205
Val Pro Ser Ser Ser Leu Gly Thr Gln Thr Tyr Ile Cys Asn Val Asn
        210                 215                 220
His Lys Pro Ser Asn Thr Lys Val Asp Lys Lys Ala Glu Pro Lys Ser
225                 230                 235                 240
Cys Asp Lys Thr His Thr Cys Pro Pro Cys Pro Ala Pro Glu Leu Leu
                245                 250                 255
Gly Gly Pro Ser Val Phe Leu Phe Pro Pro Lys Pro Lys Asp Thr Leu
            260                 265                 270
Met Ile Ser Arg Thr Pro Glu Val Thr Cys Val Val Val Asp Val Ser
        275                 280                 285
His Glu Asp Pro Glu Val Lys Phe Asn Trp Tyr Val Asp Gly Val Glu
290                 295                 300
Val His Asn Ala Lys Thr Lys Pro Arg Glu Glu Gln Tyr Asn Ser Thr
305                 310                 315                 320
Tyr Arg Val Val Ser Val Leu Thr Val Leu His Gln Asp Trp Leu Asn
                325                 330                 335
Gly Lys Glu Tyr Lys Cys Lys Val Ser Asn Lys Ala Leu Pro Ala Pro
            340                 345                 350
Ile Glu Lys Thr Ile Ser Lys Ala Lys Gly Gln Pro Arg Glu Pro Gln
        355                 360                 365
Val Tyr Thr Leu Pro Pro Ser Arg Asp Glu Leu Thr Lys Asn Gln Val
    370                 375                 380
Ser Leu Thr Cys Leu Val Lys Gly Phe Tyr Pro Ser Asp Ile Ala Val
385                 390                 395                 400
Glu Trp Glu Ser Asn Gly Gln Pro Glu Asn Asn Tyr Lys Thr Thr Pro
                405                 410                 415
Pro Val Leu Asp Ser Asp Gly Ser Phe Phe Leu Tyr Ser Lys Leu Thr
            420                 425                 430
Val Asp Lys Ser Arg Trp Gln Gln Gly Asn Val Phe Ser Cys Ser Val
        435                 440                 445
Met His Glu Ala Leu His Asn His Tyr Thr Gln Lys Ser Leu Ser Leu
450                 455                 460
Ser Pro Gly Lys
```

<210> SEQ ID NO 14
<211> LENGTH: 239
<212> TYPE: PRT
<213> ORGANISM: Artificial Sequence
<220> FEATURE:
<223> OTHER INFORMATION: Mouse-human chimeric polypeptide

<400> SEQUENCE: 14

```
Met Asp Phe Gln Val Gln Ile Ile Ser Phe Leu Leu Ile Ser Ala Ser
1               5                   10                  15

Val Ile Met Ser Arg Gly Asp Ile Val Leu Thr Gln Thr Thr Asn Pro
            20                  25                  30

Val Thr Leu Gly Thr Ser Ala Ser Ile Ser Cys Arg Ser Ser Lys Ser
        35                  40                  45

Leu Leu His Ser Asn Gly Ile Thr Tyr Leu Tyr Trp Tyr Leu Gln Lys
    50                  55                  60

Pro Gly Gln Ser Pro Gln Leu Leu Ile Tyr Gln Met Ser Asn Leu Val
65                  70                  75                  80

Ser Gly Val Pro Asp Arg Phe Ser Ser Ser Gly Ser Gly Thr Asp Phe
                85                  90                  95

Thr Leu Arg Ile Ser Arg Val Glu Ala Glu Asp Val Gly Val Tyr Tyr
            100                 105                 110

Cys Ala Gln Asn Leu Glu Leu Pro Tyr Thr Phe Gly Gly Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

<210> SEQ ID NO 15
<211> LENGTH: 5
<212> TYPE: PRT
<213> ORGANISM: Mus sp.

<400> SEQUENCE: 15

```
Tyr Ser Trp Met Asn
1               5
```

<210> SEQ ID NO 16
<211> LENGTH: 6
<212> TYPE: PRT
<213> ORGANISM: Mus sp.

<400> SEQUENCE: 16

```
Gly Tyr Ala Phe Ser Tyr
1               5
```

<210> SEQ ID NO 17
<211> LENGTH: 10
<212> TYPE: PRT
<213> ORGANISM: Mus sp.

<400> SEQUENCE: 17

Gly Tyr Ala Phe Ser Tyr Ser Trp Met Asn
1               5                   10

<210> SEQ ID NO 18
<211> LENGTH: 16
<212> TYPE: PRT
<213> ORGANISM: Mus sp.

<400> SEQUENCE: 18

Arg Ser Ser Lys Ser Leu Leu His Ser Asn Gly Ile Thr Tyr Leu Tyr
1               5                   10                  15

<210> SEQ ID NO 19
<211> LENGTH: 7
<212> TYPE: PRT
<213> ORGANISM: Mus sp.

<400> SEQUENCE: 19

Gln Met Ser Asn Leu Val Ser
1               5

<210> SEQ ID NO 20
<211> LENGTH: 9
<212> TYPE: PRT
<213> ORGANISM: Mus sp.

<400> SEQUENCE: 20

Ala Gln Asn Leu Glu Leu Pro Tyr Thr
1               5

<210> SEQ ID NO 21
<211> LENGTH: 51
<212> TYPE: DNA
<213> ORGANISM: Mus sp.

<400> SEQUENCE: 21 cggattttc ctggagatgg ggatactgac tacaatggga aattcaaggg c        51

<210> SEQ ID NO 22
<211> LENGTH: 24
<212> TYPE: DNA
<213> ORGANISM: Mus sp.

<400> SEQUENCE: 22
tttcctggag atgggatac tgac                                       24

<210> SEQ ID NO 23
<211> LENGTH: 30
<212> TYPE: DNA
<213> ORGANISM: Mus sp.

<400> SEQUENCE: 23 cggattttc ctggagatgg ggatactgac                                 30

<210> SEQ ID NO 24
<211> LENGTH: 30
<212> TYPE: DNA
<213> ORGANISM: Mus sp.

<400> SEQUENCE: 24
aatgtctttg atggttactg gttagtttac                                    30

<210> SEQ ID NO 25
<211> LENGTH: 17
<212> TYPE: PRT
<213> ORGANISM: Mus sp.

<400> SEQUENCE: 25

Arg Ile Phe Pro Gly Asp Gly Asp Thr Asp Tyr Asn Gly Lys Phe Lys
1               5                   10                  15

Gly

<210> SEQ ID NO 26
<211> LENGTH: 8
<212> TYPE: PRT
<213> ORGANISM: Mus sp.

<400> SEQUENCE: 26

Phe Pro Gly Asp Gly Asp Thr Asp
1               5

<210> SEQ ID NO 27
<211> LENGTH: 10
<212> TYPE: PRT
<213> ORGANISM: Mus sp.

<400> SEQUENCE: 27

Arg Ile Phe Pro Gly Asp Gly Asp Thr Asp
1               5                   10

<210> SEQ ID NO 28
<211> LENGTH: 10
<212> TYPE: PRT
<213> ORGANISM: Mus sp.

<400> SEQUENCE: 28

Asn Val Phe Asp Gly Tyr Trp Leu Val Tyr
1               5                   10

<210> SEQ ID NO 29
<211> LENGTH: 357
<212> TYPE: DNA
<213> ORGANISM: Artificial
<220> FEATURE:
<223> OTHER INFORMATION: Mouse-human chimeric DNA

<400> SEQUENCE: 29
caggtgcaat tggtgcagtc tggcgctgaa gttaagaagc ctggggagttc agtgaaggtc     60 tcctgcaagg cttccggata caccttcagc tattcttgga tgagctgggt gcggcaggcc    120
cctggacaag gctcgagtg gatgggacgg atctttcccg gcgatgggga tactgactac    180
gcacagaaat tccaaggaag agtcacaatt accgccgaca atccactag cacagcctat     240 atggagctga gcagcctgag atctgaggac acggccgtgt attactgtgc aagaaatgtc    300
tttgatggtt actggcttgt ttactggggc cagggaaccc tggtcaccgt ctcctca      357

<210> SEQ ID NO 30
<211> LENGTH: 119
<212> TYPE: PRT
<213> ORGANISM: Artificial
<220> FEATURE:

<223> OTHER INFORMATION: Mouse-human chimeric polypeptide

<400> SEQUENCE: 30

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Tyr Ser
            20                  25                  30

Trp Met Ser Trp Val Arg Gln Ala Pro Gly Gln Gly Leu Glu Trp Met
        35                  40                  45

Gly Arg Ile Phe Pro Gly Asp Gly Asp Thr Asp Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115
```

<210> SEQ ID NO 31
<211> LENGTH: 357
<212> TYPE: DNA
<213> ORGANISM: Artificial
<220> FEATURE:
<223> OTHER INFORMATION: Mouse-human chimeric DNA

<400> SEQUENCE: 31

| | | | | | |
|---|---|---|---|---|---|
| caggtgcaat | tggtgcagtc | tggcgctgaa | gttaagaagc | ctgggagttc | agtgaaggtc | 60 |
| tcctgcaagg | cttccggata | cgccttcagc | tattcttgga | tgaactgggt | gcggcaggcc | 120 |
| cctggacaag | ggctcgagtg | gatgggacgg | atctttcccg | gcgatgggga | tactgactac | 180 |
| aatgggaaat | tcaagggcag | agtcacaatt | accgccgaca | aatccactag | cacagcctat | 240 |
| atggagctga | gcagcctgag | atctgaggac | acggccgtgt | attactgtgc | aagaaatgtc | 300 |
| tttgatggtt | actggcttgt | ttactggggc | cagggaaccc | tggtcaccgt | ctcctca | 357 |

<210> SEQ ID NO 32
<211> LENGTH: 119
<212> TYPE: PRT
<213> ORGANISM: Artificial
<220> FEATURE:
<223> OTHER INFORMATION: Mouse-human chimeric polypeptide

<400> SEQUENCE: 32

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Met Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
```

Thr Leu Val Thr Val Ser Ser
        115

<210> SEQ ID NO 33
<211> LENGTH: 366
<212> TYPE: DNA
<213> ORGANISM: Artificial
<220> FEATURE:
<223> OTHER INFORMATION: Mouse-human chimeric DNA

<400> SEQUENCE: 33
caggtgcaat tggtgcagtc tggcgctgaa gttaagaagc ctgggagttc agtgaaggtc     60
tcctgcaagg cttccggata cgccttcagc tattcttgga tgaactgggt gcggcaggcc    120
cctggacaag ggctcgagtg gatgggacgg atctttcccg gcgatgggga tactgactac    180
aatgggaaat tcaagggcag agtcacaatt accgccgaca atccactaga cacagcctat    240
atggagctga gcagcctgag atctgaggac acggccgtgt atctgtgtgc aagaaatgtc    300
tttgatggtt actggcttgt ttactggggc cagggaaccc tggtcaccgt ctcctcagct    360
agcacc                                                              366

<210> SEQ ID NO 34
<211> LENGTH: 119
<212> TYPE: PRT
<213> ORGANISM: Artificial
<220> FEATURE:
<223> OTHER INFORMATION: Mouse-human chimeric polypeptide

<400> SEQUENCE: 34

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Met Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Leu Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 35
<211> LENGTH: 357
<212> TYPE: DNA
<213> ORGANISM: Artificial
<220> FEATURE:
<223> OTHER INFORMATION: Mouse-human chimeric DNA

<400> SEQUENCE: 35
caggtgcaat tggtgcagtc tggcgctgaa gttaagaagc tggagcttc agtgaaggtc      60 tcctgcaagg tctccggata cgcgttcagc tattcttgga tgaactgggt gcggcaggcc    120
cctggacaag ggctcgagtg gatgggacgg atctttcccg gcgatgggga tactgactac    180

```
aatgggaaat tcaagggcag agtcacaatt accgccgaca atccactag cacagcctat      240 atggagctga gcagcctgag atctgaggac acggccgtgt attactgtgc aagaaatgtc      300
tttgatggtt actggcttgt ttactggggc cagggaaccc tggtcaccgt ctcctca         357
```

<210> SEQ ID NO 36
<211> LENGTH: 119
<212> TYPE: PRT
<213> ORGANISM: Artificial
<220> FEATURE:
<223> OTHER INFORMATION: Mouse-human chimeric polypeptide

<400> SEQUENCE: 36

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Ala Phe Ser Tyr Ser
            20                  25                  30

Trp Met Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115
```

<210> SEQ ID NO 37
<211> LENGTH: 357
<212> TYPE: DNA
<213> ORGANISM: Artificial
<220> FEATURE:
<223> OTHER INFORMATION: Mouse-human chimeric DNA

<400> SEQUENCE: 37

```
caggtgcaat tggtgcagtc tggcgctgaa gttaagaagc ctgggagttc agtgaaggtc      60
tcctgcaagg cttccggata cgcgttcagc tattcttgga tgagctgggt gcggcaggcg     120
cctggacaag ggctcgagtg gatgggacgg atctttcccg gcgatgggga tactgactac     180
aatgggaaat tcaagggcag agtcacaatt accgccgaca atccactag cacagcctat      240 atggagctga gcagcctgag atctgaggac acggccgtgt attactgtgc aagaaatgtc      300
tttgatggtt actggcttgt ttactggggc cagggaaccc tggtcaccgt ctcctca         357
```

<210> SEQ ID NO 38
<211> LENGTH: 119
<212> TYPE: PRT
<213> ORGANISM: Artificial
<220> FEATURE:
<223> OTHER INFORMATION: Mouse-human chimeric polypeptide

<400> SEQUENCE: 38

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Met Ser Trp Val Arg Gln Ala Pro Gly Gln Gly Leu Glu Trp Met
```

```
                    35                  40                  45
Gly Arg Ile Phe Pro Gly Asp Gly Asp Thr Asp Tyr Asn Gly Lys Phe
        50                  55                  60
Lys Gly Arg Val Thr Ile Thr Ala Asp Lys Ser Thr Ser Thr Ala Tyr
 65                  70                  75                  80
Met Glu Leu Ser Ser Leu Arg Ser Glu Asp Thr Ala Val Tyr Tyr Cys
                85                  90                  95
Ala Arg Asn Val Phe Asp Gly Tyr Trp Leu Val Tyr Trp Gly Gln Gly
                100                 105                 110
Thr Leu Val Thr Val Ser Ser
            115

<210> SEQ ID NO 39
<211> LENGTH: 357
<212> TYPE: DNA
<213> ORGANISM: Artificial
<220> FEATURE:
<223> OTHER INFORMATION: Mouse-human chimeric DNA

<400> SEQUENCE: 39
caggtgcaat tggtgcagtc tggcgctgaa gttaagaagc ctggggagttc agtgaaggtc      60 tcctgcaagg cttccggata cgccttcagc tattcttgga tcaattgggt gcggcaggcg     120
cctggacaag ggctcgagtg gatgggacgg atctttcccg gcgatgggga tactgactac     180
aatgggaaat tcaagggcag agtcacaatt accgccgaca atccactagc acagcctat     240 atggagctga gcagcctgag atctgaggac acggccgtgt attactgtgc aagaaatgtc     300
tttgatggtt actggcttgt ttactggggc cagggaaccc tggtcaccgt ctcctca       357

<210> SEQ ID NO 40
<211> LENGTH: 119
<212> TYPE: PRT
<213> ORGANISM: Artificial
<220> FEATURE:
<223> OTHER INFORMATION: Mouse-human chimeric polypeptide

<400> SEQUENCE: 40

Gln Val Gln Leu Val Gln Ser Gly Ala Glu Val Lys Lys Pro Gly Ser
 1               5                  10                  15
Ser Val Lys Val Ser Cys Lys Ala Ser Gly Tyr Ala Phe Ser Tyr Ser
                20                  25                  30
Trp Ile Asn Trp Val Arg Gln Ala Pro Gly Gln Gly Leu Glu Trp Met
            35                  40                  45
Gly Arg Ile Phe Pro Gly Asp Gly Asp Thr Asp Tyr Asn Gly Lys Phe
        50                  55                  60
Lys Gly Arg Val Thr Ile Thr Ala Asp Lys Ser Thr Ser Thr Ala Tyr
 65                  70                  75                  80
Met Glu Leu Ser Ser Leu Arg Ser Glu Asp Thr Ala Val Tyr Tyr Cys
                85                  90                  95
Ala Arg Asn Val Phe Asp Gly Tyr Trp Leu Val Tyr Trp Gly Gln Gly
                100                 105                 110
Thr Leu Val Thr Val Ser Ser
            115

<210> SEQ ID NO 41
<211> LENGTH: 357
<212> TYPE: DNA
<213> ORGANISM: Artificial
<220> FEATURE:
```

<223> OTHER INFORMATION: Mouse-human chimeric DNA

<400> SEQUENCE: 41

```
caggtgcaat tggtgcagtc tggcgctgaa gttaagaagc ctgggagttc agtgaaggtc    60
tcctgcaagg cttccggata cgccttcagc tattcttgga tctcgtgggt gcggcaggcg   120
cctggacaag ggctcgagtg gatgggacgg atctttcccg gcgatgggga tactgactac   180
aatgggaaat tcaagggcag agtcacaatt accgccgaca atccactaga cacagcctat   240
atggagctga gcagcctgag atctgaggac acggccgtgt attactgtgc aagaaatgtc   300
tttgatggtt actggcttgt ttactggggc cagggaaccc tggtcaccgt ctcctca     357
```

<210> SEQ ID NO 42
<211> LENGTH: 119
<212> TYPE: PRT
<213> ORGANISM: Artificial
<220> FEATURE:
<223> OTHER INFORMATION: Mouse-human chimeric polypeptide

<400> SEQUENCE: 42

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
                20                  25                  30

Trp Ile Ser Trp Val Arg Gln Ala Pro Gly Gln Gly Leu Glu Trp Met
            35                  40                  45

Gly Arg Ile Phe Pro Gly Asp Gly Asp Thr Asp Tyr Asn Gly Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
                100                 105                 110

Thr Leu Val Thr Val Ser Ser
        115
```

<210> SEQ ID NO 43
<211> LENGTH: 357
<212> TYPE: DNA
<213> ORGANISM: Artificial
<220> FEATURE:
<223> OTHER INFORMATION: Mouse-human chimeric DNA

<400> SEQUENCE: 43

```
caggtgcaat tggtgcagtc tggcgctgaa gttaagaagc ctggcgcctc agtgaaggtc    60
tcctgcaagg cttccggata caccttcaca tacagctgga tgaactgggt gcggcaggcc   120
cctggacaag ggctcgagtg gatgggacgg atctttcccg gcgatgggga tactgactac   180
aatgggaaat tcaagggcag agtcacaatt accgccgaca atccactaga cacagcctat   240
atggagctga gcagcctgag atctgaggac acggccgtgt attactgtgc aagaaatgtc   300
tttgatggtt actggcttgt ttactggggc cagggaaccc tggtcaccgt ctcctca     357
```

<210> SEQ ID NO 44
<211> LENGTH: 119
<212> TYPE: PRT
<213> ORGANISM: Artificial
<220> FEATURE:
<223> OTHER INFORMATION: Mouse-human chimeric polypeptide

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Tyr Ser
            20                  25                  30

Trp Met Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 45
<211> LENGTH: 357
<212> TYPE: DNA
<213> ORGANISM: Artificial
<220> FEATURE:
<223> OTHER INFORMATION: Mouse-human chimeric DNA

<400> SEQUENCE: 45
caggtgcaat tggtgcagtc tggcgctgaa gttaagaagc ctggcgcctc agtgaaggtc      60
tcctgcaagg cttccggata caccttcagc tattcttgga tgaactgggt gcggcaggcc     120
cctggacaag ggctcgagtg gatgggacgg atctttcccg gcgatgggga tactgactac     180
aatgggaaat tcaagggcag agtcacaatt accgccgaca aatccactag cacagcctat     240
atggagctga gcagcctgag atctgaggac acggccgtgt attactgtgc aagaaatgtc     300
tttgatggtt actggcttgt ttactggggc cagggaaccc tggtcaccgt ctcctca        357

<210> SEQ ID NO 46
<211> LENGTH: 119
<212> TYPE: PRT
<213> ORGANISM: Artificial
<220> FEATURE:
<223> OTHER INFORMATION: Mouse-human chimeric polypeptide

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Tyr Ser
            20                  25                  30

Trp Met Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 47
<211> LENGTH: 357
<212> TYPE: DNA
<213> ORGANISM: Artificial
<220> FEATURE:
<223> OTHER INFORMATION: Mouse-human chimeric DNA

<400> SEQUENCE: 47
caggtgcaat tggtgcagtc tggcgctgaa gttaagaagc ctggggcctc agtgaaggtc    60
tcctgcaagg cttccggata caccttcacc tattcttgga tgcactgggt gcggcaggcc   120
cctggacaag gctcgagtg gatgggacgg atctttcccg gcgatgggga tactgactac   180
gcacagaaat tccaaggaag agtcacaatg acacgggaca cgtccacttc caccgtctat   240
atggagctga gcagcctgag atctgaggac acggccgtgt attactgtgc aagaaatgtc   300
tttgatggtt actggcttgt ttactggggc cagggaaccc tggtcaccgt ctcctca     357

<210> SEQ ID NO 48
<211> LENGTH: 119
<212> TYPE: PRT
<213> ORGANISM: Artificial
<220> FEATURE:
<223> OTHER INFORMATION: Mouse-human chimeric polypeptide

<400> SEQUENCE: 48

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Tyr Ser
            20                  25                  30

Trp Met His Trp Val Arg Gln Ala Pro Gly Gln Gly Leu Glu Trp Met
        35                  40                  45

Gly Arg Ile Phe Pro Gly Asp Gly Asp Thr Asp Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 49
<211> LENGTH: 357
<212> TYPE: DNA
<213> ORGANISM: Artificial
<220> FEATURE:
<223> OTHER INFORMATION: Mouse-human chimeric DNA

<400> SEQUENCE: 49
gaggtgcaat tggtgcagtc tggcgctgaa gttaagaagc tggggccac cgtgaagatc    60 tcctgcaagg tgtccggata caccttcacc tattcttgga tgcactgggt gcagcaggcc   120
cctggaaagg gctcgagtg gatgggacgg atctttcccg gcgatgggga tactgactac   180
gcagagaaat tccaaggaag agtcacaatc acagccgaca cgtccactga caccgcctat   240
atggagctga gcagcctgag atctgaggac acggccgtgt attactgtgc aaccaatgtc   300

```
tttgatggtt actggcttgt ttactggggc agggaaccc tggtcaccgt ctcctca      357
```

<210> SEQ ID NO 50
<211> LENGTH: 119
<212> TYPE: PRT
<213> ORGANISM: Artificial
<220> FEATURE:
<223> OTHER INFORMATION: Mouse-human chimeric polypeptide

<400> SEQUENCE: 50

```
Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Tyr Ser
            20                  25                  30

Trp Met His Trp Val Gln Gln Ala Pro Gly Lys Gly Leu Glu Trp Met
        35                  40                  45

Gly Arg Ile Phe Pro Gly Asp Gly Asp Thr Asp Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asn Val Phe Asp Gly Tyr Trp Leu Val Tyr Trp Gly Gln Gly
            100                 105                 110

Thr Leu Val Thr Val Ser Ser
        115
```

<210> SEQ ID NO 51
<211> LENGTH: 357
<212> TYPE: DNA
<213> ORGANISM: Artificial
<220> FEATURE:
<223> OTHER INFORMATION: Mouse-human chimeric DNA

<400> SEQUENCE: 51

```
gaggtgcaat tggtgcagtc tggcgctgaa gttaagaagc tggggccac cgtgaagatc      60 tcctgcaagg tgtccggata caccttcacc tattcttgga tgaactgggt gcagcaggcc    120
cctggaaagg ggctcgagtg gatgggacgg atctttcccg gcgatgggga tactgactac    180
aatgggaaat tcaagggaag agtcacaatc acagccgaca cgtccactga caccgcctat    240
atggagctga gcagcctgag atctgaggac acggccgtgt attactgtgc aaccaatgtc    300
tttgatggtt actggcttgt ttactggggc agggaaccc tggtcaccgt ctcctca       357
```

<210> SEQ ID NO 52
<211> LENGTH: 119
<212> TYPE: PRT
<213> ORGANISM: Artificial
<220> FEATURE:
<223> OTHER INFORMATION: Mouse-human chimeric polypeptide

<400> SEQUENCE: 52

```
Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Tyr Ser
            20                  25                  30

Trp Met Asn Trp Val Gln Gln Ala Pro Gly Lys Gly Leu Glu Trp Met
        35                  40                  45

Gly Arg Ile Phe Pro Gly Asp Gly Asp Thr Asp Tyr Asn Gly Lys Phe
```

```
                  50                  55                  60
Lys Gly Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr Asn Val Phe Asp Gly Tyr Trp Leu Val Tyr Trp Gly Gln Gly
                100                 105                 110

Thr Leu Val Thr Val Ser Ser
        115

<210> SEQ ID NO 53
<211> LENGTH: 366
<212> TYPE: DNA
<213> ORGANISM: Artificial
<220> FEATURE:
<223> OTHER INFORMATION: Mouse-human chimeric DNA

<400> SEQUENCE: 53
cagatgcaat tggtgcagtc tggcgctgaa gttaagaaga ccgggagttc agtgaaggtc      60
tcctgcaagg cttccggata caccttcacc tattcttgga tgagctgggt gcggcaggcc    120
cctggacaag gctcgagtg gatgggacgg atctttcccg gcgatgggga tactgactac     180
gcacagaaat tccaaggaag agtcacaatt accgccgaca atccactag cacagcctat     240 atggagctga gcagcctgag atctgaggac acggccgtgt attactgtgc aagaaatgtc    300
tttgatggtt actggcttgt ttactggggc cagggaaccc tggtcaccgt ctcctcagct    360
agcacc                                                              366

<210> SEQ ID NO 54
<211> LENGTH: 119
<212> TYPE: PRT
<213> ORGANISM: Artificial
<220> FEATURE:
<223> OTHER INFORMATION: Mouse-human chimeric polypeptide

<400> SEQUENCE: 54

Gln Met Gln Leu Val Gln Ser Gly Ala Glu Val Lys Lys Thr Gly Ser
 1               5                  10                  15

Ser Val Lys Val Ser Cys Lys Ala Ser Gly Tyr Thr Phe Thr Tyr Ser
                20                  25                  30

Trp Met Ser Trp Val Arg Gln Ala Pro Gly Gln Gly Leu Glu Trp Met
            35                  40                  45

Gly Arg Ile Phe Pro Gly Asp Gly Asp Thr Asp Tyr Ala Gln Lys Phe
     50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asn Val Phe Asp Gly Tyr Trp Leu Val Tyr Trp Gly Gln Gly
                100                 105                 110

Thr Leu Val Thr Val Ser Ser
        115

<210> SEQ ID NO 55
<211> LENGTH: 357
<212> TYPE: DNA
<213> ORGANISM: Artificial
<220> FEATURE:
<223> OTHER INFORMATION: Mouse-human chimeric DNA
```

<400> SEQUENCE: 55

```
gaagtgcagc tggtggagtc tggaggaggc ttggtcaagc ctggcgggtc cctgcggctc        60
tcctgtgcag cctctggatt cacatttagc tattcttgga tgaactgggt gcggcaggct       120
cctggaaagg gcctcgagtg gtgggacgg atctttcccg gcgatgggga tactgactac       180
aatgggaaat tcaagggcag agtcacaatt accgccgaca atccactag cacagcctat       240
atggagctga gcagcctgag atctgaggac acggccgtgt attactgtgc aagaaatgtc       300
tttgatggtt actggcttgt ttactgggc cagggaaccc tggtcaccgt ctcctca           357
```

<210> SEQ ID NO 56
<211> LENGTH: 119
<212> TYPE: PRT
<213> ORGANISM: Artificial
<220> FEATURE:
<223> OTHER INFORMATION: Mouse-human chimeric polypeptide

<400> SEQUENCE: 56

```
Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Tyr Ser
             20                  25                  30

Trp Met Asn Trp Val Arg Gln Ala Pro Gly Lys Gly Leu Glu Trp Val
         35                  40                  45

Gly Arg Ile Phe Pro Gly Asp Gly Asp Thr Asp Tyr Asn Gly Lys Phe
     50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asn Val Phe Asp Gly Tyr Trp Leu Val Tyr Trp Gly Gln Gly
            100                 105                 110

Thr Leu Val Thr Val Ser Ser
        115
```

<210> SEQ ID NO 57
<211> LENGTH: 456
<212> TYPE: DNA
<213> ORGANISM: Artificial
<220> FEATURE:
<223> OTHER INFORMATION: Mouse-human chimeric DNA

<400> SEQUENCE: 57

```
cggaattcgg cccaccggtg gccaccatgg actggacctg gaggatcctc ttcttggtgg        60
cagcagccac aggagcccac tccgaagtgc agctggtgga gtctggagga ggcttggtca       120
agcctggcgg gtccctgcgg ctctcctgtg cagcctctgg attcgcattc agctattctt       180
ggatgaactg ggtgcggcag gctcctggaa agggcctcga gtgggtggga cggatctttc       240
ccggcgatgg ggatactgac tacaatggga aattcaaggg cagagtcaca attaccgccg       300
acaaatccac tagcacagcc tatatggagc tgagcagcct gagatctgag gacacggccg       360
tgtattactg tgcaagaaat gtctttgatg gttactggct tgtttactgg ggccagggaa       420
ccctggtcac cgtctcctca gctagcgaat tctcga                                 456
```

<210> SEQ ID NO 58
<211> LENGTH: 119
<212> TYPE: PRT

<213> ORGANISM: Artificial
<220> FEATURE:
<223> OTHER INFORMATION: Mouse-human chimeric polypeptide

<400> SEQUENCE: 58

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Ala Phe Ser Tyr Ser
            20                  25                  30

Trp Met Asn Trp Val Arg Gln Ala Pro Gly Lys Gly Leu Glu Trp Val
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115
```

<210> SEQ ID NO 59
<211> LENGTH: 357
<212> TYPE: DNA
<213> ORGANISM: Artificial
<220> FEATURE:
<223> OTHER INFORMATION: Mouse-human chimeric DNA

<400> SEQUENCE: 59

```
caggtgcagc tggtggagtc tggaggaggc ttggtcaagc ctggcgggtc cctgcggctc     60
tcctgtgcag cctctggatt cacatttagc tattcttgga tgaactgggt gcggcaggct    120
cctggaaagg gcctcgagtg ggtgggacgg atctttcccg gcgatgggga tactgactac    180
aatgggaaat tcaagggcag agtcacaatt accgccgaca atccactag cacagcctat     240 atggagctga gcagcctgag atctgaggac acggccgtgt attactgtgc aagaaatgtc    300
tttgatggtt actggcttgt ttactggggc cagggaaccc tggtcaccgt ctcctca       357
```

<210> SEQ ID NO 60
<211> LENGTH: 119
<212> TYPE: PRT
<213> ORGANISM: Artificial
<220> FEATURE:
<223> OTHER INFORMATION: Mouse-human chimeric polypeptide

<400> SEQUENCE: 60

```
Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Val
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 61
<211> LENGTH: 456
<212> TYPE: DNA
<213> ORGANISM: Artificial
<220> FEATURE:
<223> OTHER INFORMATION: Mouse-human chimeric DNA

<400> SEQUENCE: 61
cggaattcgg cccaccggtg gccaccatgg actggacctg gaggatcctc ttcttggtgg      60
cagcagccac aggagctcac tccgaagtgc agctcgtgga gtctggagca ggcttggtca     120
agcctggcgg gtccctgcgg ctctcctgcg cagcctctgg attcacattt agctattctt     180
ggatgaactg ggtgcggcag gctcctggaa agggcctcga gtgggtggga cggatctttc     240
ccggcgatgg ggatactgac tacaatggga aattcaaggg cagagtcaca attaccgccg     300
acaaatccac tagcacagcc tatatggagc tgagcagcct gagatctgag gacacggccg     360
tgtattactg tgcaagaaat gtctttgatg gttactggct tgtttactgg ggccagggaa     420
ccctggtcac cgtctcctca gctagcgaat tctcga                               456

<210> SEQ ID NO 62
<211> LENGTH: 119
<212> TYPE: PRT
<213> ORGANISM: Artificial
<220> FEATURE:
<223> OTHER INFORMATION: Mouse-human chimeric polypeptide

<400> SEQUENCE: 62

Glu Val Gln Leu Val Glu Ser Gly Ala Gly Leu Val Lys Pro Gly Gly
1               5                   10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 63
<211> LENGTH: 456
<212> TYPE: DNA
<213> ORGANISM: Artificial
<220> FEATURE:
<223> OTHER INFORMATION: Mouse-human chimeric DNA

<400> SEQUENCE: 63
cggaattcgg cccaccggtg gccaccatgg actggacctg gaggatcctc ttcttggtgg      60

```
cagcagccac aggagctcac tccgaagtgc agctcgtcga gtctggagga ggcgtggtca    120
agcctggcgg gtccctgcgg ctctcctgcg cagcctctgg attcacattt agctattctt    180
ggatgaactg ggtgcggcag gctcctggaa agggcctcga gtgggtggga cggatctttc    240
ccggcgatgg ggatactgac tacaatggga aattcaaggg cagagtcaca attaccgccg    300
acaaatccac tagcacagcc tatatggagc tgagcagcct gagatctgag gacacggccg    360
tgtattactg tgcaagaaat gtctttgatg gttactggct tgtttactgg ggccagggaa    420
ccctggtcac cgtctcctca gctagcgaat tctcga                              456
```

<210> SEQ ID NO 64
<211> LENGTH: 119
<212> TYPE: PRT
<213> ORGANISM: Artificial
<220> FEATURE:
<223> OTHER INFORMATION: Mouse-human chimeric polypeptide

<400> SEQUENCE: 64

```
Glu Val Gln Leu Val Glu Ser Gly Gly Gly Val Val Lys Pro Gly Gly
1               5                   10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115
```

<210> SEQ ID NO 65
<211> LENGTH: 456
<212> TYPE: DNA
<213> ORGANISM: Artificial
<220> FEATURE:
<223> OTHER INFORMATION: Mouse-human chimeric DNA

<400> SEQUENCE: 65

```
cggaattcgg cccaccggtg gccaccatgg actggacctg gaggatcctc ttcttggtgg     60
cagcagccac aggagctcac tccgaagtgc agctggtcga gtccggagga ggcttgaaga    120
agcctggcgg gtccctgcgg ctctcctgcg cagcctctgg attcacattt agctattctt    180
ggatgaactg ggtgcggcag gctcctggaa agggcctcga gtgggtggga cggatctttc    240
ccggcgatgg ggatactgac tacaatggga aattcaaggg cagagtcaca attaccgccg    300
acaaatccac tagcacagcc tatatggagc tgagcagcct gagatctgag gacacggccg    360
tgtattactg tgcaagaaat gtctttgatg gttactggct tgtttactgg ggccagggaa    420
ccctggtcac cgtctcctca gctagcgaat tctcga                              456
```

<210> SEQ ID NO 66
<211> LENGTH: 119
<212> TYPE: PRT
<213> ORGANISM: Artificial

<220> FEATURE:
<223> OTHER INFORMATION: Mouse-human chimeric polypeptide

<400> SEQUENCE: 66

Glu Val Gln Leu Val Glu Ser Gly Gly Gly Leu Lys Lys Pro Gly Gly
1               5                   10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 67
<211> LENGTH: 456
<212> TYPE: DNA
<213> ORGANISM: Artificial
<220> FEATURE:
<223> OTHER INFORMATION: Mouse-human chimeric DNA

<400> SEQUENCE: 67
cggaattcgg cccaccggtg gccaccatgg actggacctg gaggatcctc ttcttggtgg    60
cagcagccac aggagcccac tccgaagtgc agctggtgga gtctggagga ggcttggtca   120
agcctggctc ttccctgcgg ctctcctgcg cagcctctgg attcacattt agctattctt   180
ggatgaactg ggtgcggcag gctcctggaa agggcctcga gtgggtggga cggatctttc   240
ccggcgatgg ggatactgac tacaatggga aattcaaggg cagagtcaca attaccgccg   300
acaaatccac tagcacagcc tatatggagc tgagcagcct gagatctgag gacacggccg   360
tgtattactg tgcaagaaat gtctttgatg gttactggct tgtttactgg ggccagggaa   420
ccctggtcac cgtctcctca gctagcgaat tctcga                             456

<210> SEQ ID NO 68
<211> LENGTH: 119
<212> TYPE: PRT
<213> ORGANISM: Artificial
<220> FEATURE:
<223> OTHER INFORMATION: Mouse-human chimeric polypeptide

<400> SEQUENCE: 68

Glu Val Gln Leu Val Glu Ser Gly Gly Gly Leu Val Lys Pro Gly Ser
1               5                   10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

```
Met Glu Leu Ser Ser Leu Arg Ser Glu Asp Thr Ala Val Tyr Tyr Cys
            85                  90                  95

Ala Arg Asn Val Phe Asp Gly Tyr Trp Leu Val Tyr Trp Gly Gln Gly
            100                 105                 110

Thr Leu Val Thr Val Ser Ser
        115
```

<210> SEQ ID NO 69
<211> LENGTH: 456
<212> TYPE: DNA
<213> ORGANISM: Artificial
<220> FEATURE:
<223> OTHER INFORMATION: Mouse-human chimeric DNA

<400> SEQUENCE: 69

```
cggaattcgg cccaccggtg gccaccatgg actggacctg gaggatcctc ttcttggtgg    60
cagcagccac aggagcccac tccgaagtgc agctggtgga gtctggagga ggcttggtca   120
agcctggcgg gtccctgcgg gtcagctgcg cagcctctgg attcacattt agctattctt   180
ggatgaactg ggtgcggcag gctcctggaa agggcctcga gtgggtggga cggatctttc   240
ccggcgatgg ggatactgac tacaatggga aattcaaggg cagagtcaca attaccgccg   300
acaaatccac tagcacagcc tatatggagc tgagcagcct gagatctgag gacacggccg   360
tgtattactg tgcaagaaat gtctttgatg gttactggct tgtttactgg ggccagggaa   420
ccctggtcac cgtctcctca gctagcgaat tctcga                             456
```

<210> SEQ ID NO 70
<211> LENGTH: 119
<212> TYPE: PRT
<213> ORGANISM: Artificial
<220> FEATURE:
<223> OTHER INFORMATION: Mouse-human chimeric polypeptide

<400> SEQUENCE: 70

```
Glu Val Gln Leu Val Glu Ser Gly Gly Gly Leu Val Lys Pro Gly Gly
1               5                   10                  15

Ser Leu Arg Val Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Asn Val Phe Asp Gly Tyr Trp Leu Val Tyr Trp Gly Gln Gly
            100                 105                 110

Thr Leu Val Thr Val Ser Ser
        115
```

<210> SEQ ID NO 71
<211> LENGTH: 456
<212> TYPE: DNA
<213> ORGANISM: Artificial
<220> FEATURE:
<223> OTHER INFORMATION: Mouse-human chimeric DNA

<400> SEQUENCE: 71
cggaattcgg cccaccggtg gccaccatgg actggacctg gaggatcctc ttcttggtgg    60
cagcagccac aggagcccac tccgaagtgc agctggtgga gtctggagga ggcttggtca   120
agcctggcgg gtccctgcgg ctctcctgcg cagcctctgg attcacattt agctattctt   180
ggatgaactg ggtgcggcag gctcctggaa agggcctcga gtgggtggga cggatctttc   240
ccggcgatgg ggatactgac tacaatggga aattcaaggg cagagtcaca attaccgccg   300
acaaatccac tagcacagcc tatatggagc tgagcagcct gagatctgag gacacggccg   360
tgtattactg tgcaagaaat gtctttgatg gttactggct tgtttactgg ggccagggaa   420
ccctggtcac cgtctcctca gctagcgaat tctcga                             456

<210> SEQ ID NO 72
<211> LENGTH: 119
<212> TYPE: PRT
<213> ORGANISM: Artificial
<220> FEATURE:
<223> OTHER INFORMATION: Mouse-human chimeric polypeptide

<400> SEQUENCE: 72

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 73
<211> LENGTH: 57
<212> TYPE: DNA
<213> ORGANISM: Homo sapiens

<400> SEQUENCE: 73
atggactgga cctggaggat cctcttcttg gtggcagcag ccacaggagc ccactcc        57

<210> SEQ ID NO 74
<211> LENGTH: 19
<212> TYPE: PRT
<213> ORGANISM: Homo sapiens

<400> SEQUENCE: 74

Met Asp Trp Thr Trp Arg Ile Leu Phe Leu Val Ala Ala Ala Thr Gly
1               5                   10                  15

Ala His Ser

<210> SEQ ID NO 75
<211> LENGTH: 345
<212> TYPE: DNA
<213> ORGANISM: Artificial

<220> FEATURE:
<223> OTHER INFORMATION: Mouse-human chimeric DNA

<400> SEQUENCE: 75

```
gatatcgtga tgacccagac tccactctcc ctgcccgtca cccctggaga gcccgccagc    60
attagctgca ggtctagcaa gagcctcttg cacagcaatg gcatcactta tttgtattgg   120
tacctgcaaa agccagggca gtctccacag ctcctgattt atcaaatgtc caaccttgtc   180
tctggcgtcc ctgaccggtt ctccggatcc gggtcaggca ctgatttcac actgaaaatc   240
agcagggtgg aggctgagga tgttggagtt tattactgcg ctcagaatct agaacttcct   300
tacaccttcg gcggagggac caaggtggag atcaaacgta cggtg                   345
```

<210> SEQ ID NO 76
<211> LENGTH: 115
<212> TYPE: PRT
<213> ORGANISM: Artificial
<220> FEATURE:
<223> OTHER INFORMATION: Mouse-human chimeric polypeptide

<400> SEQUENCE: 76

```
Asp Ile Val Met Thr Gln Thr Pro Leu Ser Leu Pro Val Thr Pro Gly
1               5                   10                  15
Glu Pro Ala Ser Ile Ser Cys Arg Ser Ser Lys Ser Leu Leu His Ser
            20                  25                  30
Asn Gly Ile Thr Tyr Leu Tyr Trp Tyr Leu Gln Lys Pro Gly Gln Ser
        35                  40                  45
Pro Gln Leu Leu Ile Tyr Gln Met Ser Asn Leu Val Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Ala Gln Asn
                85                  90                  95
Leu Glu Leu Pro Tyr Thr Phe Gly Gly Gly Thr Lys Val Glu Ile Lys
            100                 105                 110
Arg Thr Val
        115
```

<210> SEQ ID NO 77
<211> LENGTH: 66
<212> TYPE: DNA
<213> ORGANISM: Homo sapiens

<400> SEQUENCE: 77

```
atggacatga gggtccccgc tcagctcctg ggcctcctgc tgctctggtt cccaggtgcc    60
aggtgt                                                              66
```

<210> SEQ ID NO 78
<211> LENGTH: 22
<212> TYPE: PRT
<213> ORGANISM: Homo sapiens

<400> SEQUENCE: 78

```
Met Asp Met Arg Val Pro Ala Gln Leu Leu Gly Leu Leu Leu Leu Trp
1               5                   10                  15
Phe Pro Gly Ala Arg Cys
            20
```

<210> SEQ ID NO 79

```
<211> LENGTH: 21
<212> TYPE: DNA
<213> ORGANISM: Artificial
<220> FEATURE:
<223> OTHER INFORMATION: nucleic acids encoding linker peptides

<400> SEQUENCE: 79
gaggtcaagc tgcagcagtc t                                              21

<210> SEQ ID NO 80
<211> LENGTH: 21
<212> TYPE: DNA
<213> ORGANISM: Artificial
<220> FEATURE:
<223> OTHER INFORMATION: complementary nucleic acid sequence of SEQ ID
      NO: 79, which encodes a linker peptide

<400> SEQUENCE: 80
agactgctgc agcttgacct c                                              21

<210> SEQ ID NO 81
<211> LENGTH: 7
<212> TYPE: PRT
<213> ORGANISM: Artificial
<220> FEATURE:
<223> OTHER INFORMATION: linker peptides

<400> SEQUENCE: 81

Glu Val Lys Leu Gln Gln Ser
1               5

<210> SEQ ID NO 82
<211> LENGTH: 24
<212> TYPE: DNA
<213> ORGANISM: Artificial
<220> FEATURE:
<223> OTHER INFORMATION: nucleic acids encoding linker peptides

<400> SEQUENCE: 82
gacattgtgc tcacccaaac taca                                           24

<210> SEQ ID NO 83
<211> LENGTH: 24
<212> TYPE: DNA
<213> ORGANISM: Artificial
<220> FEATURE:
<223> OTHER INFORMATION: complementary nucleic acid sequence of SEQ ID
      NO: 82, which encodes a linker peptide

<400> SEQUENCE: 83
tgtagtttgg gtgagcacaa tgtc                                           24

<210> SEQ ID NO 84
<211> LENGTH: 8
<212> TYPE: PRT
<213> ORGANISM: Artificial
<220> FEATURE:
<223> OTHER INFORMATION: linker peptides

<400> SEQUENCE: 84

Asp Ile Val Leu Thr Gln Thr Thr
1               5

<210> SEQ ID NO 85
<211> LENGTH: 336
<212> TYPE: DNA
<213> ORGANISM: Mus sp.
```

```
<400> SEQUENCE: 85
tgcagagaca gtgaccagag tcccttggcc ccagtaaact aaccagtaac catcaaagac        60
atttcttgca cataaataga ccgcagagtc cacagaggtc aggctggtga gttgcatgta       120
ggctgtgttg gaggatttgt cagcagtcag tgtggccttg cccttgaatt tcccattgta       180
gtcagtatcc ccatctccag gaaaaatccg tccaatccac tcaagaccct gtccaggcct       240
cagtttcacc cagttcatcc aagagtaact gaatgcgtag ccagaagctt tgcaggaaat       300
cttcactgag gccccaggct tcaccagttc aggtcc                                  336

<210> SEQ ID NO 86
<211> LENGTH: 309
<212> TYPE: DNA
<213> ORGANISM: Mus sp.

<400> SEQUENCE: 86
ccgtttattt tccagcttgg tcccccctcc gaacgtgtac ggaagttcta gattttgagc        60
acagtaataa acacccacat cctcagcctc cactctgctg attctcagtg tgaaatcagt       120
tcctgaccca ctgctactga acctgtctgg gactcctgag acaaggttgg acatctgata       180
aatcaggagc tgaggagact ggcctggctt ctgcagatac caatacaaat aagtgatgcc       240
attactatgt aggagactct tactagacct gcaggagatg gaagctgatg ttccaagagt       300
gactggatt                                                                309
```